US006423496B1

(12) United States Patent
Frudakis et al.

(10) Patent No.: US 6,423,496 B1
(45) Date of Patent: Jul. 23, 2002

(54) COMPOSITIONS AND METHODS FOR THE TREATMENT AND DIAGNOSIS OF BREAST CANCER

(75) Inventors: Tony N. Frudakis, Seattle; John M. Smith, Everett; Steven G. Reed, Bellevue, all of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/598,326

(22) Filed: Jun. 20, 2000

Related U.S. Application Data

(60) Division of application No. 08/838,762, filed as application No. PCT/US97/00485 on Jan. 10, 1997, now abandoned, which is a continuation-in-part of application No. 08/700,014, filed on Aug. 20, 1996, which is a continuation-in-part of application No. 08/585,392, filed on Jan. 11, 1996, now abandoned.

(51) Int. Cl.[7] ................................................................
C12Q 1/68; C07H 19/00; C07H 21/00; C07H 21/02; C07H 21/04
(52) U.S. Cl. .................... 435/6; 536/22.1; 536/23.1; 536/24.3
(58) Field of Search .............................. 435/6; 536/22.1, 536/23.1, 24.3

(56) References Cited

U.S. PATENT DOCUMENTS

| 5,231,012 A | 7/1993 | Mosmann et al. ........ 435/69.52 |
| 5,428,145 A | 6/1995 | Okamoto et al. ......... 536/23.72 |
| 5,516,650 A | 5/1996 | Foster et al. ................ 435/68.1 |
| 5,523,225 A | 6/1996 | Kraus ....................... 435/240.1 |
| 5,585,270 A | 12/1996 | Grotendorst et al. ...... 435/252.3 |

FOREIGN PATENT DOCUMENTS

| GB | 2273099 A | 6/1994 |
| WO | WO 91/02062 | 2/1991 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 9/25431 | 7/1997 |
| WO | WO 97/25426 | 7/1997 |

OTHER PUBLICATIONS

Biolabs Catalog, p. 61, 1986*
Attwood Science, vol. 290, pp. 471–473, Oct. 2000.*
Gerhold et al. BioEssays, vol. 18(12) pp. 973–981, 1986.*
Wells et al. Journal of Leucocyte Biology, vol. 61, pp. 545–550, 1997.*
Russel et al. Journal of Molecular Biology, vol. 244, pp. 332–350, 1994.*
Anderson et al., "Sequence and organization of the human mitochondrial genome," Nature 290:457–465, 1981.
Bauer et al., "Identification of differentially expressed mRNA species by an improved display technique (DDRT–PCR)," Nucleic Acids Research 21(18):4272–4280, 1993.
Bernard et al., "Cloning and Sequencing of Pro–α1(XI) Collagen cDNA Demostrates That Type XI Belongs to the Fibrillar Class of Collagens and Reveals That the Expression of the Gene Is Not Restricted to Cartilagenous Tissue," J. Biol. Chem. 263(32):17159–17166, 1988.

(List continued on next page.)

Primary Examiner—Jezia Riley
(74) Attorney, Agent, or Firm—Seed Intellectual Property Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

3 Claims, 22 Drawing Sheets

OTHER PUBLICATIONS

Bratthauser et al., "Expression of LINE–1 Retrotransposons in Human Breast Cancer," *Cancer 73*:2333–2336, 1994.

Byrne et al., "A Screening Method ot Identify Genes Commonly Overexpressed in Carcinomas and the Identification of a Novel Complementary DNA Sequence," *Cancer Research 55*: 2869–2903, 1995.

Chen and Sager, "Differential Expression of Human Tissue Factor in Normal Mammary Epithelial Cells and in Carcinomas," *Molecular Medicine 1*(2):153–16, 1995.

Cordonnier et al., "Isolation of Novel Human Endogenous Retrovirus–Like Elements with Foamy Virus–Related pol Sequence," *Journal of Virology 69*(9):5890–5897, 1995.

Databank Genbank Accession No. Z34289, 1995.

Ezzell, "Cancer "Vaccines": An Idea Whose Time Has Come?," *The Journal of NIH Research 7*:46–49, 1995.

Gura, "Systems for Identifying New Drugs Are Often Faulty," *Science 278*:1041–1042, 1997.

Haltmeier et al., "Identification of S71–Related Human Endogenous Retroviral Sequences with Full–Length *pol* Genes,"*Virology 209*:550–560, 1995.

Hillier et al., Genbank Accession No. H80165, 1995.

Hillier et al., Genbank Accession No. R19532, 1995.

Hillier et al., Genbank Accession No. R55637, 1995.

Hillier et al., Genbank Accession No. R60426, 1995.

Hillier et al., Genbank Accession No. T83348, 1995.

Hillier et al., Genbank Accession No. R35308, 1995.

Keydar et al., "Properties of retrovirus–like particles produced by a human breast carcinoma cell line: Immunological relationship with mouse mammary tumor virus proteins," *Proc. Natl. Acad. Sci.* USA 81:4188–92, 1984.

Leib–Mösch and Seifarth, "Evolution and Biological Significance of Human Retroelements," *Virus Genes 11*(2/3):133–145, 1996.

Leib–Mösch et al., "Endogenous Retroviral Elements in Human DNA," *Cancer Research 50*:5636s–5642s, 1994.

Leib–Mösch et al., "Gemomic Distribution and Transcription of Solitary HERV–K LTRs," *Genomics 18*:261–269, 1993.

Liang et al., "Differential Display of Eukaryotic Messenger RNA by Means of the Polymerase Chain Reaction," *Science 257*:967–971, 1992.

Wang et al., "Detection of Mammary Tumor Virus ENV Gene–like Sequences in Human Breast Cancer," *Cancer Research 55*:5173–5179, 1995.

Watson and Fleming, "Isolation of Differentially Expressed Sequence Tags from Human Breast Cancer," *Cancer Research 54*(17):4598–4602, 1994.

Werner et al., "S71 Is a Phylogentically Distinct Human Endogenous Retroviral Element with Structural and Sequence Homology to Simian Sarcoma Virus (SSV)," *Virology 174*:225–238, 1990.

Yoshioka et al., "Pro–α1(XI) Collagen. Structure Of The Amino–Terminal Propeptide And Expression Of The Gene In Tumor Cells Lines," *J. Biol. Chem. 265*(11):6423–6426, 1990.

* cited by examiner

NUCLEOTIDE SEQUENCE OF THE REPRESENTATIVE BREAST-TUMOR SPECIFIC cDNA B18Ag1

| | | | | | | | | | | | | | | | | |
|---|---|---|---|---|---|---|---|---|---|---|---|---|---|---|---|---|
| TTA | GAG | ACC | CAA | TTG | GGA | CCT | AAT | TGG | GAC | CCA | AAT | TTC | TCA | AGT | GGA | 48 |
| Leu | Glu | Thr | Gln | Leu | Gly | Pro | Asn | Trp | Asp | Pro | Asn | Phe | Ser | Ser | Gly | |
| 1 | | | | 5 | | | | | 10 | | | | | | 15 | |

| | | | | | | | | | | | | | | | | |
|---|---|---|---|---|---|---|---|---|---|---|---|---|---|---|---|---|
| GGG | AGA | ACT | TTT | GAC | GAT | TTC | CAC | CGG | TAT | CTC | CTC | GTG | GGT | ATT | CAG | 96 |
| Gly | Arg | Thr | Phe | Asp | Asp | Phe | His | Arg | Tyr | Leu | Leu | Val | Gly | Ile | Gln | |
| | | | | 20 | | | | | 25 | | | | | 30 | | |

| | | | | | | | | | | | | | | | | |
|---|---|---|---|---|---|---|---|---|---|---|---|---|---|---|---|---|
| GGA | GCT | GCC | CAG | AAA | CCT | ATA | AAC | TTG | TCT | AAG | GCG | ATT | GAA | GTC | GTC | 144 |
| Gly | Ala | Ala | Gln | Lys | Pro | Ile | Asn | Leu | Ser | Lys | Ala | Ile | Glu | Val | Val | |
| | | | 35 | | | | | 40 | | | | | 45 | | | |

| | | | | | | | | | | | | | | | | |
|---|---|---|---|---|---|---|---|---|---|---|---|---|---|---|---|---|
| CAG | GGG | CAT | GAT | GAG | TCA | CCA | GGA | GTG | TTT | TTA | GAG | CAC | CTC | CAG | GAG | 192 |
| Gln | Gly | His | Asp | Glu | Ser | Pro | Gly | Val | Phe | Leu | Glu | His | Leu | Gln | Glu | |
| | | 50 | | | | | 55 | | | | | 60 | | | | |

| | | | | | | | | | | | | | | | | |
|---|---|---|---|---|---|---|---|---|---|---|---|---|---|---|---|---|
| GCT | TAT | CGG | ATT | TAC | ACC | CCT | TTT | GAC | CTG | GCA | GCC | CCC | GAA | AAT | AGC | 240 |
| Ala | Tyr | Arg | Ile | Tyr | Thr | Pro | Phe | Asp | Leu | Ala | Ala | Pro | Glu | Asn | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CAT | GCT | CTT | AAT | TTG | GCA | TTT | GTG | GCT | CAG | GCA | GCC | CCA | GAT | AGT | AAA | 288 |
| His | Ala | Leu | Asn | Leu | Ala | Phe | Val | Ala | Gln | Ala | Ala | Pro | Asp | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| AGG | AAA | CTC | CAA | AAA | CTA | GAG | GGA | TTT | TGC | TGG | AAT | GAA | TAC | CAG | TCA | 336 |
| Arg | Lys | Leu | Gln | Lys | Leu | Glu | Gly | Phe | Cys | Trp | Asn | Glu | Tyr | Gln | Ser | |
| | | | 100 | | | | | 105 | | | | | 110 | | | |

| | | | | | | | | |
|---|---|---|---|---|---|---|---|---|
| GCT | TTT | AGA | GAT | AGC | CTA | AAA | GGT | TTT | 363 |
| Ala | Phe | Arg | Asp | Ser | Leu | Lys | Gly | Phe | |
| | | 115 | | | | | 120 | | |

*Fig. 6*

NUCLEOTIDE SEQUCNE OF THE REPRESENTATIVE
BREAST-TUMOR SPECIFIC cDNA B17Ag1

| | | | | | |
|---|---|---|---|---|---|
| GC | TGGGCACAGT | GGCTCATACC | TGTAATCCTG | ACCGTTTCAG | AGGCTCAGGT | 60 |
| CG | CTTGAGCCCA | AGATTTCAAG | ACTAGTCTGG | GTAACATAGT | GAGACCCTAT | 120 |
| AA | AAATAAAAAA | ATGAGCCTGG | TGTAGTGGCA | CACACCAGCT | GAGGAGGGAG | 180 |
| CT | AGGAGA | | | | | 196 |

Fig. 7

NUCLEOTIDE SEQUENCE OF THE REPRESENTATIVE
BREAST-TUMOR SPECIFIC cDNA B17Ag2

| | | | | | |
|---|---|---|---|---|---|
| GC | TTGGGGGCTC | TGACTAGAAA | TTCAAGGAAC | CTGGGATTCA | AGTCCAACTG | 60 |
| AC | TTACACTGTG | GNCTCCAATA | AACTGCTTCT | TTCCTATTCC | CTCTCTATTA | 120 |
| AA | GGAAAACGAT | GTCTGTGTAT | AGCCAAGTCA | GNTATCCTAA | AAGGAGATAC | 180 |
| AT | TAAATATCAG | AATGTAAAAC | CTGGGAACCA | GGTTCCCAGC | CTGGGATTAA | 240 |
| CA | AGAAGACTGA | ACAGTACTAC | TGTGAAAAGC | CCGAAGNGGC | AATATGTTCA | 300 |
| TT | GAAGGATGGC | TGGGAGAATG | AATGCTCTGT | CCCCCAGTCC | CAAGCTCACT | 360 |
| CT | CCTTTATAGC | CTAGGAGA | | | | 388 |

Fig. 8

NUCLEOTIDE SEQUENCE OF THE REPRESENTATIVE
BREAST-TUMOR SPECIFIC cDNA B13Ag2a

| | | | | | |
|---|---|---|---|---|---|
| GC | CTATAATCAT | GTTTCTCATT | ATTTTCACAT | TTTATTAACC | AATTTCTGTT | 60 |
| AA | AATATGAGGG | AAATATATGA | AACAGGGAGG | CAATGTTCAG | ATAATTGATC | 120 |
| TG | ATTTCTACAT | CAGATGCTCT | TTCCTTTCCT | GTTTATTTCC | TTTTTATTTC | 180 |
| GG | TCGAATGTAA | TAGCTTTGTT | TCAAGAGAGA | GTTTTGGCAG | TTTCTGTAGC | 240 |
| CT | GCTCATGTCT | CCAGGCATCT | ATTTGCACTT | TAGGAGGTGT | CGTGGGAGAC | 300 |
| CT | ATTTTTTCCA | TATTTGGGCA | ACTACTA | | | 337 |

*Fig. 9*

NUCLEOTIDE SEQUENCE OF THE REPRESENTATIVE
BREAST-TUMOR SPECIFIC cDNA B13Ag1b

| | | | | | |
|---|---|---|---|---|---|
| GC | CATACAGTGC | CTTTCCATTT | ATTTAACCCC | CACCTGAACG | GCATAAACTG | 60 |
| GC | TGGTGTTTTT | TACTGTAAAC | AATAAGGAGA | CTTTGCTCTT | CATTTAAACC | 120 |
| AT | TTCATATTTT | ACGCTCGAGG | GTTTTTACCG | GTTCCTTTTT | ACACTCCTTA | 180 |
| TT | TAAGTCGTTT | GGAACAAGAT | ATTTTTTCTT | TCCTGGCAGC | TTTTAACATT | 240 |
| TT | TGTGTCTGGG | GGACTGCTGG | TCACTGTTTC | TCACAGTTGC | AAATCAAGGC | 300 |
| CC | AAGAAAAAAA | AATTTTTTTG | TTTTATTTGA | AACTGGACCG | GATAAACGGT | 360 |
| CG | GCTGCTGTAT | ATAGTTTTAA | ATGGTTTATT | GCACCTCCTT | AAGTTGCACT | 420 |
| GG | GGGGNTTTTG | NATAGAAAGT | NTTTANTCAC | ANAGTCACAG | GGACTTTTNT | 480 |
| NA | CTGAGCTAAA | AAGGGCTGNT | TTTCGGGTGG | GGGCAGATGA | AGGCTCACAG | 540 |
| TC | TCTTAGAGGG | GGGAACTNCT | A | | | 571 |

Fig. 10

NUCLEOTIDE SEQUENCE OF THE REPRESENTATIVE BREAST-TUMOR SPECIFIC cDNA B13Ag1a

```
TA ATAACTTAAA TATATTTTGA TCACCCACTG GGGTGATAAG ACAATAGATA      60

TT TCCAAAAAGC ATAAAACCAA AGTATCATAC CAAACCAAAT TCATACTGCT     120

CC GCACTGAAAC TTCACCTTCT AACTGTCTAC CTAACCAAAT TCTACCCTTC     180

GG TGCGTGCTCA CTACTCTTTT TTTTTTTTT TTTNTTTTGG AGATGGAGTC      240

CA GCCCAGGGGT GGAGTACAAT GGCACAACCT CAGCTCACTG NAACCTCCGC     300

TT CATGAGATTC TCCTGNTTCA GCCTTCCCAG TAGCTGGGAC TACAGGTGTG     360

TG CCTGGNTAAT CTTTTTTNGT TTTNGGGTAG AGATGGGGGT TTTACATGTT     420

TG GTNTCGAACT CCTGACCTCA AGTGATCCAC CCACCTCAGG CTCCCAAAGT     480

TA CAGACATGAG CCACTGNGCC CAGNCCTGGT GCATGCTCAC TTCTCTAGGC     540

NUCLEOTIDE SEQUENCE OF THE REPRESENTATIVE BREAST-TUMOR SPECIFIC cDNA B11Ag1

```
TG CACATGCAGA ATATTCTATC GGTACTTCAG CTATTACTCA TTTTGATGGC      60

AG CCTATCCTCA AGATGAGTAT TTAGAAAGAA TTGATTTAGC GATAGACCAA     120

GC ACTCTGACTA CACGAAATTG TTCAGATGTG ATGGATTTAT GACAGTTGAT     180

GA GATTATTAAG TGATTATTTT AAAGGGAATC CATTAATTCC AGAATATCTT     240

TC AAGATGATAT AGAAATAGAA CAGAAAGAGA CTACAAATGA AGATGTATCA     300

TA TTGAAGAGCC TATAGTAGAA AATGAATTAG CTGCATTTAT TAGCCTTACA     360

TT TTCCTGATGA ATCTTATATT CAGCCATCGA CATAGCATTA CCTGATGGGC     420

GA ATAATAGAAA CTGGGTGCGG GGCTATTGAT GAATTCATCC NCAGTAAATT     480

AC AAAATATAAC TCGATTGCAT TTGGATGATG GAATACTAAA TCTGGCAAAA     540

GG AGCTACTAGT AACCTCTCTT TTTGAGATGC AAAATTTTCT TTAGGGTTT     600

CT ACTTTACGGA TATTGGAGCA TAACGGGA                             638
```

*Fig. 12*

NUCLEOTIDE SEQUENCE OF THE REPRESENTATIVE
BREAST-TUMOR SPECIFIC cDNA B3CA3c

```
ACTGATGGAT GTCGCCGGAG GCGAGGGGCC TTATCTGATG CTCGGCTGCC TGTTCGTGAT    60
GTGCGCGGCG ATTGGGCTGT TTATCTCAAA CACCGCCACG GCGGTGCTGA TGGCGCCTAT   120
TGCCTTAGCG GCGGCGAAGT CAATGGGCGT CTCACCCTAT CCTTTTGCCA TGGTGGTGGC   180
GATGGCGGCT TCGGCGGCGT TTATGACCCC GGTCTCCTCG CCGGTTAACA CCCTGGTGCT   240
TGGCCCTGGC AAGTACTCAT TTAGCGATTT TGTCAAAATA GGCGTG                  286
```

Fig. 13

NUCLEOTIDE SEQUENCE OF THE REPRESENTATIVE
BREAST-TUMOR SPECIFIC cDNA B9CG1

| | | | | | |
|---|---|---|---|---|---|
| AG | CAGCCCCTTC | TTCTCAATTT | CATCTGTCAC | TACCCTGGTG | TAGTATCTCA | 60 |
| CA | TTTTTATAGC | CTCCTCCCTG | GTCTGTCTTT | TGATTTTCCT | GCCTGTAATC | 120 |
| AC | ATAACTGCAA | GTAAACATTT | CTAAAGTGTG | GTTATGCTCA | TGTCACTCCT | 180 |
| AA | ATAGTTTCCA | TTACCGTCTT | AATAAAATTC | GGATTTGTTC | TTTNCTATTN | 240 |
| CA | CCTATGACCG | AA | | | | 262 |

*Fig. 14*

NUCLEOTIDE SEQUENCE OF THE REPRESENTATIVE
BREAST-TUMOR SPECIFIC cDNA B9CG3

| | | | | |
|---|---|---|---|---|
| AG CAAAGCCAGT | GGTTTGAGCT | CTCTACTGTG | TAAACTCCTA | AACCAAGGCC | 60 |
| TA AATGGTGGCA | GGATTTTTAT | TATAAACATG | TACCCATGCA | AATTTCCTAT | 120 |
| GA TATATTCTTC | TACATTTAAA | CAATAAAAAT | AATCTATTTT | TAAAAGCCTA | 180 |
| AG TTAGGTAAGA | GTGTTTAATG | AGAGGGTATA | AGGTATAAAT | CACCAGTCAA | 240 |
| TG CCTATGACCG | A | | | | 261 |

*Fig. 15*

NUCLEOTIDE SEQUENCE OF THE REPRESENTATIVE
BREAST-TUMOR SPECIFIC cDNA B2CA2

```
GG GCATGGACGC AGACGCCTGA CGTTTGGCTG AAAATCTTTC ATTGATTCGT      60

AT AGGAAAATTC CCAAAGAGGG AATGTCCTGT TGCTCGCCAG TTTTTNTGTT     120

GG ANAAGGCAAN GAGCTCTTCA GACTATTGGN ATTNTCGTTC GGTCTTCTGC     180

CG NCTTGCNANG ATCTTCAT                                        208
```

*Fig. 16*

NUCLEOTIDE SEQUENCE OF THE REPRESENTATIVE
BREAST-TUMOR SPECIFIC cDNA B3CA1

```
GG GCATGGACGC AGACGCCTGA CGTTTGGCTG AAAATCTTTC ATTGATTCGT      60

AT AGGAAAATTC CCAAAGAGGG AATGTCCTGT TGCTCGCCAG TTTTTNTGTT     120

GG ANAAGGCAAN GAGCTCTTCA GACTATTGGN ATTNTCGTTC GGTCTTCTGC     180

CG NCTTGCNANG ATCTTCAT                                        208
```

Fig. 17

NUCLEOTIDE SEQUENCE OF THE REPRESENTATIVE
BREAST-TUMOR SPECIFIC cDNA B3CA2

| | | | | | |
|---|---|---|---|---|---|
| GG | GCATGGACGC | AGACGCCTGA | CGTTTGGCTG | AAAATCTTTC | ATTGATTCGT | 60 |
| AT | AGGAAAATTC | CCAAAGAGGG | AATGTCCTGT | TGCTCGCCAG | TTTTTNTGTT | 120 |
| GG | ANAAGGCAAN | GAGCTCTTCA | GACTATTGGN | ATTNTCGTTC | GGTCTTCTGC | 180 |
| CG | NCTTGCNANG | ATCTTCAT | | | | 208 |

Fig. 18

NUCLEOTIDE SEQUENCE OF THE REPRESENTATIVE
BREAST-TUMOR SPECIFIC cDNA B3CA3

```
AG GGAGCAAGGA GAAGGCATGG AGAGGCTCAN GCTGGTCCTG GCCTACGACT      60

CT GTCGCCGGGG ATGGTGGAGA ACTGAAGCGG GACCTCCTCG AGGTCCTCCG     120

TC NCCGTCCAGG AGGAGGGTCT TTCCGTGGTC TNGGAGGAGC GGGGGGAGAA     180

TC ATGGTCNACA TCCC                                            204
```

Fig. 19

NUCLEOTIDE SEQUENCE OF THE REPRESENTATIVE
BREAST-TUMOR SPECIFIC cDNA B4CA1

| | | | | | |
|---|---|---|---|---|---|
| TC | AGGAGCGGGT | AGAGTGGCAC | CATTGAGGGG | ATATTCAAAA | ATATTATTTT | 60 |
| TG | ATAGTTGCTG | AGTTTTTCTT | TGACCCATGA | GTTATATTGG | AGTTTATTTT | 120 |
| CC | AATCGCATGG | ACATGTTAGA | CTTATTTTCT | GTTAATGATT | NCTATTTTTA | 180 |
| GA | TTTGAGAAAT | TGGTTNTTAT | TATATCAATT | TTTGGTATTT | GTTGAGTTTG | 240 |
| GC | TTAGTATGTG | ACCA | | | | 264 |

*Fig. 20* ns and methods for the treatment and diagnosis of breast cancer

COMPOSITIONS AND METHODS FOR THE TREATMENT AND DIAGNOSIS OF BREAST CANCER

CROSS-REFERENCE TO RELATED APPLICATIONS

This application is a divisional of U.S. patent application Ser. No. 08/838,762, filed Apr. 9, 1997 abandoned, which is a 371 and claims priority to International Patent Application No. PCT/US97/00485, filed Jan. 10, 1997. U.S. patent application Ser. No. 08/838,762, filed Apr. 9, 1997, is a CIP of U.S. patent application Ser. No. 08/700,014, filed Aug. 20, 1996, abandoned which is a CIP of U.S. patent application Ser. No. 08/585,392, filed Jan. 1, 1996 abandoned.

TECHNICAL FIELD

The present invention relates generally to the detection and therapy of breast cancer. The invention is more specifically related to nucleotide sequences that are, preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated DNA molecules are provided, comprising (a) a nucleotide sequence preferentially expressed in breast cancer tissue, relative to normal tissue; (b) a variant of such a sequence that contains one or more nucleotide substitutions, deletions, insertions and/or modifications at no more than 20% (preferably no more than 5%) of the nucleotide positions, such that the antigenic and/or immunogenic properties of the polypeptide encoded by the nucleotide sequence are retained; or (c) a nucleotide sequence encoding an epitope of a polypeptide encoded by at least one of the above sequences. In one embodiment, the isolated DNA molecule comprises a human endogenous retroviral sequence recited in SEQ ID NO:1. In other embodiments, the isolated DNA molecule comprises a nucleotide sequence recited in any one of SEQ ID NO: 3–77, 142, 143, 146–152, 154–166, 168–176, 178–192, 194–198, 200–204, 206, 207, 209–214, 216, 218, 219, 221–240, 243–245 and 247.

In related embodiments, the isolated DNA molecule encodes an epitope of a polypeptide, wherein the polypeptide is encoded by a nucleotide sequence that: (a) hybridizes to a sequence recited in any one of SEQ ID NO: 1, 3–77, 142, 143, 146–152, 154–166, 168–176, 178–192, 194–198, 200–204, 206, 207, 209–214, 216, 218, 219, 221–240, 243–245 and 247 under stringent conditions; and (b) is at least 80% identical to a sequence recited in any one of SEQ ID NO: 1, 3–77, 142, 143, 146–152, 154–166, 168–176, 178–192, 194–198, 200–204, 206, 207, 209–214, 216, 218, 219, 221–240, 243–245 and 247; and wherein RNA corresponding to said nucleotide sequence is expressed at a greater level in human breast tumor tissue than in normal breast tissue.

In another embodiment, the present invention provides an isolated DNA molecule encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions, deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a DNA molecule as described above are also provided.

In related aspects, the present invention provides recombinant expression vectors comprising a DNA molecule as described above and host cells transformed or transfected with such expression vectors.

In further aspects, polypeptides, comprising an amino acid sequence encoded by a DNA molecule as described above, and monoclonal antibodies that bind to such polypeptides are provided.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, and a detection reagent.

Within a related aspect, the diagnostic kit comprises a first polymerase chain reaction primer and a second polymerase chain reaction primer, at least one of the primers being specific for an RNA molecule described herein. In one embodiment, at least one of the primers comprises at least about 10 contiguous nucleotides of an RNA molecule as described above, or an RNA molecule encoding a polypeptide encoded by a nucleotide sequence selected from the group consisting of SEQ ID NO: 78–86, 144, 145, 153, 167, 177, 193, 199, 205, 208, 215, 217, 220, 241, 242 and 246.

Within another related aspect, the diagnostic kit comprises at least one oligonucleotide probe, the probe being specific for a DNA molecule described herein. In one embodiment, the probe comprises at least about 15 contiguous nucleotides of a DNA molecule as described above, or a DNA molecule selected from the group consisting of SEQ ID NO: 78–86, 144, 145, 153, 167, 177, 193, 199, 205, 208, 215, 217, 220, 241, 242 and 246.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected form the group consisting of SEQ ID NO: 78–86, 144, 145, 153, 167, 177, 193, 199, 205, 208, 215, 217, 220, 241, 242, 246 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immune response enhancer or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246 and sequences that hybridize thereto under stringent conditions.

In related aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6 shows the nucleotide sequence of the representative breast tumor-specific cDNA B18Ag1.

FIG. 7 shows the nucleotide sequence of the representative breast tumor-specific cDNA B17Ag1.

FIG. 8 shows the nucleotide sequence of the representative breast tumor-specific cDNA B17Ag2.

FIG. 9 shows the nucleotide sequence of the representative breast tumor-specific cDNA B13Ag2a.

FIG. 10 shows the nucleotide sequence of the representative breast tumor-specific cDNA B13Ag1b.

FIG. 11 shows the nucleotide sequence of the representative breast tumor-specific cDNA B13Ag1a.

FIG. 12 shows the nucleotide sequence of the representative breast tumor-specific cDNA B11Ag1.

FIG. 13 shows the nucleotide sequence of the representative breast tumor-specific cDNA B3CA3c.

FIG. 14 shows the nucleotide sequence of the representative breast tumor-specific cDNA B9CG1.

FIG. 15 shows the nucleotide sequence of the representative breast tumor-specific cDNA B9CG3.

FIG. 16 shows the nucleotide sequence of the representative breast tumor-specific cDNA B2CA2.

FIG. 17 shows the nucleotide sequence of the representative breast tumor-specific cDNA B3CA1.

FIG. 18 shows the nucleotide sequence of the representative breast tumor-specific cDNA B3CA2.

FIG. 19 shows the nucleotide sequence of the representative breast tumor-specific cDNA B3CA3.

FIG. 20 shows the nucleotide sequence of the representative breast tumor-specific cDNA B4CA1.

DETAILED DESCRIPTION OF THE INVENTION

Figure 1:
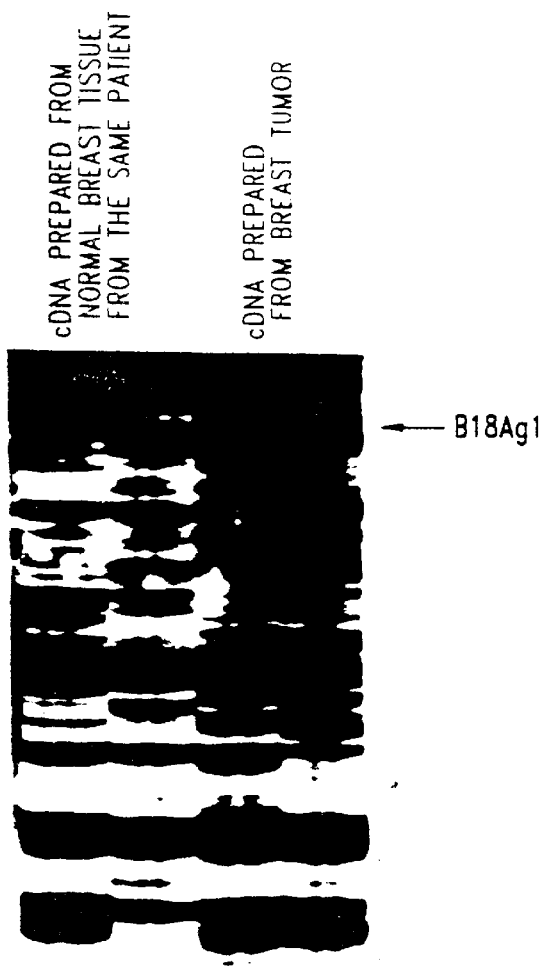
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, nucleic acid sequences and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Nucleic acid sequences of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO:1). Also within the scope of the present invention are polypeptides encoded by other sequences within the retroviral genome containing B18Ag1 (SEQ ID NO: 141). Such sequences include, but are not limited to, the sequences recited in SEQ ID NO:3–SEQ ID NO:10. B18Ag1 has homology to the gag p30 gene of the endogenous human retroviral element S71, as described in Werner et al., *Virology* 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–77, 142, 143, 146–152, 154–166, 168–176, 178–192, 194–198, 200–204, 206, 207, 209–214, 216, 218, 219, 221–240, 243–245 and 247. As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g. in an ELISA and/or T-cell reactivity assay). Such screens may generally be performed using methods well known to those of ordinary skill in the art, such as those described in Harlow and Lane, *Antibodies: A Laboratory Manual,* Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The compositions and methods of the present invention also encompass variants of the above polypeptides and nucleic acid sequences encoding such polypeptides. A polypeptide "variant," as used herein, is a polypeptide that differs from the native polypeptide in substitutions and/or modifications, such that the antigenic and/or immunogenic properties of the polypeptide are retained. Such variants may generally be identified by modifying one of the above polypeptide sequences and evaluating the reactivity of the modified polypeptide with antisera and/or T-cells as described above. Nucleic acid variants may contain one or more substitutions, deletions, insertions and/or modifications such that the antigenic and/or immunogenic properties of the encoded polypeptide are retained. One preferred variant of the polypeptides described herein is a variant that contains nucleotide substitutions, deletions, insertions and/ or modifications at no more than 20% of the nucleotide positions.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic or antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, nucleotide sequences encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA. using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Nucleotide sequences encoding all or a portion of the breast tumor-specific polypeptides disclosed herein may be amplified from cDNA prepared as described above using the random primers shown in SEQ ID NO.:87–125.

Alternatively, a gene encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO:1, and may be purchased or synthesized. One suitable primer pair for amplification from breast tumor cDNA is (5'ATG GCT ATT TTC GGG GGC TGA CA) (SEQ ID NO.:126) and (5'CCG GTA TCT CCT CGT GGG TAT T) (SEQ ID NO.:127). An amplified portion of B18Ag1 may then be used to isolate the full length gene from a human genomic DNA library or from a breast tumor cDNA library, using well known techniques, such as those described in Sambrook et al., Molecular Cloning: A Laboratory Manual, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO:11–SEQ ID NO:86 and SEQ ID NO:142–SEQ ID NO:247.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149–2146 (1963). Equipment for automated synthesis of polypeptides is commercially available from suppliers such as Perkin Elmer/Applied BioSystems Division,, Foster City, Calif., and may be operated according to the manufacturer's instructions.

In specific embodiments, polypeptides of the present invention encompass amino acid sequences encoded by a DNA molecule having a sequence recited in any one of SEQ ID NO:1, 3–77, 142, 143, 146–152, 154–166, 168–176, 178–192, 194–198, 200–204, 206, 207, 209–214, 216, 218, 219, 221–240, 243–245 and 247, variants of such polypeptides that are encoded by DNA molecules containing one or more nucleotide substitutions, deletions, insertions and/or modifications at no more than 20% of the nucleotide positions, and epitopes of the above polypeptides. Polypeptides within the scope of the present invention also include polypeptides (and epitopes thereof) encoded by DNA sequences that hybridize to a DNA molecule having a sequence recited in any one of SEQ ID NO:1, 3–77, 142, 143, 146–152, 154–166, 168–176, 178–192, 194–198, 200–204, 206, 207, 209–214, 216, 218, 219, 221–240, 243–245 and 247 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. DNA molecules according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, Antibodies: A Laboratory Manual, Cold Spring Harbor Laboratory, 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, Eur. J. Immunol. 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual,* Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the tern "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 $\mu$g, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0. 1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 1 $\mu$g. Such tests can typically be performed with a very small amount of biological sample.

The presence or absence of breast cancer in a patient may also be determined by evaluating the level of MRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify sequences from cDNA prepared from RNA that is isolated from one of the above biological samples. Sequence-specific primers for use in such amplification may be designed based on the sequences provided in any one of SEQ ID NO: 1, 11–86 and 142–247, and may be purchased or synthesized. In the case of B18Ag1, as noted herein, one suitable primer pair is B18Ag1-2 (5'ATG GCT ATT TTC GGG GGC TGA CA) (SEQ ID NO.:126) and B18Ag1-3 (5'C.CG GTA TCT CCT CGT GGG TAT T) (SEQ ID NO.:127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of cDNA spanning two orders of magnitude. A two-fold or greater increase in expression in several dilutions of the tumor sample as compared to the same dilution of the non-tumor sample is considered positive.

As used herein, the term "primer/probe specific for a DNA/RNA molecule" means an oligonucleotide sequence that has at least about 80% identity, preferably at least about 90% and more preferably at least about 95%, identity to the DNA/RNA molecule in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a DNA/RNA molecule encoding one of the polypeptides disclosed herein. Preferably, oligonucleotide probes for use in the inventive diagnostic methods comprise at least about 15 contiguous oligonucleotides of a DNA/RNA molecule encoding one of the polypeptides disclosed herein. Techniques for both PCR based assays and in situ hybridization assays are well known in the art.

Conventional RT-PCR protocols using agarose and ethidium bromide staining while important in defining gene specificity do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. AS used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to. a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 μg to 100 μg, preferably from about 10 μg to 50 μg in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or nucleic acid molecules) are preferably incorporated into pharmaceutical compositions or vaccines. Pharmaceutical compositions comprise one or more such compounds and a physiologically acceptable carrier. Vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, including one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745–1749 (1993), and reviewed by Cohen, Science 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The above pharmaceutical compositions and vaccines may be used, for example, for the therapy of breast cancer in a patient. As used herein, a "patient"refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. To prevent the development of breast cancer, a pharmaceutical composition or vaccine comprising one or more polypeptides as described herein may be administered to a patient. Alternatively, naked DNA or plasmid or viral vector encoding the polypeptide, may be administered. For treating a patient with breast cancer, the pharmaceutical composition or vaccine may comprise one or more polypeptides, antibodies or nucleotide sequences complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

The following Examples are offered by way of illustration and not by way of limitation.

EXAMPLES

Example 1

Preparation of Breast Tumor-Specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO.:130) anchored 3' primer. Differential display PCR was then executed using a randomly chosen primer (CTTCAACCTC) (SEQ ID NO.:103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C. extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B18Ag1 fragment initially cloned is 77% identical to the endogenous human retroviral element S71, which is a truncated retroviral element homologous to the Simian Sarcoma Virus (SSV). S71 contains an incomplete gag gene, a portion of the pol gene and an LTR-like structure at the 3' terminus (see Werner et al., *Virology* 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO.:128) and B18Ag1-4 (CCG GAG GAG GAA GCT AGA GGA ATA) (SEQ ID NO.:129) at a 3.5 mM magnesium concentration and a pH of 8.5, and B18Ag1-2 (ATG GCT ATT TTC GGG GCC TGA CA) (SEQ ID NO.:126) and B18Ag1-3 (CCG GTA TCT CCT CGT GGG TAT T) (SEQ ID NO.:127) at 2 mM magnesium at pH 9.5. The same experiments showed exceedingly low to nonexistent levels of expression in this patient's normal breast tissue (see FIG. 1). RT-PCR experiments were then used to show that B18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
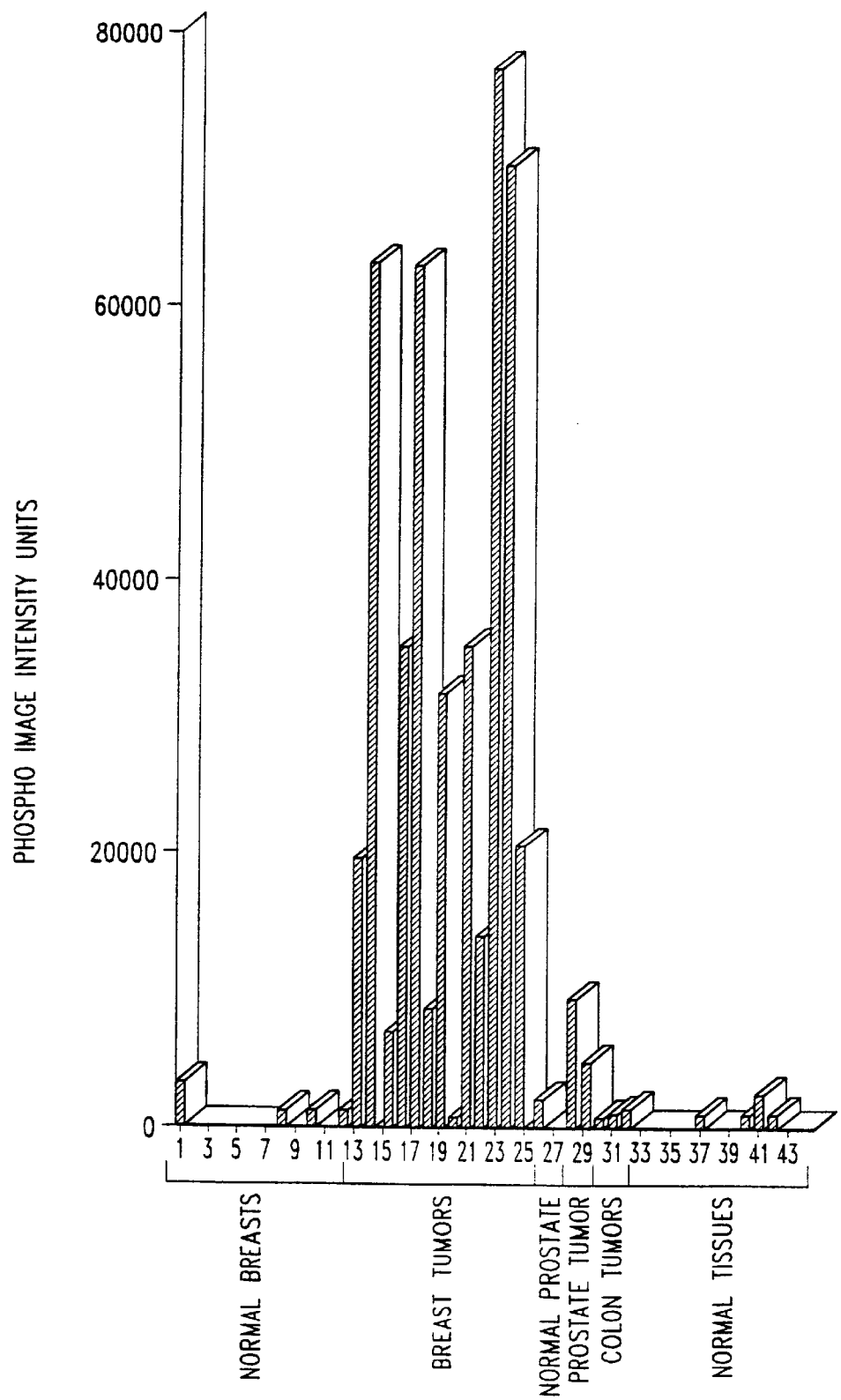
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known β-actin message abundance in each assay and normalizing the results of the different assays with respect to this positive control.

Figure 4:
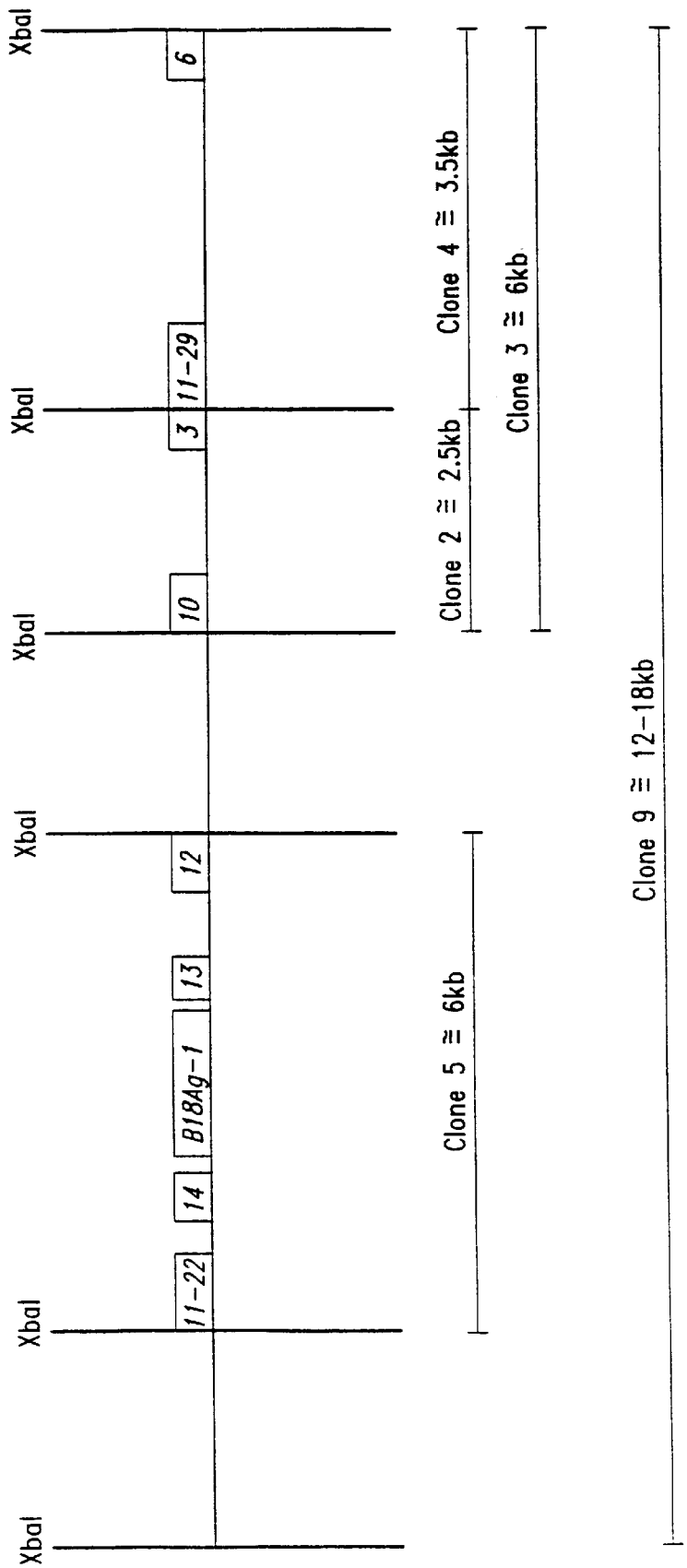
FIG. 4 is a genomic clone map showing the location of additional retroviral sequences obtained from ends of XbaI restriction digests (provided in SEQ ID NO:3–SEQ ID NO:10) relative to B18Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3–SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO:10 shows the location of the sequence labeled 11–22.

Figures 5A, 5B:
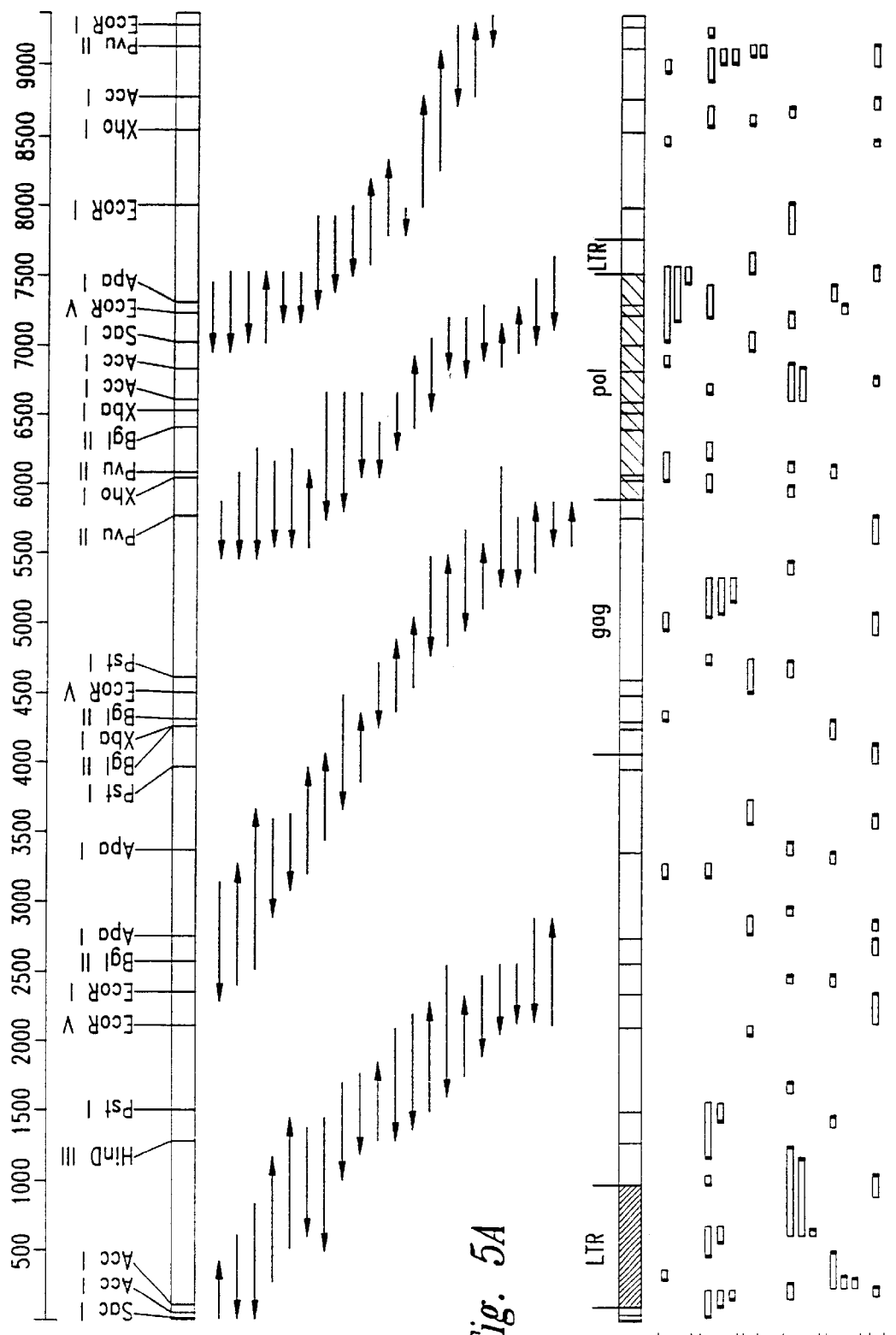
FIGS. 5A and 5B show the sequencing strategy, genomic organization and predicted open reading frame for the retroviral element containing B18Ag1.
Figure 21A:
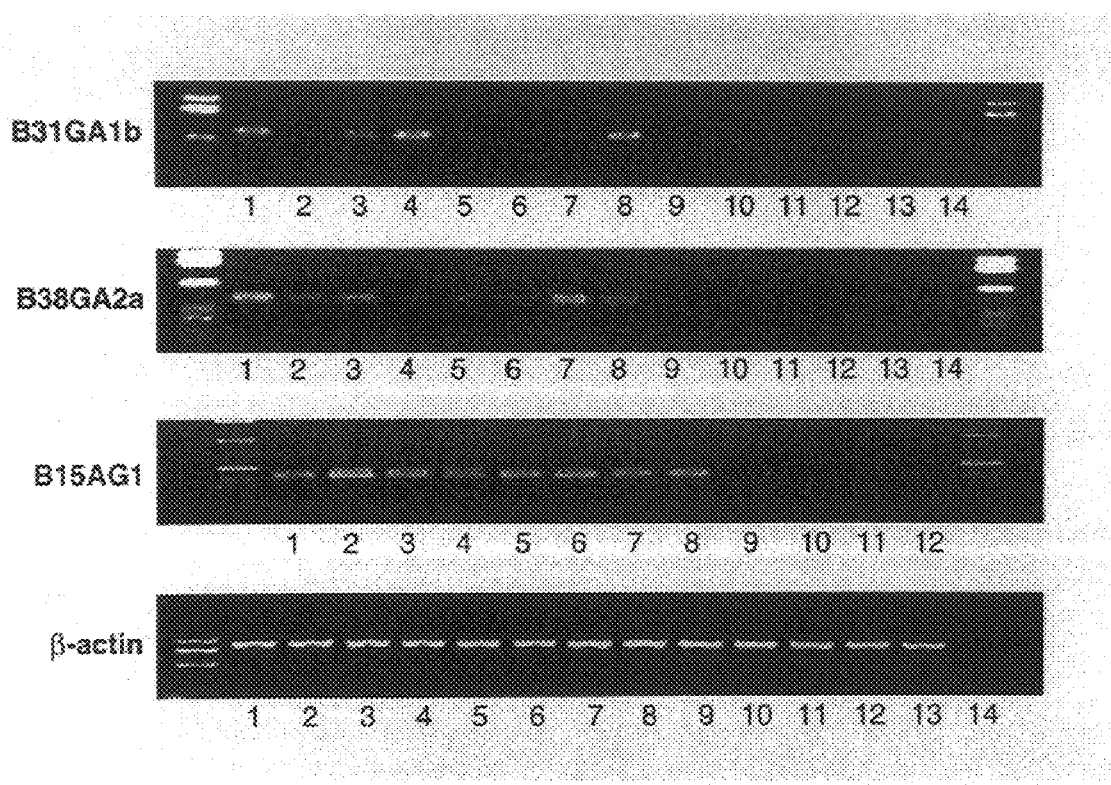
FIG. 21A depicts RT-PCR analysis of breast tumor genes in breast tumor tissues (lanes 1–8) and normal breast tissues (lanes 9–13) and H$_2$O (lane 14).
Figure 21B:
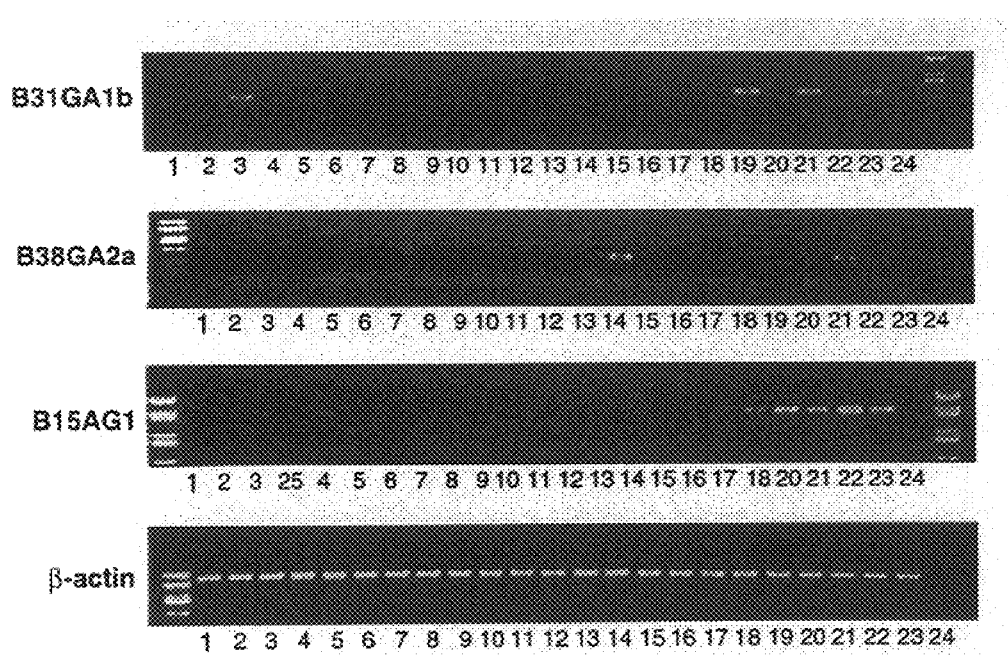
FIG. 21B depicts RT-PCR analysis of breast tunor genes in prostate tumors (lane 1,2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), $H_2O$ (lane 24), and colon tumor (lane 25).

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO:1 as a probe, a longer cDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypetides Normal RNA and tumor RNA was prepared and mRNA was isolated and converted into EDNA using a $(dT)_{12}AG$ anchored 3' primer, as described above. Differential display PCR was then executed using the randomly chosen primers SEQ ID NO.: 87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NO.:11–77) (see also FIGS. 6–20). Subsequent studies identified an additional 104 sequences (SEQ ID NOS:142–247), of which 89 appeared to be novel (SEQ ID NOS:142, 143, 146–152, 154–166, 168–176, 178–192, 194–198, 200–204, 206, 207, 209–214, 216, 218, 219, 221–240, 243–245 and 247). To the best of the inventors' knowledge none of the previously identified sequences have heretofore been shown to be expressed at a greater level in human breast tumor tissue than in normal breast tissue.

Example 2 preparation of B18Ag1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B18Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B18Ag1 DNA from Breast Tumor cDNA

This Example illustrates the preparation of B18Ag1 DNA by amplification from human breast tumor CDNA.

First strand cDNA is synthesized from RNA prepared from human breast tumor tissue in a reaction mixture containing 500 ng poly A+RNA, 200 pmol of the primer $(T)_{12}AG$ (i.e., TTT TTT TTT TTT AG) (SEQ ID NO: 130), 1× first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 µl. After first strand synthesis, the cDNA is diluted approximately 25 fold and 1 µl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-cell and T-cell Epitopes of B18Ag1

This Example illustrates the identification of B18Ag1 epitopes.

The B18Ag1 sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med.* 164:1779–84 (1986) or Spouge et al., *J. Immunol* 138:204–12 (1987). Additional Class II MHC (antibody or B-cell) epitopes can be predicted using programs such as AMPHI (e.g., Margalit et al., *J. Immunol.* 138:2213 (1987)) or the methods of Rothbard and Taylor (e.g., *EMBO J.* 7:93 (1988)).

Once peptides (15–20 amino acids long) are identified using these techniques, individual peptides can be synthesized using automated peptide synthesis equipment (available from manufacturers such as Perkin Elmer/Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8–10 amino acid motifs within the B18Ag1 sequence which are capable of binding to HLA Class I MHC molecules. (see, e.g., Rammensee et al., *Immunogenetics* 41:178–228 (1995)). Following synthesis such peptides can be tested for their ability to bind to class I MHC using standard binding assays (e.g., Sette et al., *J. Immunol.* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995); Visseren et al., *J. Immunol.* 154:3991–98 (1995); Kawakami et al., *J. Immunol* 154:3961–68 (1995); and Kast et al., *J. Immunol* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J. Exp. Med.* 173:1007–15 (1991).

A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)

SSGGRTFDDFHRYLLVGI
QGAAQKPINLSKXIEWQGHDE
SPGVFLEHLQEAYRIYTPFDLSA

Predicted HLA A2.1 Motifs (T-cell epitopes) (SEQ ID NOS.: 134–140)

YLLVGIQGA
GAAQKPINL
NLSKXIEVV
EVVQGHDES
HLQEAYRIY
NLAFVAQAA
FVAQAAPDS

Example 5

Characterization of Breast Tumor Genes Discovered by Differential Display PCR The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Using gene specific primers, the MRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO. 157). Table I summarizes the expression level of all the genes tested in normal breast tissue and breast tumors, and also in other tissues.

TABLE I

| Percentage of Breast Cancer Antigens that are Expressed in Various Tissues | |
|---|---|
| Breast Tissues | |
| Over-expressed in Breast Tumors | 84% |
| Equally Expressed in Normals and Tumor | 16% |
| Other Tissues | |
| Over-expressed in Breast Tumors but not in any Normal Tissues | 9% |
| Over-expressed in Breast Tumors but Expressed in Some Normal Tissues | 30% |
| Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

```
SEQUENCE LISTING (1) GENERAL INFORMATION:

(iii) NUMBER OF SEQUENCES: 247

(2) INFORMATION FOR SEQ ID NO: 1:

(i) SEQUENCE CHARACTERISTICS:
          (A) LENGTH: 363 base pairs
          (B) TYPE: nucleic acid
          (C) STRANDEDNESS: single
          (D) TOPOLOGY: linear
```

(ix) FEATURE:
        (A) NAME/KEY: CDS
        (B) LOCATION: 1..363

(xi) SEQUENCE DESCRIPTION: SEQ ID NO: 1:

```
TTA GAG ACC CAA TTG GGA CCT AAT TGG GAC CCA AAT TTC TCA AGT GGA      48
Leu Glu Thr Gln Leu Gly Pro Asn Trp Asp Pro Asn Phe Ser Ser Gly
 1               5                  10                  15

GGG AGA ACT TTT GAC GAT TTC CAC CGG TAT CTC CTC GTG GGT ATT CAG      96
Gly Arg Thr Phe Asp Asp Phe His Arg Tyr Leu Leu Val Gly Ile Gln
                20                  25                  30

GGA GCT GCC CAG AAA CCT ATA AAC TTG TCT AAG GCG ATT GAA GTC GTC     144
Gly Ala Ala Gln Lys Pro Ile Asn Leu Ser Lys Ala Ile Glu Val Val
            35                  40                  45

CAG GGG CAT GAT GAG TCA CCA GGA GTG TTT TTA GAG CAC CTC CAG GAG     192
Gln Gly His Asp Glu Ser Pro Gly Val Phe Leu Glu His Leu Gln Glu
        50                  55                  60

GCT TAT CGG ATT TAC ACC CCT TTT GAC CTG GCA GCC CCC GAA AAT AGC     240
Ala Tyr Arg Ile Tyr Thr Pro Phe Asp Leu Ala Ala Pro Glu Asn Ser
 65                  70                  75                  80

CAT GCT CTT AAT TTG GCA TTT GTG GCT CAG GCA GCC CCA GAT AGT AAA     288
His Ala Leu Asn Leu Ala Phe Val Ala Gln Ala Ala Pro Asp Ser Lys
                85                  90                  95

AGG AAA CTC CAA AAA CTA GAG GGA TTT TGC TGG AAT GAA TAC CAG TCA     336
Arg Lys Leu Gln Lys Leu Glu Gly Phe Cys Trp Asn Glu Tyr Gln Ser
                100                 105                 110

GCT TTT AGA GAT AGC CTA AAA GGT TTT                                 363
Ala Phe Arg Asp Ser Leu Lys Gly Phe
            115                 120
```

(2) INFORMATION FOR SEQ ID NO: 2:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
                20                  25                  30

Gly Ala Ala Gln Lys Pro Ile Asn Leu Ser Lys Ala Ile Glu Val Val
            35                  40                  45

Gln Gly His Asp Glu Ser Pro Gly Val Phe Leu Glu His Leu Gln Glu
        50                  55                  60

Ala Tyr Arg Ile Tyr Thr Pro Phe Asp Leu Ala Ala Pro Glu Asn Ser
 65                  70                  75                  80

His Ala Leu Asn Leu Ala Phe Val Ala Gln Ala Ala Pro Asp Ser Lys
                85                  90                  95

Arg Lys Leu Gln Lys Leu Glu Gly Phe Cys Trp Asn Glu Tyr Gln Ser
                100                 105                 110

Ala Phe Arg Asp Ser Leu Lys Gly Phe
            115                 120
```

(2) INFORMATION FOR SEQ ID NO: 3:

(i) SEQUENCE CHARACTERISTICS:

(A) LENGTH: 1101 base pairs
(B) TYPE: nucleic acid
(C) STRANDEDNESS: single
(D) TOPOLOGY: linear (xi) SEQUENCE DESCRIPTION: SEQ ID NO: 3:

```
TCTTAGAATC TTCATACCCC GAACTCTTGG GAAAACTTTA ATCAGTCACC TACAGTCTAC     60
CACCCATTTA GGAGGAGCAA AGCTACCTCA GCTCCTCCGG AGCCGTTTTA AGATCCCCCA    120
TCTTCAAAGC CTAACAGATC AAGCAGCTCT CCGGTGCACA ACCTGCGCCC AGGTAAATGC    180
CAAAAAAGGT CCTAAACCCA GCCCAGGCCA CCGTCTCCAA GAAAACTCAC CAGGAGAAAA    240
GTGGGAAATT GACTTTACAG AAGTAAAACC ACACCGGGCT GGGTACAAAT ACCTTCTAGT    300
ACTGGTAGAC ACCTTCTCTG GATGGACTGA AGCATTTGCT ACCAAAAACG AAACTGTCAA    360
TATGGTAGTT AAGTTTTTAC TCAATGAAAT CATCCCTCGA CGTGGGCTGC CTGTTGCCAT    420
AGGGTCTGAT AATGGAACGG CCTTCGCCTT GTCTATAGTT AATCAGTCA GTAAGGCGTT     480
AAACATTCAA TGGAAGCTCC ATTGTGCCTA TCGACCCAGA GCTCTGGGCA GTAGAACGC     540
ATGAACTGCA CCCTAAAAAA ACACTCTTAC AAAATTAATC TTAAAAACCG GTGTTAATTG    600
TGTTAGTCTC CTTCCCTTAG CCCTACTTAG AGTTAAGGTG CACCCCTTAC TGGGCTGGGT    660
TCTTTACCTT TTGAAATCAT NTTTNGGAAG GGGCTGCCTA TCTTTNCTTA ACTAAAAAAN    720
GCCCATTTGG CAAAAATTTC NCAACTAATT TNTACGTNCC TACGTCTCCC CAACAGGTAN    780
AAAAATCTNC TGCCCTTTTC AAGGAACCAT CCCATCCATT CCTNAACAAA AGGCCTGCCN    840
TTCTTCCCCC AGTAACTNT TTTTTNTTAA AATTCCCAAA AAANGAACCN CCTGCTGGAA     900
AAACNCCCCC CTCCAANCCC CGGCCNAAGN GGAAGGTTCC CTTGAATCCC NCCCCNCNA     960
ANGGCCCGGA ACCNTTAAAN TNGTTCCNGG GGGTNNGGCC TAAAAGNCCN ATTTGGTAAA   1020
CCTANAAATT TTTTCTTTTN TAAAAACCAC NNTTTNNTTT TCTTAAACA AAACCCTNTT    1080
TNTAGNANCN TATTTCCCNC C                                             1101
```

(2) INFORMATION FOR SEQ ID NO: 4:

(i) SEQUENCE CHARACTERISTICS:
(A) LENGTH: 1087 base pairs
(B) TYPE: nucleic acid
(C) STRANDEDNESS: single
(D) TOPOLOGY: linear (xi) SEQUENCE DESCRIPTION: SEQ ID NO: 4:

```
TCTAGAGCTG CGCCTGGATC CCGCCACAGT GAGGAGACCT GAAGACCAGA GAAAACACAG     60
CAAGTAGGCC CTTTAAACTA CTCACCTGTG TTGTCTTCTA ATTTATTCTG TTTTATTTTG    120
TTTCCATCAT TTTAAGGGGT TAAAATCATC TTGTTCAGAC CTCAGCATAT AAAATGACCC    180
ATCTGTAGAC CTCAGGCTCC AACCATACCC CAAGAGTTGT CTGGTTTTGT TTAAATTACT    240
GCCAGGTTTC AGCTGCAGAT ATCCCTGGAA GGAATATTCC AGATTCCCTG AGTAGTTTCC    300
AGGTTAAAAT CCTATAGGCT TCTTCTGTTT TGAGGAAGAG TTCCTGTCAG AGAAAAACAT    360
GATTTTGGAT TTTTAACTTT AATGCTTGTG AAACGCTATA AAAAAAATTT CTACCCCTA    420
GCTTTAAAGT ACTGTTAGTG AGAAATTAAA ATTCCTTCAG GAGGATTAAA CTGCCATTTC    480
AGTTACCCTA ATTCCAAATG TTTTGGTGGT TAGAATCTTC TTTAATGTTC TTGAAGAAGT    540
GTTTATATT TCCCATCNA GATAAATTCT CTCNCNCCTT NNTTTTNTNT CTNNTTTTTT     600
AAAACGGANT CTTGCTCCGT TGTCCANGCT GGGAATTTTN TTTTGGCCAA TCTCCGCTNC    660
CTTGCAANAA TNCTGCNTCC CAAAATTACC NCCTTTTTCC CACCTCCACC CCNNGGAATT    720
```

```
ACCTGGAATT ANAGGCCCCC NCCCCCCCCC CGGCTAATTT GTTTTTGTTT TTAGTAAAAA        780

ACGGGTTTCC TGTTTTAGTT AGGATGGCCC ANNTCTGACC CCNTNATCNT CCCCCTCNGC        840

CCTCNAATNT TNGGNNTANG GCTTACCCCC CCCNGNNGTT TTTCCTCCAT TNAAATTTTC        900

TNTGGANTCT TGAATNNCGG GTTTTCCCTT TTAAACCNAT TTTTTTTTTN NNNCCCCCAN        960

TTTTNCCTCC CCCNTNTNTA ANGGGGTTT CCCAANCCGG GTCCNCCCCC ANGTCCCCAA        1020

TTTTTCTCCC CCCCCCTCTT TTTTCTTTNC CCCAAAANTC CTATCTTTTC CTNNAAATAT       1080

CNANTNT                                                                 1087

(2) INFORMATION FOR SEQ ID NO: 5:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (xi) SEQUENCE DESCRIPTION: SEQ ID NO: 5:

TCTAGACCAA GAAATGGGAG GATTTTAGAG TGACTGATGA TTTCTCTATC ATCTGCAGTT         60

AGTAAACATT CTCCACAGTT TATGCAAAAA GTAACAAAAC CACTGCAGAT GACAAACACT        120

AGGTAACACA CATACTATCT CCCAAATACC TACCCACAAG CTCAACAATT TTAAACTGTT        180

AGGATCACTG GCTCTAATCA CCATGACATG AGGTCACCAC CAAACCATCA AGCGCTAAAC        240

AGACAGAATG TTTCCACTCC TGATCCACTG TGTGGGAAGA AGCACCGAAC TTACCCACTG        300

GGGGGCCTGC NTCANAANAA AAGCCCATGC CCCCGGGTNT NCCTTTNAAC CGGAACGAAT        360

NAACCCACCA TCCCCACANC TCCTCTGTTC NTGGGCCCTG CATCTTGTGG CCTCNTNTNC        420

TTTNGGGGAN ACNTGGGGAA GGTACCCCAT TTCNTTGACC CCNCNANAAA ACCCCNGTGG        480

CCCTTTGCCC TGATTCNCNT GGGCCTTTTC TCTTTTCCCT TTTGGGTTGT TTAAATTCCC        540

AATGTCCCCN GAACCCTCTC CNTNCTGCCC AAAACCTACC TAAATTNCTC NCTANGNNTT        600

TTCTTGGTGT TNCTTTTCAA AGGTNACCTT NCCTGTTCAN NCCCNACNAA AATTTNTTCC        660

NTATNNTGGN CCCNNAAAAA NNNATCNNCC CNAATTGCCC GAATTGGTTN GGTTTTTCCT        720

NCTGGGGGAA ACCCTTTAAA TTTCCCCCTT GGCCGGCCCC CCTTTTTTCC CCCCTTTNGA        780

AGGCAGGNGG TTCTTCCCGA ACTTCCAATT NCAACAGCCN TGCCCATTGN TGAAACCCTT        840

TTCCTAAAAT TAAAAAATAN CCGGTTNNGG NNGGCCTCTT TCCCCTCCNG GNGGGNNGNG        900

AAANTCCTTA CCCCNAAAAA GGTTGCTTAG CCCCCNGTCC CCACTCCCCC NGGAAAAATN        960

AACCTTTTCN AAAAAGGAA TATAANTTTN CCACTCCTTN GTTCTCTTCC                  1010

(2) INFORMATION FOR SEQ ID NO: 6:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (xi) SEQUENCE DESCRIPTION: SEQ ID NO: 6:

TCTAGAGCTC GCGGCCGCGA GCTCTAATAC GACTCACTAT AGGGCGTCGA CTCGATCTCA         60

GCTCACTGCA ATCTCTGCCC CCGGGGTCAT GCGATTCTCC TGCCTCAGCC TTCCAAGTAG        120

CTGGGATTAC AGGCGTGCAA CACCACACCC GGCTAATTTT GTATTTTTAA TAGAGATGGG        180

GTTTTCCCTT GTTGGCCANN ATGGTCTCNA ACCCCTGACC TCNNGTGATC CCCCCNCCCN        240
```

```
NGANCTCNNA CTGCTGGGGA TNNCCGNNNN NNNCCTCCCN NCNCNNNNNN NCNCNNTCCN    300

TNNTCCTTNC TCNNNNNNNN CNNTCNNTCC NNCTTCTCNC CNNNTNTTNT CNNCNNCCNN    360

CNNNCCNCNT NCCCNCNNNT TCNCNTNCNN TNTCCNNCNN NNTCNNCNNN CNNNNCNTNN    420

CCNNTACNTC NTNNNCNNNT CCNTCTNTNN CCTCNNCNNT CNCTNCNCNT TNTCTCCTCN    480

NTNNNNNNCT CCNNNNNTCT CNTCNCNNCN TNCCTCNNTN NCCNCNCCCC NCCTCNCNNC    540

CTNNTTTNNN CNNCNNNTCC NTNCCNTTCN NNTCCNNTNN CNNCNTCNCN NNCNTTNTTC    600

CCNCCNNTTC CTTNCNCNTN NNNTNTCNNN CNCNTCNNTC NTTTNCTCCT NNNTCCCNNC    660

TCNNTTCNCC CNNNTCCNCC CCCCNCCTNT CTCTCNCCCN NNTNNNTNTN NNNCNTCCNC    720

TNTCNCNTTC NTCNNTNCNT TNCTNTCNNC NNCNNTNCNC TNCCNTNTNT CTNNNTCNCN    780

TCNCNTNTCN CCNTCCNTTN CTNTCTCCTN TNTCCTTCCC CTCNCCTNCT CNTTCNCCNC    840

CCNNTNTNTN TNNCNCCNNT NCTNNNCNNC CNTCNTTTCN TCTCTNCTNN NNNTNNCCTC    900

NNCCCNTNCC CTNNTNCNCT NCTNNTACCN TNCTNCTCCN TCTTCCTTCC              950

(2) INFORMATION FOR SEQ ID NO: 7:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (xi) SEQUENCE DESCRIPTION: SEQ ID NO: 7:

TCTAGAGCTC GCGGCCGCGA GCTCAATTAA CCCTCACTAA AGGGAGTCGA CTCGATCAGA     60

CTGTTACTGT GTCTATGTAG AAAGAAGTAG ACATAAGAGA TTCCATTTTG TTCTGTACTA    120

AGAAAAATTC TTCTGCCTTG AGATGCTGTT AATCTGTAAC CCTAGCCCCA ACCCTGTGCT    180

CACAGAGACA TGTGCTGTGT TGACTCAAGG TTCAATGGAT TTAGGGCTAT GCTTTGTTAA    240

AAAAGTGCTT GAAGATAATA TGCTTGTTAA AAGTCATCAC CATTCTCTAA TCTCAAGTAC    300

CCAGGGACAC AATACACTGC GGAAGGCCGC AGGGACCTCT GTCTAGGAAA GCCAGGTATT    360

GTCCAAGATT TCTCCCCATG TGATAGCCTG AGATATGGCC TCATGGGAAG GGTAAGACCT    420

GACTGTCCCC CAGCCCGACA TCCCCCAGCC CGACATCCCC CAGCCCGACA CCCGAAAAGG    480

GTCTGTGCTG AGGAAGATTA NTAAAAGAGG AAGGCTCTTT GCATTGAAGT AAGAAGAAGG    540

CTCTGTCTCC TGCTCGTCCC TGGGCAATAA AATGTCTTGG TGTTAAACCC GAATGTATGT    600

TCTACTTACT GAGAATAGGA GAAAACATCC TTAGGGCTGG AGGTGAGACA CCCTGGCGGC    660

ATACTGCTCT TTAATGCACG AGATGTTTGT NTAATTGCCA TCCAGGGCCA NCCCCTTTCC    720

TTAACTTTTT ATGANACAAA AACTTTGTTC NCTTTTCCTG CGAACCTCTC CCCCTATTAN    780

CCTATTGGCC TGCCCATCCC CTCCCCAAAN GGTGAAAANA TGTTCNTAAA TNCGAGGGAA    840

TCCAAAACNT TTTCCCGTTG GTCCCCTTTC CAACCCCGTC CCTGGGCCNN TTTCCTCCCC    900

AACNTGTCCC GGNTCCTTCN TTCCCNCCCC CTTCCCNGAN AAAAAACCCC GTNTGANGGN    960

GCCCCCTCAA ATTATAACCT TTCCNAAACA AANNGGTTCN AAGGTGGTTT GNTTCCGGTG   1020

CGGCTGGCCT TGAGGTCCCC CCTNCACCCC AATTTGGAAN CCNGTTTTTT TTATTGCCCN   1080

NTCCCC                                                             1086

(2) INFORMATION FOR SEQ ID NO: 8:

(i) SEQUENCE CHARACTERISTICS:
        (A) LENGTH: 1177 base pairs
        (B) TYPE: nucleic acid
```

```
        (C) STRANDEDNESS: single
        (D) TOPOLOGY: linear (xi) SEQUENCE DESCRIPTION: SEQ ID NO: 8:

NCCNTTTAGA TGTTGACAAN NTAAACAAGC NGCTCAGGCA GCTGAAAAAA GCCACTGATA      60

AAGCATCCTG GAGTATCAGA GTTTACTGTT AGATCAGCCT CATTTGACTT CCCCTCCCAC     120

ATGGTGTTTA AATCCAGCTA CACTACTTCC TGACTCAAAC TCCACTATTC CTGTTCATGA     180

CTGTCAGGAA CTGTTGGAAA CTACTGAAAC TGGCCGACCT GATCTTCAAA ATGTGCCCCT     240

AGGAAAGGTG GATGCCACCG TGTTCACAGA CAGTACCNCC TTCCTCGAGA AGGGACTACG     300

AGGGGCCGGT GCANCTGTTA CCAAGGAGAC TNATGTGTTG TGGGCTCAGG CTTTACCANC     360

AAACACCTCA NCNCNNAAGG CTGAATTGAT CGCCCTCACT CAGGCTCTCG GATGGGGTAA     420

GGGATATTAA CGTTAACACT GACAGCAGGT ACGCCTTTGC TACTGTGCAT GTACGTGGAG     480

CCATCTACCA GGAGCGTGGG CTACTCACTC GGCAGGTGGC TGTNATCCAC TGTAAANGGA     540

CATCAAAAGG AAAACNNGGC TGTTGCCCGT GGTAACCANA AANCTGATCN NCAGCTCNAA     600

GATGCTGTGT TGACTTTCAC TCNCNCCTCT TAAACTTGCT GCCCACANTC TCCTTTCCCA     660

ACCAGATCTG CCTGACAATC CCCATACTCA AAAAAAAAAN AANACTGGCC CCGAACCCNA     720

ACCAATAAAA ACGGGGANGG TNGGTNGANC NNCCTGACCC AAAAATAATG GATCCCCCGG     780

GCTGCAGGAA TTCAATTCAN CCTTATCNAT ACCCCCAACN NGGNGGGGGG GGCCNGTNCC     840

CATTNCCCCT NTATTNATTC TTTNNCCCCC CCCCCGGCNT CCTTTTTNAA CTCGTGAAAG     900

GGAAAACCTG NCTTACCAAN TTATCNCCTG GACCNTCCCC TTCCNCGGTN GNTTANAAAA     960

AAAAGCCCNC ANTCCCNTCC NAAATTTGCA CNGAAAGGNA AGGAATTTAA CCTTTATTTT    1020

TTNNTCCTTT ANTTTGTNNN CCCCCTTTTA CCCAGGCGAA CNGCCATCNT TTAANAAAAA    1080

AAANAGAAG TTTATTTTTC CTTNGAACCA TCCCAATANA AANCACCCGC NGGGGAACGG    1140

GGNGGNAGGC CNCTCACCCC CTTTNTGTNG GNGGGNC                            1177

(2) INFORMATION FOR SEQ ID NO: 9:

(i) SEQUENCE CHARACTERISTICS:
        (A) LENGTH: 1146 base pairs
        (B) TYPE: nucleic acid
        (C) STRANDEDNESS: single
        (D) TOPOLOGY: linear (xi) SEQUENCE DESCRIPTION: SEQ ID NO: 9:

NCCNNTTNNT GATGTTGTCT TTTTGGCCTC TCTTTGGATA CTTTCCCTCT CTTCAGAGGT      60

GAAAAGGGTC AAAAGGAGCT GTTGACAGTC ATCCCAGGTG GGCCAATGTG TCCAGAGTAC     120

AGACTCCATC AGTGAGGTCA AAGCCTGGGG CTTTTCAGAG AAGGGAGGAT TATGGGTTTT     180

CCAATTATAC AAGTCAGAAG TAGAAAGAAG GGACATAAAC CAGGAAGGGG GTGGAGCACT     240

CATCACCCAG AGGGACTTGT GCCTCTCTCA GTGGTAGTAG AGGGGCTACT TCCTCCCACC     300

ACGGTTGCAA CCAAGAGGCA ATGGGTGATG AGCCTACAGG GGACATANCC GAGGAGACAT     360

GGGATGACCC TAAGGGAGTA GGCTGGTTTT AAGGCGGTGG GACTGGGTGA GGGAAACTCT     420

CCTCTTCTTC AGAGAGAAGC AGTACAGGGC GAGCTGAACC GGCTGAAGGT CGAGGCGAAA     480

ACACGGTCTG GCTCAGGAAG ACCTTGGAAG TAAAATTATG AATGGTGCAT GAATGGAGCC     540

ATGGAAGGGG TGCTCCTGAC CAAACTCAGC CATTGATCAA TGTTAGGGAA ACTGATCAGG     600

GAAGCCGGGA ATTTCATTAA CAACCCGCCA CACAGCTTGA ACATTGTGAG GTTCAGTGAC     660

CCTTCAAGGG GCCACTCCAC TCCAACTTTG GCCATTCTAC TTTGCNAAAT TTCCAAAACT     720
```

```
TCCTTTTTTA AGGCCGAATC CNTANTCCCT NAAAAACNAA AAAAAATCTG CNCCTATTCT      780

GGAAAAGGCC CANCCCTTAC CAGGCTGGAA GAAATTTTNC CTTTTTTTTT TTTTTGAAGG      840

CNTTTNTTAA ATTGAACCTN AATTCNCCCC CCCAAAAAAA AACCCNCCNG GGGGCGGAT      900

TTCCAAAAAC NAATTCCCTT ACCAAAAAAC AAAAACCCNC CCTTNTTCCC TTCCNCCCTN      960

TTCTTTTAAT TAGGGAGAGA TNAAGCCCCC CAATTTCCNG GNCTNGATNN GTTTCCCCCC     1020

CCCCCATTTT CCNAAACTTT TTCCCANCNA GGAANCCNCC CTTTTTTTNG GTCNGATTNA     1080

NCAACCTTCC AAACCATTTT TCCNNAAAAA NTTTGNTNGG NGGGAAAAAN ACCTNNTTTT     1140

ATAGAN                                                               1146
```

(2) INFORMATION FOR SEQ ID NO: 10:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO: 10:

```
CTTCATTGGG TACGGGCCCC CTCGAGGTCG ACGGTATCGA TAAGCTTGAT ATCGAATTCC       60

TGCAGCCCGG GGGATCCACT AGTTCTAGAG TCAGGAAGAA CCACCAACCT TCCTGATTTT      120

TATTGGCTCT GAGTTCTGAG GCCAGTTTTC TTCTTCTGTT GAGTATGCGG GATTGTCAGG      180

CAGATCTGGC TGTGGAAAGG AGACTGTGGG CAGCAAGTTT AGAGGCGTGA CTGAAAGTCA      240

CACTGCATCT TGAGCTGCTG AATCAGCTTT CTGGTTACCA CGGGCAACAG CCGTGTTTTC      300

CTTTTGATGT CCTTTACAGT GGATTACAGC CACCTGCTGA GGTGAGTAGC CCACGCTCCT      360

GGTAGATGGC TCCACGTACA TGCACAGTAG CAAAGGCGTA CCTGCTGTCA GTGTTAACGT      420

TAATATCCTT ACCCCATCGG AGAGCCTGAG TGAGGGCGAT CAATTCAGCC CTTTTGTGCT      480

GAGGTGTTTG CTGGTTAAGC CCTGAACCCA CAACACATCT GTCTCCATGG TAACAGCTGC      540

ACCGG                                                                 545
```

(2) INFORMATION FOR SEQ ID NO: 11:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO: 11:

```
TCTCCTAGGC TGGGCACAGT GGCTCATACC TGTAATCCTG ACCGTTTCAG AGGCTCAGGT       60

GGGGGGATCG CTTGAGCCCA AGATTTCAAG ACTAGTCTGG GTAACATAGT GAGACCCTAT      120

CTCTACGAAA AATAAAAAA ATGAGCCTGG TGTAGTGGCA CACACCAGCT GAGGAGGGAG      180

AATCGAGCCT AGGAGA                                                     196
```

(2) INFORMATION FOR SEQ ID NO: 12:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (xi) SEQUENCE DESCRIPTION: SEQ ID NO: 12:

```
TCTCCTAGGC TTGGGGGCTC TGACTAGAAA TTCAAGGAAC CTGGGATTCA AGTCCAACTG       60
```

```
TGACACCAAC TTACACTGTG GNCTCCAATA AACTGCTTCT TTCCTATTCC CTCTCTATTA      120

AATAAAATAA GGAAAACGAT GTCTGTGTAT AGCCAAGTCA GNTATCCTAA AAGGAGATAC      180

TAAGTGACAT TAAATATCAG AATGTAAAAC CTGGGAACCA GGTTCCCAGC CTGGGATTAA      240

ACTGACAGCA AGAAGACTGA ACAGTACTAC TGTGAAAAGC CCGAAGNGGC AATATGTTCA      300

CTCTACCGTT GAAGGATGGC TGGGAGAATG AATGCTCTGT CCCCCAGTCC CAAGCTCACT      360

TACTATACCT CCTTTATAGC CTAGGAGA                                        388

(2) INFORMATION FOR SEQ ID NO: 13:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO: 13:

TAGTAGTTGC CTATAATCAT GTTTCTCATT ATTTTCACAT TTTATTAACC AATTTCTGTT       60

TACCCTGAAA AATATGAGGG AAATATATGA AACAGGGAGG CAATGTTCAG ATAATTGATC      120

ACAAGATATG ATTTCTACAT CAGATGCTCT TTCCTTTCCT GTTTATTTCC TTTTTATTTC      180

GGTTGTGGGG TCGAATGTAA TAGCTTTGTT TCAAGAGAGA GTTTTGGCAG TTTCTGTAGC      240

TTCTGACACT GCTCATGTCT CCAGGCATCT ATTTGCACTT TAGGAGGTGT CGTGGGAGAC      300

TGAGAGGTCT ATTTTTTCCA TATTTGGGCA ACTACTA                              337

(2) INFORMATION FOR SEQ ID NO: 14:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (xi) SEQUENCE DESCRIPTION: SEQ ID NO: 14:

TAGTAGTTGC CATACAGTGC CTTTCCATTT ATTTAACCCC CACCTGAACG GCATAAACTG       60

AGTGTTCAGC TGGTGTTTTT TACTGTAAAC AATAAGGAGA CTTTGCTCTT CATTTAAACC      120

AAAATCATAT TTCATATTTT ACGCTCGAGG GTTTTTACCG GTTCCTTTTT ACACTCCTTA      180

AAACAGTTTT TAAGTCGTTT GGAACAAGAT ATTTTTTCTT TCCTGGCAGC TTTTAACATT      240

ATAGCAAATT TGTGTCTGGG GGACTGCTGG TCACTGTTTC TCACAGTTGC AAATCAAGGC      300

ATTTGCAACC AAGAAAAAAA AATTTTTTTG TTTTATTTGA AACTGGACCG GATAAACGGT      360

GTTTGGAGCG GCTGCTGTAT ATAGTTTTAA ATGGTTTATT GCACCTCCTT AAGTTGCACT      420

TATGTGGGGG GGGGNTTTTG NATAGAAAGT NTTTANTCAC ANAGTCACAG GGACTTTTNT      480

CTTTTGGNNA CTGAGCTAAA AAGGGCTGNT TTTCGGGTGG GGGCAGATGA AGGCTCACAG      540

GAGGCCTTTC TCTTAGAGGG GGGAACTNCT A                                    571

(2) INFORMATION FOR SEQ ID NO: 15:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (xi) SEQUENCE DESCRIPTION: SEQ ID NO: 15:

TATATATTTA ATAACTTAAA TATATTTTGA TCACCCACTG GGGTGATAAG ACAATAGATA       60
```

| | |
|---|---|
| TAAAAGTATT TCCAAAAAGC ATAAAACCAA AGTATCATAC CAAACCAAAT TCATACTGCT | 120 |
| TCCCCCACCC GCACTGAAAC TTCACCTTCT AACTGTCTAC CTAACCAAAT TCTACCCTTC | 180 |
| AAGTCTTTGG TGCGTGCTCA CTACTCTTTT TTTTTTTTTT TTTNTTTTGG AGATGGAGTC | 240 |
| TGGCTGTGCA GCCCAGGGGT GGAGTACAAT GGCACAACCT CAGCTCACTG NAACCTCCGC | 300 |
| CTCCCAGGTT CATGAGATTC TCCTGNTTCA GCCTTCCCAG TAGCTGGGAC TACAGGTGTG | 360 |
| CATCACCATG CCTGGNTAAT CTTTTTTNGT TTTNGGGTAG AGATGGGGGT TTTACATGTT | 420 |
| GGCCAGGNTG GTNTCGAACT CCTGACCTCA AGTGATCCAC CCACCTCAGG CTCCCAAAGT | 480 |
| GCTAGGATTA CAGACATGAG CCACTGNGCC CAGNCCTGGT GCATGCTCAC TTCTCTAGGC | 540 |
| AACTACTA | 548 |

(2) INFORMATION FOR SEQ ID NO: 16:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (xi) SEQUENCE DESCRIPTION: SEQ ID NO: 16:

| | |
|---|---|
| TTCCGTTATG CACATGCAGA ATATTCTATC GGTACTTCAG CTATTACTCA TTTTGATGGC | 60 |
| GCAATCCGAG CCTATCCTCA AGATGAGTAT TTAGAAAGAA TTGATTTAGC GATAGACCAA | 120 |
| GCTGGTAAGC ACTCTGACTA CACGAAATTG TTCAGATGTG ATGGATTTAT GACAGTTGAT | 180 |
| CTTTGGAAGA GATTATTAAG TGATTATTTT AAAGGGAATC CATTAATTCC AGAATATCTT | 240 |
| GGTTTAGCTC AAGATGATAT AGAAATAGAA CAGAAAGAGA CTACAAATGA AGATGTATCA | 300 |
| CCAACTGATA TTGAAGAGCC TATAGTAGAA AATGAATTAG CTGCATTTAT TAGCCTTACA | 360 |
| CATAGCGATT TTCCTGATGA ATCTTATATT CAGCCATCGA CATAGCATTA CCTGATGGGC | 420 |
| AACCTTACGA ATAATAGAAA CTGGGTGCGG GGCTATTGAT GAATTCATCC NCAGTAAATT | 480 |
| TGGATATNAC AAAATATAAC TCGATTGCAT TTGGATGATG GAATACTAAA TCTGGCAAAA | 540 |
| GTAACTTTGG AGCTACTAGT AACCTCTCTT TTTGAGATGC AAAATTTTCT TTTAGGGTTT | 600 |
| CTTATTCTCT ACTTTACGGA TATTGGAGCA TAACGGGA | 638 |

(2) INFORMATION FOR SEQ ID NO: 17:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (xi) SEQUENCE DESCRIPTION: SEQ ID NO: 17:

| | |
|---|---|
| ACTGATGGAT GTCGCCGGAG GCGAGGGGCC TTATCTGATG CTCGGCTGCC TGTTCGTGAT | 60 |
| GTGCGCGGCG ATTGGGCTGT TTATCTCAAA CACCGCCACG GCGGTGCTGA TGGCGCCTAT | 120 |
| TGCCTTAGCG GCGGCGAAGT CAATGGGCGT CTCACCCTAT CCTTTTGCCA TGGTGGTGGC | 180 |
| GATGGCGGCT TCGGCGGCGT TTATGACCCC GGTCTCCTCG CCGGTTAACA CCCTGGTGCT | 240 |
| TGGCCCTGGC AAGTACTCAT TTAGCGATTT TGTCAAAATA GGCGTG | 286 |

(2) INFORMATION FOR SEQ ID NO: 18:

(i) SEQUENCE CHARACTERISTICS:
        (A) LENGTH: 262 base pairs
        (B) TYPE: nucleic acid (C) STRANDEDNESS: single
(D) TOPOLOGY: linear (xi) SEQUENCE DESCRIPTION: SEQ ID NO: 18:

| | | | | | |
|---|---|---|---|---|---|
| TCGGTCATAG | CAGCCCCTTC | TTCTCAATTT | CATCTGTCAC | TACCCTGGTG | TAGTATCTCA | 60 |
| TAGCCTTACA | TTTTTATAGC | CTCCTCCCTG | GTCTGTCTTT | TGATTTTCCT | GCCTGTAATC | 120 |
| CATATCACAC | ATAACTGCAA | GTAAACATTT | CTAAAGTGTG | GTTATGCTCA | TGTCACTCCT | 180 |
| GTGNCAAGAA | ATAGTTTCCA | TTACCGTCTT | AATAAAATTC | GGATTTGTTC | TTTNCTATTN | 240 |
| TCACTCTTCA | CCTATGACCG | AA | | | | 262 |

(2) INFORMATION FOR SEQ ID NO: 19:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (xi) SEQUENCE DESCRIPTION: SEQ ID NO: 19:

| | | | | | |
|---|---|---|---|---|---|
| TCGGTCATAG | CAAAGCCAGT | GGTTTGAGCT | CTCTACTGTG | TAAACTCCTA | AACCAAGGCC | 60 |
| ATTTATGATA | AATGGTGGCA | GGATTTTTAT | TATAAACATG | TACCCATGCA | AATTTCCTAT | 120 |
| AACTCTGAGA | TATATTCTTC | TACATTTAAA | CAATAAAAAT | AATCTATTTT | TAAAAGCCTA | 180 |
| ATTTGCGTAG | TTAGGTAAGA | GTGTTTAATG | AGAGGGTATA | AGGTATAAAT | CACCAGTCAA | 240 |
| CGTTTCTCTG | CCTATGACCG | A | | | | 261 |

(2) INFORMATION FOR SEQ ID NO: 20:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO: 20:

| | | | | | |
|---|---|---|---|---|---|
| TACAACGAGG | CGACGTCGGT | AAAATCGGAC | ATGAAGCCAC | CGCTGGTCTT | TTCGTCCGAG | 60 |
| CGATAGGCGC | CGGCCAGCCA | GCGGAACGGT | TGCCCGGATG | GCGAAGCGAG | CCGGAGTTCT | 120 |
| TCGGACTGAG | TATGAATCTT | GTTGTGAAAA | TACTCGCCGC | CTTCGTTCGA | CGACGTCGCG | 180 |
| TCGAAATCTT | CGANCTCCTT | ACGATCGAAG | TCTTCGTGGG | CGACGATCGC | GGTCAGTTCC | 240 |
| GCCCCACCGA | AATCATGGTT | GAGCCGGATG | CTGNCCCCGA | AGNCCTCGTT | TGTN | 294 |

(2) INFORMATION FOR SEQ ID NO: 21:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO: 21:

| | | | | | |
|---|---|---|---|---|---|
| TTGGTAAAGG | GCATGGACGC | AGACGCCTGA | CGTTTGGCTG | AAAATCTTTC | ATTGATTCGT | 60 |
| ATCAATGAAT | AGGAAAATTC | CCAAAGAGGG | AATGTCCTGT | TGCTCGCCAG | TTTTTNTGTT | 120 |
| GTTCTCATGG | ANAAGGCAAN | GAGCTCTTCA | GACTATTGGN | ATTNTCGTTC | GGTCTTCTGC | 180 |
| CAACTAGTCG | NCTTGCNANG | ATCTTCAT | | | | 208 |

(2) INFORMATION FOR SEQ ID NO: 22:

(i) SEQUENCE CHARACTERISTICS:
    (A) LENGTH: 287 base pairs
    (B) TYPE: nucleic acid
    (C) STRANDEDNESS: single
    (D) TOPOLOGY: linear (xi) SEQUENCE DESCRIPTION: SEQ ID NO: 22:

| | | | | | |
|---|---|---|---|---|---|
| NCCNTTGAGC | TGAGTGATTG | AGATNTGTAA | TGGTTGTAAG | GGTGATTCAG | GCGGATTAGG | 60 |
| GTGGCGGGTC | ACCCGGCAGT | GGGTCTCCCG | ACAGGCCAGC | AGGATTTGGG | GCAGGTACGG | 120 |
| NGTGCGCATC | GCTCGACTAT | ATGCTATGGC | AGGCGAGCCG | TGGAAGGNGG | ATCAGGTCAC | 180 |
| GGCGCTGGAG | CTTTCCACGG | TCCATGNATT | GNGATGGCTG | TTCTAGGCGG | CTGTTGCCAA | 240 |
| GCGTGATGGT | ACGCTGGCTG | GAGCATTGAT | TTCTGGTGCC | AAGGTGG | | 287 |

(2) INFORMATION FOR SEQ ID NO: 23:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (xi) SEQUENCE DESCRIPTION: SEQ ID NO: 23:

| | | | | | |
|---|---|---|---|---|---|
| TTGGGTAAAG | GGAGCAAGGA | GAAGGCATGG | AGAGGCTCAN | GCTGGTCCTG | GCCTACGACT | 60 |
| GGGCCAAGCT | GTCGCCGGGG | ATGGTGGAGA | ACTGAAGCGG | GACCTCCTCG | AGGTCCTCCG | 120 |
| NCGTTACTTC | NCCGTCCAGG | AGGAGGGTCT | TTCCGTGGTC | TNGGAGGAGC | GGGGGGAGAA | 180 |
| GATNCTCCTC | ATGGTCNACA | TCCC | | | | 204 |

(2) INFORMATION FOR SEQ ID NO: 24:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (xi) SEQUENCE DESCRIPTION: SEQ ID NO: 24:

| | | | | | |
|---|---|---|---|---|---|
| TGGATTGGTC | AGGAGCGGGT | AGAGTGGCAC | CATTGAGGGG | ATATTCAAAA | ATATTATTTT | 60 |
| GTCCTAAATG | ATAGTTGCTG | AGTTTTTCTT | TGACCCATGA | GTTATATTGG | AGTTTATTTT | 120 |
| TTAACTTTCC | AATCGCATGG | ACATGTTAGA | CTTATTTTCT | GTTAATGATT | NCTATTTTTA | 180 |
| TTAAATTGGA | TTTGAGAAAT | TGGTTNTTAT | TATATCAATT | TTTGGTATTT | GTTGAGTTTG | 240 |
| ACATTATAGC | TTAGTATGTG | ACCA | | | | 264 |

(2) INFORMATION FOR SEQ ID NO: 25:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (xi) SEQUENCE DESCRIPTION: SEQ ID NO: 25:

| | | | | | |
|---|---|---|---|---|---|
| TTACAACGAG | GGGAAACTCC | GTCTCTACAA | AAATTAAAAA | ATTAGCCAGG | TGTGGTGGTG | 60 |
| TGCACCCGCA | ATCCCAGCTA | CTTGGGAGGT | TGAGACACAA | GANTCACCTA | NATGTGGGAG | 120 |
| GTCAAGGTTG | CATGAGTCAT | GATTGTGCCA | CTGCACTCCA | GCCTGGGTGA | CAGACCGAGA | 180 |
| CCCTGCCTCA | ANAGANAANG | AATAGGAAGT | TCAGAAATCN | TGGNTGTGGN | GCCCAGCAAT | 240 |
| CTGCATCTAT | NCAACCCCTG | CAGGCAANGC | TGATGCAGCC | TANGTTCAAG | AGCTGCTGTT | 300 |

TCTGGAGGCA GCAGTTNGGG CTTCCATCCA GTATCACGGC CACACTCGCA CNAGCCATCT    360

GTCCTCCGTN TGTNAC    376

(2) INFORMATION FOR SEQ ID NO: 26:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO: 26:

TTACAACGAG GGGAAACTCC GTCTCTACAA AAATTAAAAA ATTAGCCAGG TGTGGTGGTG    60

TGCACCTGTA ATCCCAGCTA CTTGGGCGGC TGAGACACAA GAACCACCTA AATGTGGGAG    120

GGTCAAGGTT GCATGAGTCA TGATCGCGCC ACTGCACTCC AGCCTGGGTG ACAGACTGAG    180

ACCCTGCCTC AAAAGAAAAA GAATAGGAAG TTCAGAAACC CTGGGTGTGG NGCCCAGCAA    240

TCTGCATTTA AACAATCCCT GCAGGCAATG CTGATGCAGC CTAAGTTCAA GAGCTGCTGT    300

TCTGGAGGCA GNAGTAAGGG CTTCCATCCA GCATCACGGN CAACACTGCA AAAGCACCTG    360

TCCTCGTTGG TA    372

(2) INFORMATION FOR SEQ ID NO: 27:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (xi) SEQUENCE DESCRIPTION: SEQ ID NO: 27:

TTCTGTCCAC ATCTACAAGT TTTATTTATT TTGTGGGTTT TCAGGGTGAC TAAGTTTTTC    60

CCTACATTGA AAAGAGAAGT TGCTAAAAGG TGCACAGGAA ATCATTTTTT TAAGTGAATA    120

TGATAATATG GGTCCGTGCT TAATACAACT GAGACATATT TGTTCTCTGT TTTTTTAGAG    180

TCACCTCTTA AAGTCCAATC CCACAATGGT GAAAAAAAAA TAGAAAGTAT TTGTTCTACC    240

TTTAAGGAGA CTGCAGGGAT TCTCCTTGAA AACGGAGTAT GGAATCAATC TTAAATAAAT    300

ATGAAATTGG TTGGTCTTCT GGGATAAGAA ATTCCCAACT CAGTGTGCTG AAATTCACCT    360

GACTTTTTTT GGGAAAAAAT AGTCGAAAAT GTCAATTTGG TCCATAAAAT ACATGTTACT    420

ATTAAAAGAT ATTTAAAGAC AAATTCTTTC AGAGCTCTAA GATTGGTGTG GACAGAA    477

(2) INFORMATION FOR SEQ ID NO: 28:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (xi) SEQUENCE DESCRIPTION: SEQ ID NO: 28:

TCTNCAACCT CTTGANTGTC AAAAACCTTN TAGGCTATCT CTAAAAGCTG ACTGGTATTC    60

ATTCCAGCAA AATCCCTCTA GTTTTTGGAG TTTCCTTTTA CTATCTGGGG CTGCCTGAGC    120

CACAAATGCC AAATTAAGAG CATGGCTATT TTCGGGGGCT GACAGGTCAA AAGGGGTGTA    180

AATCCGATAA GCCTCCTGGA GGTGCTCTAA AAACACTCCT GGTGACTCAT CATGCCCCTG    240

GACGACTTCA ATCGNCTTAG ACAAGTTTAT AGGTTTCTGG GCAGCTCCCT GAATACCCAC    300

GAGGAGATAC CGGTGGAAAT CGTCAAAAGT TCTCCCTCCA CTTGAGAAAT TTGGGTCCCA    360

```
ATTAGGTCCC AATTGGGTCT CTAATCACTA TTCCTCTAGC TTCCTCCTCC GGNCTATTGG      420

TTGATGTGAG GTTGAAGA                                                    438
```

(2) INFORMATION FOR SEQ ID NO: 29:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (xi) SEQUENCE DESCRIPTION: SEQ ID NO: 29:

```
AAGAGGGTAC CAGCCCCAAG CCTTGACAAC TTCCATAGGG TGTCAAGCCT GTGGGTGCAC       60

AGAAGTCAAA AATTGAGTTT TGGGATCCTC AGCCTAGATT TCAGAGGATA TAAAGAAACA      120

CCTAACACCT AGATATTCAG ACAAAAGTTT ACTACAGGGA TGAAGCTTTC ACGGAAAACC      180

TCTACTAGGA AAGTACAGAA GAGAAATGTG GGTTTGGAGC CCCCAAACAG AATCCCCTCT      240

AGAACACTGC CTAATGAAAC TGTGAGAAGA TGGCCACTGT CATCCAGACA CCAGAATGAT      300

AGACCCACCA AAAACTTATG CCATATTGCC TATAAAACCT ACAGACACTC AATGCCAGCC      360

CCATGAAAAA AAAACTGAGA GAAGACTGT NCCCTACAAT GCCACCGGAG CAGAACTGCC       420

CCAGGCCATG GAAGCACAGC TCTTATATCA ATGTGACCTG GATGTTGAGA CATGGAATCC      480

NANGAAATCN TTTTAANACT TCCACGGTTN AATGACTGCC CTATTANATT CNGAACTTAN      540

ATCCNGGCCT GTGACCTCTT TGCTTTGGCC ATTCCCCCTT TTTGGAATGG CTNTTTTTTT      600

CCCATGCCTG TNCCCTCTTA                                                  620
```

(2) INFORMATION FOR SEQ ID NO: 30:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 30:

```
TTACAACGAG GGGGTCAATG TCATAAATGT CACAATAAAA CAATCTCTTC TTTTTTTTTT       60

TTTTTTTTTT TTTTTTTTTT TTTTTTTTTT TTTTTTTTTT                            100
```

(2) INFORMATION FOR SEQ ID NO: 31:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (xi) SEQUENCE DESCRIPTION: SEQ ID NO: 31:

```
TAGTCTATGC GCCGGACAGA GCAGAATTAA ATTGGAAGTT GCCCTCCGGA CTTTCTACCC       60

ACACTCTTCC TGAAAAGAGA AAGAAAAGAG GCAGGAAAGA GGTTAGGATT TCATTTTCAA      120

GAGTCAGCTA ATTAGGAGAG CAGAGTTTAG ACAGCAGTAG GCACCCCATG ATACAAACCA      180

TGGACAAAGT CCCTGTTTAG TAACTGCCAG ACATGATCCT GCTCAGGTTT TGAAATCTCT      240

CTGCCCATAA AAGATGGAGA GCAGGAGTGC CATCCACATC AACACGTGTC CAAGAAAGAG      300

TCTCAGGGAG ACAAGGGTAT CAAAAAACAA GATTCTTAAT GGGAAGGAAA TCAAACCAAA      360

AAATTAGATT TTTCTCTACA TATATATAAT ATACAGATAT TTAACACATT ATTCCAGAGG      420

TGGCTCCAGT CCTTGGGGCT TGAGAGATGG TGAAAACTTT TGTTCCACAT TAACTTCTGC      480
```

```
TCTCAAATTC TGAAGTATAT CAGAATGGGA CAGGCAATGT TTTGCTCCAC ACTGGGGCAC      540

AGACCCAAAT GGTTCTGTGC CCGAAGAAGA GAAGCCCGAA AGACATGAAG GATGCTTAAG      600

GGGGGTTGGG AAAGCCAAAT TGGTANTATC TTTTCCTCCT GCCTGTGTTC CNGAAGTCTC      660

CNCTGAAGGA ATTCTTAAAA CCCTTTGTGA GGAAATGCCC CCTTACCATG ACAANTGGTC      720

CCATTGCTTT TAGGGNGATG GAAACACCAA GGGTTTTGAT CC                        762

(2) INFORMATION FOR SEQ ID NO: 32:

(i) SEQUENCE CHARACTERISTICS:
         (A) LENGTH: 276 base pairs
         (B) TYPE: nucleic acid
         (C) STRANDEDNESS: single
         (D) TOPOLOGY: linear (xi) SEQUENCE DESCRIPTION: SEQ ID NO: 32:

TAGTCTATGC GTGTATTAAC CTCCCCTCCC TCAGTAACAA CCAAAGAGGC AGGAGCTGTT       60

ATTACCAACC CCATTTTACA GATGCATCAA TAATGACAGA GAAGTGAAGT GACTTGCGCA      120

CACAACCAGT AAATTGGCAG AGTCAGATTT GAATCCATGG AGTCTGGTCT GCACTTTCAA      180

TCACCGAATA CCCTTTCTAA GAAACGTGTG CTGAATGAGT GCATGGATAA ATCAGTGTCT      240

ACTCAACATC TTTGCCTAGA TATCCCGCAT AGACTA                               276

(2) INFORMATION FOR SEQ ID NO: 33:

(i) SEQUENCE CHARACTERISTICS:
         (A) LENGTH: 477 base pairs
         (B) TYPE: nucleic acid
         (C) STRANDEDNESS: single
         (D) TOPOLOGY: linear (xi) SEQUENCE DESCRIPTION: SEQ ID NO: 33:

TAGTAGTTGC CAAATATTTG AAAATTTACC CAGAAGTGAT TGAAAACTTT TTGGAAACAA       60

AAACAAATAA AGCCAAAAGG TAAAATAAAA ATATCTTTGC ACTCTCGTTA TTACCTATCC      120

ATAACTTTTT CACCGTAAGC TCTCCTGCTT GTTAGTGTAG TGTGGTTATA TTAAACTTTT      180

TAGTTATTAT TTTTTATTCA CTTTTCCACT AGAAAGTCAT TATTGATTTA GCACACATGT      240

TGATCTCATT TCATTTTTTC TTTTTATAGG CAAAATTTGA TGCTATGCAA CAAAAATACT      300

CAAGCCCATT ATCTTTTTTC CCCCCGAAAT CTGAAAATTG CAGGGACAG AGGGAAGTTA      360

TCCCATTAAA AAATTGTAAA TATGTTCAGT TTATGTTTAA AAATGCACAA AACATAAGAA      420

AATTGTGTTT ACTTGAGCTG CTGATTGTAA GCAGTTTTAT CTCAGGGCA ACTACTA        477

(2) INFORMATION FOR SEQ ID NO: 34:

(i) SEQUENCE CHARACTERISTICS:
         (A) LENGTH: 631 base pairs
         (B) TYPE: nucleic acid
         (C) STRANDEDNESS: single
         (D) TOPOLOGY: linear (xi) SEQUENCE DESCRIPTION: SEQ ID NO: 34:

TAGTAGTTGC CAATTCAGAT GATCAGAAAT GCTGCTTTCC TCAGCATTGT CTTGTTAAAC       60

CGCATGCCAT TTGGAACTTT GGCAGTGAGA AGCCAAAAGG AAGAGGTGAA TGACATATAT      120

ATATATATAT ATTCAATGAA AGTAAAATGT ATATGCTCAT ATACTTTCTA GTTATCAGAA      180

TGAGTTAAGC TTTATGCCAT TGGGCTGCTG CATATTTTAA TCAGAAGATA AAAGAAAATC      240

TGGGCATTTT TAGAATGTGA TACATGTTTT TTTAAAACTG TTAAATATTA TTTCGATATT      300
```

```
TGTCTAAGAA CCGGAATGTT CTTAAAATTT ACTAAAACAG TATTGTTTGA GGAAGAGAAA      360

ACTGTACTGT TTGCCATTAT TACAGTCGTA CAAGTGCATG TCAAGTCACC CACTCTCTCA      420

GGCATCAGTA TCCACCTCAT AGCTTTACAC ATTTTGACGG GGAATATTGC AGCATCCTCA      480

GGCCTGACAT CTGGGAAAGG CTCAGATCCA CCTACTGCTC CTTGCTCGTT GATTTGTTTT      540

AAAATATTGT GCCTGGTGTC ACTTTTAAGC CACAGCCCTG CCTAAAAGCC AGCAGAGAAC      600

AGAACCCGCA CCATTCTATA GGCAACTACT A                                    631

(2) INFORMATION FOR SEQ ID NO: 35:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 35:

TAGTAGTTGC CATCCCATAT TACAGAAGGC TCTGTATACA TGACTTATTT GGAAGTGATC       60

TGTTTTCTCT CCAAACCCAT TTATCGTAAT TTCACCAGTC TTGGATCAAT CTTGGTTTCC      120

ACTGATACCA TGAAACCTAC TTGGAGCAGA CATTGCACAG TTTTCTGTGG TAAAAACTAA      180

AGGTTTATTT GCTAAGCTGT CATCTTATGC TTAGTATTTT TTTTTTACAG TGGGGAATTG      240

CTGAGATTAC ATTTTGTTAT TCATTAGATA CTTTGGGATA ACTTGACACT GTCTTCTTTT      300

TTTCGCTTTT AATTGCTATC ATCATGCTTT TGAAACAAGA ACACATTAGT CCTCAAGTAT      360

TACATAAGCT TGCTTGTTAC GCCTGGTGGT TTAAAGGACT ATCTTTGGCC TCAGGTTCAC      420

AAGAATGGGC AAAGTGTTTC CTTATGTTCT GTAGTTCTCA ATAAAAGATT GCCAGGGGCC      480

GGGTACTGTG GCTCGCACTG TAATCCCAGC ACTTTGGGAA GCTGAGGCTG GCGGATCATG      540

TTAGGGCAGG TGTTCGAAAC CAGCCTGGGC AACTACTA                             578

(2) INFORMATION FOR SEQ ID NO: 36:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (xi) SEQUENCE DESCRIPTION: SEQ ID NO: 36:

TAGTAGTTGC CTGTAATCCC AGCAACTCAG GAGGCTGGGG CAGGAGAATC AGTTGAACCT       60

GGGAGGCAGA AGTTGTAATT AGCAAAGATC GCACCATTGC ACTTCAGCCT GGGCAACAAG      120

AGTGAGATTC CATCTCAAAA ACAAAAAAAA GAAAAAGAAA AGAAAAGGAA AAAACGTATA      180

AACCCAGCCA AAACAAAATG ATCATTCTTT TAATAAGCAA GACTAATTTA ATGTGTTTAT      240

TTAATCAAAG CAGTTGAATC TTCTGAGTTA TTGGTGAAAA TACCCATGTA GTTAATTTAG      300

GGTTCTTACT TGGGTGAACG TTTGATGTTC ACAGGTTATA AAATGGTTAA CAAGGAAAAT      360

GATGCATAAA GAATCTTATA AACTACTAAA AATAAATAAA ATATAAATGG ATAGGTGCTA      420

TGGATGGAGT TTTTGTGTAA TTTAAAATCT TGAAGTCATT TTGGATGCTC ATTGGTTGTC      480

TGGTAATTTC CATTAGGAAA AGGTTATGAT ATGGGGAAAC TGTTTCTGGA AATTGCGGAA      540

TGTTTCTCAT CTGTAAAATG CTAGTATCTC AGGGCAACTA CTA                       583

(2) INFORMATION FOR SEQ ID NO: 37:

(i) SEQUENCE CHARACTERISTICS:
        (A) LENGTH: 716 base pairs
```

(B) TYPE: nucleic acid
(C) STRANDEDNESS: single
(D) TOPOLOGY: linear (xi) SEQUENCE DESCRIPTION: SEQ ID NO: 37:

```
GATCTACTAG TCATNTGGAT TCTATCCATG GCAGCTAAGC CTTTCTGAAT GGATTCTACT      60
GCTTTCTTGT TCTTTAATCC AGACCCTTAT ATATGTTTAT GTTCACAGGC AGGGCAATGT     120
TTAGTGAAAA CAATTCTAAA TTTTTTATTT TGCATTTTCA TGCTAATTTC CGTCACACTC     180
CAGCAGGCTT CCTGGGAGAA TAAGGAGAAA TACAGCTAAA GACATTGTCC CTGCTTACTT     240
ACAGCCTAAT GGTATGCAAA ACCACTTCAA TAAAGTAACA GGAAAAGTAC TAACCAGGTA     300
GAATGGACCA AAACTGATAT AGAAAAATCA GAGGAAGAGA GGAACAAATA TTTACTGAGT     360
CCTAGAATGT ACAAGGCTTT TTAATTACAT ATTTTATGTA AGGCCTGCAA AAAACAGGTG     420
AGTAATCAAC ATTTGTCCCA TTTTACATAT AAGGAAACTG AAGCTTAAAT TGAATAATTT     480
AATGCATAGA TTTTATAGTT AGACCATGTT CAGGTCCCTA TGTTATACTT ACTAGCTGTA     540
TGAATATGAG AAAATAATTT TGTTATTTTC TTGGCATCAG TATTTTCATC TGCAAAATAA     600
AGCTAAAGTT ATTTAGCAAA CAGTCAGCAT AGTGCCTGAT ACATAGTAGG TGCTCCAAAC     660
ATGATTACNC TANTATTNGG TATTANAAAA ATCCAATATA GGCNTGGATA AAACCG         716
```

(2) INFORMATION FOR SEQ ID NO: 38:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (xi) SEQUENCE DESCRIPTION: SEQ ID NO: 38:

```
TTCTGTCCAC ATATCATCCC ACTTAATTG TTAATCAGCA AAACTTTCAA TGAAAAATCA       60
TCCATTTTAA CCAGGATCAC ACCAGGAAAC TGAAGGTGTA TTTTTTTTTA CCTTAAAAAA     120
AAAAAAAAAA ACCAAACAAA CCAAAACAGA TTAACAGCAA AGAGTTCTAA AAAATTTACA     180
TTTCTCTTAC AACTGTCATT CAGAGAACAA TAGTTCTTAA GTCTGTTAAA TCTTGGCATT     240
AACAGAGAAA CTTGATGAAN AGTTGTACTT GGAATATTGT GGATTTTTTT TTTTGTCTAA     300
TCTCCCCCTA TTGTTTTGCC AACAGTAATT TAAGTTTGTG TGGAACATCC CCGTAGTTGA     360
AGTGTAAACA ATGTATAGGA AGGAATATAT GATAAGATGA TGCATCACAT ATGCATTACA     420
TGTAGGGACC TTCACAACTT CATGCACTCA GAAAACATGC TTGAAGAGGA GGAGAGGACG     480
GCCCAGGGTC ACCATCCAGG TGCCTTGAGG ACAGAGAATG CAGAAGTGGC ACTGTTGAAA     540
TTTAGAAGAC CATGTGTGAA TGGTTTCAGG CCTGGGATGT TGCCACCAA GAAGTGCCTC      600
CGAGAAATTT CTTTCCCATT TGGAATACAG GGTGGCTTGA TGGGTACGGT GGGTGACCCA     660
ACGAAGAAAA TGAAATTCTG CCCTTTCC                                        688
```

(2) INFORMATION FOR SEQ ID NO: 39:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO: 39:

```
TAGTAGTTGC CGCNNACCTA AAANTTGGAA AGCATGATGT CTAGGAAACA TANTAAAATA      60
GGGTATGCCT ATGTGCTACA GAGAGATGTT AGCATTTAAA GTGCATANTT TTATGTATTT    120
```

```
TGACAAATGC ATATNCCTCT ATAATCCACA ACTGATTACG AAGCTATTAC AATTAAAAAG      180

TTTGGCCGGG CGTGGTGGGC GGTGGCTGAC GCCTGTAATC CCAGCACTTT GGGAGGCCGA      240

GGCACGCGGA TCACGAGGTC GGGAGTTCAA GACCATCCTG GCTAACACGG TGAAAGTCCA      300

TCTCTACTAA AAATACGAAA AAATTACCCC GGCGTGGTGG CGGGCGCCTG TAGTCCCAGC      360

TACTCCGGAG GCTGAGGCAG GAGAATGGCG TGAACCCAGG ACACGGAGCT TGCAGTGTGC      420

CAACATCACG TCACTGCCCT CCAGCCTGGG GGACAGGAAC AAGANTCCCG TCCTCANAAA      480

AGAAAAATAC TACTNATANT TTCNACTTTA TTTTAANTTA CACAGAACTN CCTCTTGGTA      540

CCCCCTTACC ATTCATCTCA CCCACCTCCT ATAGGGCACN NCTAA                     585

(2) INFORMATION FOR SEQ ID NO: 40:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (xi) SEQUENCE DESCRIPTION: SEQ ID NO: 40:

TCTGTCCACA CCAATCTTAG AAGCTCTGAA AAGAATTTGT CTTTAAATAT CTTTTAATAG       60

TAACATGTAT TTTATGGACC AAATTGACAT TTCGACTGT TTTTTCCAAA AAAGTCAGGT      120

GAATTTCAGC ACACTGAGTT GGGAATTTCT TATCCCAGAA GACCAACCAA TTTCATATTT      180

ATTTAAGATT GATTCCATAC TCCGTTTTCA AGGAGAATCC CTGCAGTCTC CTTAAAGGTA      240

GAACAAATAC TTCCTATTTT TTTTTCACCA TTGTGGGATT GGACTTTAAG AGGTGACTCT      300

AAAAAAACAG AGAACAAATA TGTCTCAGTT GTATTAAGCA CGGACCCATA TTATCATATT      360

CACTTAAAAA AATGATTTCC TGTGCACCTT TTGGCAACTT CTCTTTTCAA TGTAGGGAAA      420

AACTTAGTCA CCCTGAAAAC CCACAAAATA AATAAAACTT GTAGATGTGG ACAGA          475

(2) INFORMATION FOR SEQ ID NO: 41:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (xi) SEQUENCE DESCRIPTION: SEQ ID NO: 41:

TAAGAGGGTA CATCGGGTAA GAACGTAGGC ACATCTAGAG CTTAGAGAAG TCTGGGGTAG       60

GAAAAAAATC TAAGTATTTA TAAGGGTATA GGTAACATTT AAAAGTAGGG CTAGCTGACA      120

TTATTTAGAA AGAACACATA CGGAGAGATA AGGGCAAAGG ACTAAGACCA GAGGAACACT      180

AATATTTAGT GATCACTTCC ATTCTTGGTA AAAATAGTAA CTTTTAAGTT AGCTTCAAGG      240

AAGATTTTTG GCCATGATTA GTTGTCAAAA GTTAGTTCTC TTGGGTTTAT ATTACTAATT      300

TTGTTTTAAG ATCCTTGTTA GTGCTTTAAT AAAGTCATGT TATATCAAAC GCTCTAAAAC      360

ATTGTAGCAT GTTAAATGTC ACAATATACT TACCATTTGT TGTATATGGC TGTACCCTCT      420

CTA                                                                   423

(2) INFORMATION FOR SEQ ID NO: 42:

(i) SEQUENCE CHARACTERISTICS:
        (A) LENGTH: 527 base pairs
        (B) TYPE: nucleic acid
        (C) STRANDEDNESS: single
        (D) TOPOLOGY: linear
```

(xi) SEQUENCE DESCRIPTION: SEQ ID NO: 42:

```
TCTCCTAGGC TAATGTGTGT GTTTCTGTAA AAGTAAAAAG TTAAAAATTT TAAAAATAGA       60
AAAAAGCTTA TAGAATAAGA ATATGAAGAA AGAAAATATT TTTGTACATT TGCACAATGA      120
GTTTATGTTT TAAGCTAAGT GTTATTACAA AAGAGCCAAA AAGGTTTTAA AAATTAAAAC      180
GTTTGTAAAG TTACAGTACC CTTATGTTAA TTTATAATTG AAGAAAGAAA AACTTTTTTT      240
TATAAATGTA GTGTAGCCTA AGCATACAGT ATTTATAAAG TCTGGCAGTG TTCAATAATG      300
TCCTAGGCCT TCACATTCAC TCACTGACTC ACCCAGAGCA ACTTCCAGTC CTGTAAGCTC      360
CATTCGTGGT AAGTGCCCTA TACAGGTGCA CCATTTATTT TACAGTATTT TTACTGTACC      420
TTCTCTATGT TTCCATATGT TTCGATATAC AAATACCACT GGTTACTATN GCCCNACAGG      480
TAATTCCAGT AACACGGCCT GTATACGTCT GGTANCCCTA GNGAAGA                    527
```

(2) INFORMATION FOR SEQ ID NO: 43:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (xi) SEQUENCE DESCRIPTION: SEQ ID NO: 43:

```
TCTTCAACCT CGTAGGACAA CTCTCATATG CCTGGGCACT ATTTTTAGGT TACTACCTTG       60
GCTGCCCTTC TTTAAGAAAA AAAAAAGAAG AAAAAAGAAC TTTTCCACAA GTTTCTCTTC      120
CTCTAGTTGG AAAATTAGAG AAATCATGTT TTTAATTTTG TGTTATTTCA GATCACAAAT      180
TCAAACACTT GTAAACATTA AGCTTCTGTT CAATCCCCTG GAAGAGGAT TCATTCTGAT       240
ATTTACGGTT CAAAAGAAGT TGTAATATTG TGCTTGGAAC ACAGAGAACC AGTTATTAAC      300
TTCCTACTAC TATTATATAA TAAATAATAA C                                     331
```

(2) INFORMATION FOR SEQ ID NO: 44:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (xi) SEQUENCE DESCRIPTION: SEQ ID NO: 44:

```
GGCTTAGTAG TTGCCAGGCA AAATARCGTT GATTCTCCTC AGGAGCCACC CCCAACACCC       60
CTGTTTGCTT CTAGACCTAT ACCTAGACTA AAGTCCCAGC AGACCCCTAG AGGTGAGGTT      120
CAGAGTGACC CTTGAGGAGA TGTGCTACAC TAGAAAAGAA CTGCTTGAGT TTTCTAATTT      180
ATATAAGCAG AAATCTGGAG AAGAGTCATA GGAATGGATA TTAAGGGTGT GAGATAATGG      240
CGGAAGGAAT ATAGAGTTGG ATCAGGCTGG ACTTATTGAT TTGAACCCAC TAAGTAGAGA      300
TTCTGCTTTT GATGTTGCAG CTCAGGGAGT TAAAAAAGGT TTTAATGGTT CTAATAGTTT      360
ATTTGCTTGG TTAGCTGAAA TATGGATAAA AGATGGCCCA CTGTGAGCAA GCTGGAAATG      420
CCTGATCTCT CTCAGTTTAA TGTAGAGGAA GGGATCCAAA AGTTTAGGGA GANTTGGATG      480
CTGGRAKTGG ATTGGTCACT TTGRGACCTA CCCWTCCCAG CTGGGAGGGT CCAGAAGATA      540
CACCCTTGAC CAACGCTTTG CGAAATGGAT TTGTGATGGC GGCAACTACT AA              592
```

(2) INFORMATION FOR SEQ ID NO: 45:

(i) SEQUENCE CHARACTERISTICS:

(A) LENGTH: 567 base pairs
        (B) TYPE: nucleic acid
        (C) STRANDEDNESS: single
        (D) TOPOLOGY: linear (xi) SEQUENCE DESCRIPTION: SEQ ID NO: 45:

GGCTTAGTAG TTGCCATTGC GAGTGCTTGC TCAACGAGCG TTGAACATGG CGGATTGTCT      60

AGATTCAACG GATTTGAGTT TTACCAGCAA AGCGAACCAA GCGCGGCCCA GAGAATTATG     120

GGTTGGTTGG CTTTGAAAAG ATGGAAATCC TGTAGGCCTA GTCAGAAAAG CCTTCTTGCA     180

GAACAGTTGG TTCTCGGGCG AACGCTCATC AAGATGCCCA TTGGAAAGGC TAGCGTGTAT     240

TTGGGAGAGC CTGATAGCGT GTCTTCTGAT GATGTTTGTG CTTGGACAGT GACAAAAGAT     300

ATGCAAAGCA AGTCCGAACT AGACGTCAAG CTTCGTGAGC AAATTATTGT AGACTCCTAC     360

TTATACTGTG AGGAATGATA GCCAAGGGTG GGGACTTTAA GACTAAGGTG GTTTGTACTT     420

GCGCCGATGA TCCCAGGCAG AAAGAMCTGA TCGCTAGTTT TATACGGGCA ACTACTAAGC     480

CGAATTCCAG CACACTGGCG GCCGTTACTA ATTGGATCCG ANCTCGGTAC CAGCTTGATG     540

CATASCTTGA GTTWTCTATA NTGTCNC                                         567

(2) INFORMATION FOR SEQ ID NO: 46:

(i) SEQUENCE CHARACTERISTICS:
        (A) LENGTH: 908 base pairs
        (B) TYPE: nucleic acid
        (C) STRANDEDNESS: single
        (D) TOPOLOGY: linear (xi) SEQUENCE DESCRIPTION: SEQ ID NO: 46:

GAGCGAAAGA CCGAGGGCAG NGNNTANGNG CGANGAAGCG GAGAGGGCCA AAAAGCAACC      60

GCTTTCCCCG GGGGGTGCCG ATTCATTAAG GCAGGTGGAG GACAGGTTTC CCGATGGAAG     120

GCGGCAGGGG CGCAAGCAAT TAATGTGAGT AGGCCATTCA TTAGCACCCG GCTTAACAT     180

TTAAGCTTCG GGTTGGTATG TGGTGGGAAT TGTGAGCGGA TAACAATTTC ACACAGGAAA     240

CAGCTATGAC CATGATTACG CCAAGCTATT TAGGTGACAT TATAGAATAA CTCAAGTTAT     300

GCATCAAGCT TGGTACCGAG TTCGGATCCA CTAGTAACGG CCGCCAGTGT GTGGAATTCG     360

GCTTAGTAGT TGCCGACCAT GGAGTGCTAC CTAGGCTAGA ATACCTGAGY TCCTCCCTAG     420

CCTCACTCAC ATTAAATTGT ATCTTTTCTA CATTAGATGT CCTCAGCGCC TTATTTCTGC     480

TGGACWATCG ATAAATTAAT CCTGATAGGA TGATAGCAGC AGATTAATTA CTGAGAGTAT     540

GTTAATGTGT CATCCCTCCT ATATAACGTA TTTGCATTTT AATGGAGCAA TTCTGGAGAT     600

AATCCCTGAA GGCAAAGGAA TGAATCTTGA GGGTGAGAAA GCCAGAATCA GTGTCCAGCT     660

GCAGTTGTGG GAGAAGGTGA TATTATGTAT GTCTCAGAAG TGACACCATA TGGGCAACTA     720

CTAAGCCCGA ATTCCAGCAC ACTGGCGGGC GTTACTAATG GATCCGAGCT CGGTACCAAG     780

CTTGATGCAT AGCTTGAGTA TCTATAGTGT CACTAAATAG CCTGGCGTTA TCATGGTCAT     840

AGCTGTTTCC TGTGTGAAAT TGTTATCCGC TCCCAATTCC CCCCACCATA CGAGCCGGAA     900

CATAAAGT                                                              908

(2) INFORMATION FOR SEQ ID NO: 47:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (xi) SEQUENCE DESCRIPTION: SEQ ID NO: 47:

```
TGCCAACAAG GAAAGTTTTA AATTTCCCCT TGAGGATTCT TGGTGATCAT CAAATTCAGT      60
GGTTTTTAAG GTTGTTTTCT GTCAAATAAC TCTAACTTTA AGCCAAACAG TATATGGAAG     120
CACAGATAKA ATATTACACA GATAAAAGAG GAGTTGATCT AAAGTARAGA TAGTTGGGGG     180
CTTTAATTTC TGGAACCTAG GTCTCCCCAT CTTCTTCTGT GCTGAGGAAC TTCTTGGAAG     240
CGGGGATTCT AAAGTTCTTT GGAAGACAGT TTGAAAACCA CCATGTTGTT CTCAGTACCT     300
TTATTTTTAA AAAGTAGGTG AACATTTTGA GAGAGAAAAG GGCTTGGTTG AGATGAAGTC     360
CCCCCCCCCC CTTTTTTTTT TTTTAGCTGA AATAGATACC CTATGTTNAA RGAARGGATT     420
ATTATTTACC ATGCCAYTAR SCACATGCTC TTTGATGGGC NYCTCCSTAC CCTCCTTAAG     480
```

(2) INFORMATION FOR SEQ ID NO: 48:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (xi) SEQUENCE DESCRIPTION: SEQ ID NO: 48:

```
AAGAGGGTAC CGAGTGGAAT TTCCGCTTCA CTAGTCTGGT GTGGCTAGTC GGTTTCGTGG      60
TGGCCAACAT TACGAACTTC CAACTCAACC GTTCTTGGAC GTTCAAGCGG GAGTACCGGC     120
GAGGATGGTG GCGTGAATTC TGGCCTTTCT TTGCCGTGGG ATCGGTAGCC GCCATCATCG     180
GTATGTTTAT CAAGATCTTC TTTACTAACC CGACCTCTCC GATTTACCTG CCCGAGCCGT     240
GGTTTAACGA GGGGAGGGGG ATCCAGTCAC GCGAGTACTG GTCCCAGATC TTCGCCATCG     300
TCGTGACAAT GCCTATCAAC TTCGTCGTCA ATAAGTTGTG GACCTTCCGA ACGGTGAAGC     360
ACTCCGAAAA CGTCCGGTGG CTGCTGTGCG GTGACTCCCA AAATCTTGAT AACAACAAGG     420
TAACCGAATC GCGCTAAGGA ACCCCGGCAT CTCGGGTACT CTGCATATGC GTACCCCTTA     480
AGCCGAATTC CAGCACACTG GCGGCCGTTA CTAATTGGAT CCGAACTCCG TAACCAAGCC     540
TGATGCGTAA CTTGAGTTAT TCTATAGTGT CCCTAAAATA ACCTGGCGTT A             591
```

(2) INFORMATION FOR SEQ ID NO: 49:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO: 49:

```
AAGAGGGTAC CTGCCTTGAA ATTTAAATGT CTAAGGAAAR TGGGAGATGA TTAAGAGTTG      60
GTGTGGCYTA GTCACACCAA AATGTATTTA TTACATCCTG CTCCTTTCTA GTTGACAGGA     120
AAGAAAGCTG CTGTGGGGAA AGGAGGGATA AATACTGAAG GGATTTACTA AACAAATGTC     180
CATCACAGAG TTTTCCTTTT TTTTTTTTTG AGACAGAGTC TTGCTCTGTC ACCCAGGCTG     240
GAATGAAGWG GTATGATCTC AGTTGAATGC AACCTCTACC TCCTAGGTTC AAGCGATTCT     300
CATGCCTCAG CCTCCTGAGC AGCTGGGACT ATAGGCGCAT GCTACCATGC CAGGCTAATT     360
TTTATATTTT TATTAGAGAC GGGGTGTTGC CATGTTGGCC AGGCAGGTCT CGAACTCCTG     420
GGCCTCAGAT GATCTGCCCC ACCGTACCCT CTTA                                454
```

(2) INFORMATION FOR SEQ ID NO: 50:

(i) SEQUENCE CHARACTERISTICS:
    (A) LENGTH: 463 base pairs
    (B) TYPE: nucleic acid
    (C) STRANDEDNESS: single
    (D) TOPOLOGY: linear (xi) SEQUENCE DESCRIPTION: SEQ ID NO: 50:

| | | | | | |
|---|---|---|---|---|---|
| AAGAGGGTAC | CAAAAAAAAG | AAAAAGGAAA | AAAAGAAAAA | CAACTTGTAT | AAGGCTTTCT | 60 |
| GCTGCATACA | GCTTTTTTTT | TTTAAATAAA | TGGTGCCAAC | AAATGTTTTT | GCATTCACAC | 120 |
| CAATTGCTGG | TTTTGAAATC | GTACTCTTCA | AAGGTATTTG | TGCAGATCAA | TCCAATAGTG | 180 |
| ATGCCCCGTA | GGTTTTGTGG | ACTGCCCACG | TTGTCTACCT | TCTCATGTAG | GAGCCATTGA | 240 |
| GAGACTGTTT | GGACATGCCT | GTGTTCATGT | AGCCGTGATG | TCCGGGGGCC | GTGTACATCA | 300 |
| TGTTACCGTG | GGGTGGGGTC | TGCATTGGCT | GCTGGGCATA | TGGCTGGGTG | CCCATCATGC | 360 |
| CCATCTGCAT | CTGCATAGGG | TATTGGGGCG | TTTGATCCAT | ATAGCCATGA | TTGCTGTGGT | 420 |
| AGCCACTGTT | CATCATTGGC | TGGGACATGC | TGTTACCCTC | TTA | | 463 |

(2) INFORMATION FOR SEQ ID NO: 51:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO: 51:

| | | | | | |
|---|---|---|---|---|---|
| CTTCAACCTC | CCAAAGTGCT | GGGATTACAG | GACTGAGCCA | CCACGCTCAG | CCTAAGCCTC | 60 |
| TTTTTCACTA | CCCTCTAAGC | GATCTACCAC | AGTGATGAGG | GGCTAAAGAG | CAGTGCAATT | 120 |
| TGATTACAAT | AATGGAACTT | AGATTATTA | ATTAACAATT | TTTCCTTAGC | ATGTTGGTTC | 180 |
| CATAATTATT | AAGAGTATGG | ACTTACTTAG | AAATGAGCTT | TCATTTTAAG | AATTTCATCT | 240 |
| TTGACCTTCT | CTATTAGTCT | GAGCAGTATG | ACACTATACG | TATTTTATTT | AACTAACCTA | 300 |
| CCTTGAGCTA | TTACTTTTTA | AAAGGCTATA | TACATGAATG | TGTATTGTCA | ACTGTAAAGC | 360 |
| CCCACAGTAT | TTAATTATAT | CATGATGTCT | TTGAGGTTG | | | 399 |

(2) INFORMATION FOR SEQ ID NO: 52:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (xi) SEQUENCE DESCRIPTION: SEQ ID NO: 52:

| | | | | | |
|---|---|---|---|---|---|
| CTTCAACCTC | AATCAACCTT | GGTAATTGAT | AAAATCATCA | CTTAACTTTC | TGATATAATG | 60 |
| GCAATAATTA | TCTGAGAAAA | AAAAGTGGTG | AAAGATTAAA | CTTGCATTTC | TCTCAGAATC | 120 |
| TTGAAGGATA | TTTGAATAAT | TCAAAAGCGG | AATCAGTAGT | ATCAGCCGAA | GAAACTCACT | 180 |
| TAGCTAGAAC | GTTGGACCCA | TGGATCTAAG | TCCCTGCCCT | TCCACTAACC | AGCTGATTGG | 240 |
| TTTTGTGTAA | ACCTCCTACA | CGCTTGGGCT | TGGTCGCCTC | ATTTGTCAAA | GTAAAGGCTG | 300 |
| AAATAGGAAG | ATAATGAACC | GTGTCTTTTT | GGTCTCTTTT | CCATCCATTA | CTCTGATTTT | 360 |
| ACAAAGAGGC | CTGTATTCCC | CTGGTGAGGT | TG | | | 392 |

(2) INFORMATION FOR SEQ ID NO: 53:

(i) SEQUENCE CHARACTERISTICS:
        (A) LENGTH: 179 base pairs (B) TYPE: nucleic acid
        (C) STRANDEDNESS: single
        (D) TOPOLOGY: linear (xi) SEQUENCE DESCRIPTION: SEQ ID NO: 53:

TTCGGGTGAT GCCTCCTCAG GCTACAGTGA AGACTGGATT ACAGAAAGGT GCCAGCGAGA      60

TTTCAGATTC CTGTAAACCT CTAAAGAAAA GGAGTCGCGC CTCAACTGAT GTAGAAATGA     120

CTAGTTCAGC ATACNGAGAC ACNTCTGACT CCGATTCTAG AGGACTGAGT GACCTGCAN     179

(2) INFORMATION FOR SEQ ID NO: 54:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (xi) SEQUENCE DESCRIPTION: SEQ ID NO: 54:

TTCGGGTGAT GCCTCCTCAG GCTACATCAT NATAGAAGCA AAGTAGAANA ATCNNGTTTG      60

TGCATTTTCC CACANACAAA ATTCAAATGA NTGGAAGAAA TTGGGANAGT AT            112

(2) INFORMATION FOR SEQ ID NO: 55:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO: 55:

TGAGCTTCCG CTTCTGACAA CTCAATAGAT AATCAAAGGA CAACTTTAAC AGGGATTCAC      60

AAAGGAGTAT ATCCAAATGC CAATAAACAT ATAAAAAGGA ATTCAGCTTC ATCATCATCA    120

GAAGWATGCA AATTAAAAACC ATAATGAGAA ACCACTATGT CCCACTAGAA TAGATAAAAT    180

CTTAAAAGAC TGGTAAAACC AAGTGTTGGT AAGGCAAGAG GAGCA                    225

(2) INFORMATION FOR SEQ ID NO: 56:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (xi) SEQUENCE DESCRIPTION: SEQ ID NO: 56:

GCTCCTCTTG CCTTACCAAC ACATTCTCAA AAACCTGTTA GAGTCCTAAG CATTCTCCTG      60

TTAGTATTGG GATTTTACCC CTGTCCTATA AAGATGTTAT GTACCAAAAA TGAAGTGGAG    120

GGCCATACCC TGAGGGAGGG GAGGGATCTC TAGTGTTGTC AGAAGCGGAA GCTCA         175

(2) INFORMATION FOR SEQ ID NO: 57:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (xi) SEQUENCE DESCRIPTION: SEQ ID NO: 57:

AGCCATTTAC CACCCATGGA TGAATGGATT TTGTAATTCT AGCTGTTGTA TTTTGTGAAT      60

TTGTTAATTT TGTTGTTTTT CTGTGAAACA CATACATTGG ATATGGGAGG TAAAGGAGTG    120

TCCCAGTTGC TCCTGGTCAC TCCCTTTATA GCCATTACTG TCTTGTTTCT TGTAACTCAG    180

GTTAGGTTTT GGTCTCTCTT GCTCCACTGC AAAAAAAAAA AAA                          223

(2) INFORMATION FOR SEQ ID NO: 58:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (xi) SEQUENCE DESCRIPTION: SEQ ID NO: 58:

GTTCGAAGGT GAACGTGTAG GTAGCGGATC TCACAACTGG GGAACTGTCA AAGACGAATT          60

AACTGACTTG GATCAATCAA ATGTGACTGA GGAAACACCT GAAGGTGAAG AACATCATCC         120

AGTGGCAGAC ACTGAAAATA GGAGAATGA AGTTGAAGAG GTAAAGAGG AGGGTCCAAA          180

AGAGATGACT TTGGATGGGT GGTAAATGGC T                                      211

(2) INFORMATION FOR SEQ ID NO: 59:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO: 59:

GCTCCTCTTG CCTTACCAAC TTTGCACCCA TCATCAACCA TGTGGCCAGG TTTGCAGCCC          60

AGGCTGCACA TCAGGGGACT GCCTCGCAAT ACTTCATGCT GTTGCTGCTG ACTGATGGTG         120

CTGTGACGGA TGTGGAAGCC ACACGTGAGG CTGTGGTGCG TGCCTCGAAC CTGCCCATGT         180

CAGTGATCAT TATGGGTGGT AAATGGCT                                          208

(2) INFORMATION FOR SEQ ID NO: 60:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (xi) SEQUENCE DESCRIPTION: SEQ ID NO: 60:

AGCCATTTAC CACCCATACT AAATTCTAGT TCAAACTCCA ACTTCTTCCA TAAAACATCT          60

AACCACTGAC ACCAGTTGGC AATAGCTTCT TCCTTCTTTA ACCTCTTAGA GTATTTATGG        120

TCAATGCCAC ACATTTCTGC AACTGAATAA AGTTGGTAAG GCAAGAGGAG C                 171

(2) INFORMATION FOR SEQ ID NO: 61:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO: 61:

CGGGTGATGC CTCCTCAGGC TTTGGTGTGT CCACTCNACT CACTGGCCTC TTCTCCAGCA          60

ACTGGTGAAN ATGTCCTCAN GAAAANCNCC ACACGCNGCT CAGGGTGGGG TGGGAANCAT         120

CANAATCATC NGGC                                                         134

(2) INFORMATION FOR SEQ ID NO: 62:

(i) SEQUENCE CHARACTERISTICS:

(A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO: 62:

AGAGGGTACA TATGCAACAG TATATAAAGG AAGAAGTGCA CTGAGAGGAA CTTCATCAAG      60

GCCATTTAAT CAATAAGTGA TAGAGTCAAG GCTCAACCCA GGTGTGACGG ATTCCAGGTC     120

CCAAGCTCCT TACTGGTACC CTCTT                                          145

(2) INFORMATION FOR SEQ ID NO: 63:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO: 63:

TGCACTGAGA GGAATTCAAA GGGTTTATGC CAAAGAACAA ACCAGTCCTC TGCAGCCTAA      60

CTCATTTGTT TTTGGGCTGC GAAGCCATGT AGAGGGCGAT CAGGCAGTAG ATGGTCCCTC     120

CCACAGTCAG CGCCATGGTG GTCCGGTAAA GCATTTGGTC AGGCAGGCCT CGTTTCAGGT     180

AGACGGGCAC ACATCAGCTT TCTGGAAAAA CTTTTGTAGC TCTGGAGCTT TGTTTTTCCC     240

AGCATAATCA TACACTGTGG AATCGGAGGT CAGTTTAGTT GGTAAGGCAA GAGGAGC        297

(2) INFORMATION FOR SEQ ID NO: 64:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO: 64:

GCACTGAGAG GAACTTCCAA TACTATGTTG AATAGGAGTG GTGAGAGAGG GCATCCTTGT      60

CTTGTGCCGG TTTTCAAAGG GAATGCTTCC AGCTTTTGCC CATTCAGTAT AATATTAAAG     120

AATGTTTTAC CATTTTCTGT CTTGCCTGTT TTTCTGTGTT TTTGTTGGTC TCTTCATTCT     180

CCATTTTTAG GCCTTTACAT GTTAGGAATA TATTTCTTTT AATGATACTT CACCTTTGGT     240

ATCTTTTGTG AGACTCTACT CATAGTGTGA TAAGCACTGG GTTGGTAAGG CAAGAGGAGC     300

(2) INFORMATION FOR SEQ ID NO: 65:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO: 65:

GCTCCTCTTG CCTTACCAAC TCACCCAGTA TGTCAGCAAT TTTATCRGCT TTACCTACGA      60

AACAGCCTGT ATCCAAACAC TTAACACACT CACCTGAAAA GTTCAGGCAA CAATCGCCTT     120

CTCATGGGTC TCTCTGCTCC AGTTCTGAAC CTTTCTCTTT TCCTAGAACA TGCATTTARG     180

TCGATAGAAG TTCCTCTCAG TGC                                            203

(2) INFORMATION FOR SEQ ID NO: 66:

(i) SEQUENCE CHARACTERISTICS:
        (A) LENGTH: 344 base pairs (B) TYPE: nucleic acid
        (C) STRANDEDNESS: single
        (D) TOPOLOGY: linear (xi) SEQUENCE DESCRIPTION: SEQ ID NO: 66:

TACGGGGACC CCTGCATTGA GAAAGCGAGA CTCACTCTGA AGCTGAAATG CTGTTGCCCT        60

TGCAGTGCTG GTAGCAGGAG TTCTGTGCTT TGTGGGCTAA GGCTCCTGGA TGACCCCTGA       120

CATGGAGAAG GCAGAGTTGT GTGCCCCTTC TCATGGCCTC GTCAAGGCAT CATGGACTGC       180

CACACACAAA ATGCCGTTTT TATTAACGAC ATGAAATTGA AGGAGAGAAC ACAATTCACT       240

GATGTGGCTC GTAACCATGG ATATGGTCAC ATACAGAGGT GTGATTATGT AAAGGTTAAT       300

TCCACCCACC TCATGTGGAA ACTAGCCTCA ATGCAGGGGT CCCA                        344

(2) INFORMATION FOR SEQ ID NO: 67:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (xi) SEQUENCE DESCRIPTION: SEQ ID NO: 67:

GCACTGAGAG GAACTTCGTA GGGAGGTTGA ACTGGCTGCT GAGGAGGGGG AACAACAGGG        60

TAACCAGACT GATAGCCATT GGATGGATAA TATGGTGGTT GAGGAGGGAC ACTACTTATA       120

GCAGAGGGTT GTGTATAGCC TGAGGAGGCA TCACCCG                                157

(2) INFORMATION FOR SEQ ID NO: 68:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO: 68:

GCACTGAGAG GAACTTCTAG AAAGTGAAAG TCTAGACATA AAATAAAATA AAAATTTAAA        60

ACTCAGGAGA GACAGCCCAG CACGGTGGCT CACGCCTGTA ATCCCAGAAC TTTGGGAGCC       120

TGAGGAGGCA TCACCCG                                                     137

(2) INFORMATION FOR SEQ ID NO: 69:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (xi) SEQUENCE DESCRIPTION: SEQ ID NO: 69:

CGGGTGATGC CTCCTCAGGC TGTATTTTGA AGACTATCGA CTGGACTTCT TATCAACTGA        60

AGAATCCGTT AAAAATACCA GTTGTATTAT TTCTACCTGT CAAAATCCAT TTCAAATGTT       120

GAAGTTCCTC TCAGTGC                                                     137

(2) INFORMATION FOR SEQ ID NO: 70:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (xi) SEQUENCE DESCRIPTION: SEQ ID NO: 70:

```
AGCATGTTGA GCCCAGACAC GCAATCTGAA TGAGTGTGCA CCTCAAGTAA ATGTCTACAC      60

GCTGCCTGGT CTGACATGGC ACACCATCNC GTGGAGGGCA CASCTCTGCT CNGCCTACWA     120

CGAGGGCANT CTCATWGACA GGTTCCACCC ACCAAACTGC AAGAGGCTCA NNAAGTACTR     180

CCAGGGTMYA SGGACMASGG TGGGAYTYCA YCACWCATCT                           220
```

(2) INFORMATION FOR SEQ ID NO: 71:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (xi) SEQUENCE DESCRIPTION: SEQ ID NO: 71:

```
CGTTAGGGTC TCTATCCACT GCTAAACCAT ACACCTGGGT AAACAGGGAC CATTTAACAT      60

TCCCANCTAA ATATGCCAAG TGACTTCACA TGTTTATCTT AAAGATGTCC AAAACGCAAC     120

TGATTTTCTC CCCTAAACCT GTGATGGTGG GATGATTAAN CCTGAGTGGT CTACAGCAAG     180

TTAAGTGCAA GGTGCTAAAT GAANGTGACC TGAGATACAG CATCTACAAG GCAGTACCTC     240

TCAACNCAGG GCAACTTTGC TTCTCANAGG GCATTTAGCA GTGTCTGAAG TAATTTCTGT     300

ATTACAACTC ACGGGCGGG GGGTGAATAT CTANTGGANA GNAGACCCTA ACG             353
```

(2) INFORMATION FOR SEQ ID NO: 72:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (xi) SEQUENCE DESCRIPTION: SEQ ID NO: 72:

```
GCACTGAGAG GAACTTCCAA TACYATKATC AGAGTGAACA RGCARCCYAC AGAACAGGAG      60

AAAATGTTYG CAATCTCTCC ATCTGACAAA AGGCTAATAT CCAGAWTCTA AWAGGAACTT     120

AAACAAATTT ATGAGAAAAG AACARACAAC CTCAWCAAAA AGTGGGTGAA GGAWATGCTS     180

AAARGAAGAC ATYTATTCAG CCAGTAAACA YATGAAAAAA AGGCTCATSA TCACTGAWCA     240

TTAGAGAAAT GCAAATCAAA ACCACAATGA GATACCATCT YAYRCCAGTT AGAAYGGTGA     300

TCATTAAAAR STCAGGAAAC AACAGATGCT GGACAAGGTG TCA                       343
```

(2) INFORMATION FOR SEQ ID NO: 73:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 73:

```
GCACTGAGAG GAACTTCAGA GAGAGAGAGA GAGTTCCACC CTGTACTTGG GGAGAGAAAC      60

AGAAGGTGAG AAAGTCTTTG GTTCTGAAGC AGCTTCTAAG ATCTTTTCAT TTGCTTCATT     120

TCAAAGTTCC CATGCTGCCA AAGTGCCATC CTTTGGGGTA CTGTTTTCTG AGCTCCAGTG     180

ATAACTCATT TATACAAGGG AGATACCCAG AAAAAAAGTG AGCAAATCTT AAAAAGGTGG     240

CTTGAGTTCA GCCTTAAATA CCATCTTGAA ATGACACAGA GAAAGAANGA TGTTGGGTGG     300

GAGTGGATAG AGACCCTAAC G                                               321
```

(2) INFORMATION FOR SEQ ID NO: 74:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 74:

```
GCACTGAGAG GAACTTCAGA GAGAGAGAGA GAGTTCCACC CTGTACTTGG GGAGAGAAAC      60

AGAAGGTGAG AAAGTCTTTG GTTCTGAAGC AGCTTCTAAG ATCTTTTCAT TTGCTTCATT     120

TCAAAGTTCC CATGCTGCCA AAGTGCCATC CTTTGGGGTA CTGTTTTCTG AGCTCCAGTG     180

ATAACTCATT TATACAAGGG AGATACCCAG AAAAAAAGTG AGCAAATCTT AAAAAGGTGG     240

CTTGAGTTCA GYCTTAAATA CCATCTTGAA ATGAMACAGA GAAAGAAGGA TGTTGGGTGG     300

GAGTGGATAG AGACCCTAAC G                                               321
```

(2) INFORMATION FOR SEQ ID NO: 75:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO: 75:

```
GCACTGAGAG GAACTTCCAC ATGCACTGAG AAATGCATGT TCACAAGGAC TGAAGTCTGG      60

AACTCAGTTT CTCAGTTCCA ATCCTGATTC AGGTGTTTAC CAGCTACACA ACCTTAAGCA     120

AGTCAGATAA CCTTAGCTTC CTCATATGCA AAATGAGAAT GAAAGTACT CATCGCTGAA      180

TTGTTTTGAG GATTAGAAAA ACATCTGGCA TGCAGTAGAA ATTCAATTAG TATTCATTTT     240

CATTCTTCTA AATTAAACAA ATAGGATTTT TAGTGGTGGA ACTTCAGACA CCAGAAATGG     300

GAGTGGATAG AGACCCT                                                    317
```

(2) INFORMATION FOR SEQ ID NO: 76:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (xi) SEQUENCE DESCRIPTION: SEQ ID NO: 76:

```
CGTTAGGGTC TCTATCCACT CCCACTACTG ATCAAACTCT ATTTATTTAA TTATTTTTAT      60

CATACTTTAA GTTCTGGGAT ACACGTGCAG CATGCGCAGG TTTGTTGCAT AGGTATACAC     120

TTGCCATGGT GGTTTGCTGC ACCCATCAGT CCATCATCTA CATTAGGTAT TTCTCCTAAT     180

GCTATCCCTC CCCTAGCCCC TTACACCCCC AACAGGCTCT AGTGTGTGAA GTTCCTCTCA     240

GTGC                                                                  244
```

(2) INFORMATION FOR SEQ ID NO: 77:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO: 77:

```
CGTTAGGGTC TCTATCCACT GAAATCTGAA GCACAGGAGG AAGAGAAGCA GTYCTAGTGA      60
```

```
GATGGCAAGT TCWTTTACCA CACTCTTTAA CATTTYGTTT AGTTTTAACC TTTATTTATG      120

GATAATAAAG GTTAATATTA ATAATGATTT ATTTTAAGGC ATTCCCRAAT TTGCATAATT      180

CTCCTTTTGG AGATACCCTT TTATCTCCAG TGCAAGTCTG GATCAAAGTG ATASAMAGAA      240

GTTCCTCTCA GTGC                                                       254

(2) INFORMATION FOR SEQ ID NO: 78:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO: 78:

TTCGATACAG GCAAACATGA ACTGCAGGAG GGTGGTGACG ATCATGATGT TGCCGATGGT       60

CCGGATGGNC ACGAAGACGC ACTGGANCAC GTGCTTACGT CCTTTTGCTC TGTTGATGGC      120

CCTGAGGGGA CGCAGGACCC TTATGACCCT CAGAATCTTC ACAACGGGAG ATGGCACTGG      180

ATTGANTCCC ANTGACACCA GAGACACCCC AACCACCAGN ATATCANTAT ATTGATGTAG      240

TTCCTGTAGA NGGCCCCCTT GTGGAGGAAA GCTCCATNAG TTGGTCATCT TCAACAGGAT      300

CTCAACAGTT TCCGATGGCT GTGATGGGCA TAGTCATANT TAACCNTGTN TCGAA           355

(2) INFORMATION FOR SEQ ID NO: 79:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO: 79:

TAAGAGGGTA CCAGCAGAAA GGTTAGTATC ATCAGATAGC ATCTTATACG AGTAATATGC       60

CTGCTATTTG AAGTGTAATT GAGAAGGAAA ATTTTAGCGT GCTCACTGAC CTGCCTGTAG      120

CCCCAGTGAC AGCTAGGATG TGCATTCTCC AGCCATCAAG AGACTGAGTC AAGTTGTTCC      180

TTAAGTCAGA ACAGCAGACT CAGCTCTGAC ATTCTGATTC GAATGACACT GTTCAGGAAT      240

CGGAATCCTG TCGATTAGAC TGGACAGCTT GTGGCAAGTG AATTTGCCTG TAACAAGCCA      300

GATTTTTTAA AATTTATATT GTAAATAATG TGTGTGTGTG TGTGTGTATA TATATATATA      360

TGTACAGTTA TCTAAGTTAA TTTAAAAGTT GTTTGGTACC CTCTTA                    406

(2) INFORMATION FOR SEQ ID NO: 80:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (xi) SEQUENCE DESCRIPTION: SEQ ID NO: 80:

TTTTTTTTTT TTTACTCGGC TCAGTCTAAT CCTTTTTGTA GTCACTCATA GGCCAGACTT       60

AGGGCTAGGA TGATGATTAA TAAGAGGGAT GACATAACTA TTAGTGGCAG GTTAGTTGTT      120

TGTAGGGCTC ATGGTAGGGG TAAAAGGAGG GCAATTTCTA GATCAAATAA TAAGAAGGTA      180

ATAGCTACTA AGAAGAATTT TATGGAGAAA GGGACGCGGG CGGGGGATAT AGGGTCGAAG      240

CCGCACTCGT AAGGGGTGGA TTTTTCTATG TAGCCGTTGA GTTGTGGTAG TCAAAATGTA      300

ATAATTATTA GTAGTAAGCC TAGGAGA                                         327
```

(2) INFORMATION FOR SEQ ID NO: 81:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO: 81:

```
TAGTCTATGC GGTTGATTCG GCAATCCATT ATTTGCTGGA TTTTGTCATG TGTTTTGCCA      60

ATTGCATTCA TAATTTATTA TGCATTTATG CTTGTATCTC CTAAGTCATG GTATATAATC     120

CATGCTTTTT ATGTTTTGTC TGACATAAAC TCTTATCAGA GCCCTTTGCA CACAGGGATT     180

CAATAAATAT TAACACAGTC TACATTTATT TGGTGAATAT TGCATATCTG CTGTACTGAA     240

AGCACATTAA GTAACAAAGG CAAGTGAGAA GAATGAAAAG CACTACTCAC AACAGTTATC     300

ATGATTGCGC ATAGACTA                                                   318
```

(2) INFORMATION FOR SEQ ID NO: 82:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO: 82:

```
TCTTCAACCT CTACTCCCAC TAATAGCTTT TTGATGACTT CTAGCAAGCC TCGCTAACCT      60

CGCCTTACCC CCCACTATTA ACCTACTGGG AGAACTCTCT GTGCTAGTAA CCACGTTCTC     120

CTGATCAAAT ATCACTCTCC TACTTACAGG ACTCAACATA CTAGTCACAG CCCTATACTC     180

CCTCTACATA TTTACCACAA CACAATGGGG CTCACTCACC CACCACATTA ACAACATAAA     240

ACCCTCATTC ACACGAGAAA ACACCCTCAT GTTCATACAC CTATCCCCCA TTCTCCTCCT     300

ATCCCTCAAC CCCGACATCA TTACCGGGTT TTCCTCTT                             338
```

(2) INFORMATION FOR SEQ ID NO: 83:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 83:

```
AGCCATTTAC CACCCATCCA CAAAAAAAAA AAAAAAAAAG AAAAATATCA AGGAATAAAA      60

ATAGACTTTG AACAAAAAGG AACATTTGCT GGCCTGAGGA GGCATCACCC G              111
```

(2) INFORMATION FOR SEQ ID NO: 84:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (xi) SEQUENCE DESCRIPTION: SEQ ID NO: 84:

```
TCGGGTGATG CCTCCTCAGG CCAAGAAGAT AAAGCTTCAG ACCCCTAACA CATTTCCAAA      60

AAGGAAGAAA GGAGAAAAAA GGGCATCATC CCCGTTCCGA AGGGTCAGGG AGGAGGAAAT     120

TGAGGTGGAT TCACGAGTTG CGGACAACTC CTTTGATGCC AAGCGAGGTG CAGCCGGAGA     180

CTGGGGAGAG CGAGCCAATC AGGTTTTGAA GTTCCTCTCA GTGC                      224
```

(2) INFORMATION FOR SEQ ID NO: 85:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (xi) SEQUENCE DESCRIPTION: SEQ ID NO: 85:

```
GCACTGAGAG GAACTTCGTT GGAAACGGGT TTTTTTCATG TAAGGCTAGA CAGAAGAATT      60

CTCAGTAACT TCCTTGTGTT GTGTGTATTC AACTCACASA GTTGAACGAT CCTTTACACA     120

GAGCAGACTT GTAACACTCT TWTTGTGGAA TTTGCAAGTG GAGATTTCAG SCGCTTTGAA     180

GTSAAAGGTA GAAAAGGAAA TATCTTCCTA TAAAAACTAG ACAGAATGAT TCTCAGAAAC     240

TCCTTTGTGA TGTGTGCGTT CAACTCACAG AGTTTAACCT TTCWTTTCAT AGAAGCAGTT     300

AGGAAACACT CTGTTTGTAA AGTCTGCAAG TGGATAGAGA CCCTAACG                  348
```

(2) INFORMATION FOR SEQ ID NO: 86:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (xi) SEQUENCE DESCRIPTION: SEQ ID NO: 86:

```
GCACTGAGAG GAACTTCYTT GTGWTGTKTG YATTCAACTC ACAGAGTTGA ASSWTSMTTT      60

ACABAGWKCA GGCTTKCAAA CACTCTTTTT GTMGAATYTG CAAGWGGAKA TTTSRRCCRC     120

TTTGWGGYCW WYSKTMGAAW MGGRWATATC TTCWYATMRA AMCTAGACAG AAKSATTCTC     180

AKAAWSTYYY YTGTGAWGWS TGCRTTCAAC TCACAGAGKT KAACMWTYCT KYTSATRGAG     240

CAGTTWKGAA ACTCTMTTTC TTTGGATTCT GCAAGTGGAT AGAGACCCTA ACG            293
```

(2) INFORMATION FOR SEQ ID NO: 87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 87:

```
CTCCTAGGCT                                                             10
```

(2) INFORMATION FOR SEQ ID NO: 88:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 88:

```
AGTAGTTGCC                                                             10
```

(2) INFORMATION FOR SEQ ID NO: 89:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO: 89:

TTCCGTTATG C                                                                                    11

(2) INFORMATION FOR SEQ ID NO: 90:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 90:

TGGTAAAGGG                                                                                      10

(2) INFORMATION FOR SEQ ID NO: 91:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 91:

TCGGTCATAG                                                                                      10

(2) INFORMATION FOR SEQ ID NO: 92:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 92:

TACAACGAGG                                                                                      10

(2) INFORMATION FOR SEQ ID NO: 93:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 93:

TGGATTGGTC                                                                                      10

(2) INFORMATION FOR SEQ ID NO: 94:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 94:

CTTTCTACCC                                                                                      10

(2) INFORMATION FOR SEQ ID NO: 95:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO: 95:

TTTTGGCTCC                                                                                              10

(2) INFORMATION FOR SEQ ID NO: 96:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 96:

GGAACCAATC                                                                                              10

(2) INFORMATION FOR SEQ ID NO: 97:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 97:

TCGATACAGG                                                                                              10

(2) INFORMATION FOR SEQ ID NO: 98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 98:

GGTACTAAGG                                                                                              10

(2) INFORMATION FOR SEQ ID NO: 99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 99:

AGTCTATGCG                                                                                              10

(2) INFORMATION FOR SEQ ID NO: 100:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 100:

CTATCCATGG                                                                                              10

(2) INFORMATION FOR SEQ ID NO: 101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 101:

TCTGTCCACA                                                              10

(2) INFORMATION FOR SEQ ID NO: 102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 102:

AAGAGGGTAC                                                              10

(2) INFORMATION FOR SEQ ID NO: 103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 103:

CTTCAACCTC                                                              10

(2) INFORMATION FOR SEQ ID NO: 104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 104:

GCTCCTCTTG CCTTACCAAC                                                   20

(2) INFORMATION FOR SEQ ID NO: 105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 105:

GTAAGTCGAG CAGTGTGATG                                                   20

(2) INFORMATION FOR SEQ ID NO: 106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 106:

GTAAGTCGAG CAGTCTGATG                                                   20

(2) INFORMATION FOR SEQ ID NO: 107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 107:

GACTTAGTGG AAAGAATGTA                                          20

(2) INFORMATION FOR SEQ ID NO: 108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 108:

GTAATTCCGC CAACCGTAGT                                          20

(2) INFORMATION FOR SEQ ID NO: 109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 109:

ATGGTTGATC GATAGTGGAA                                          20

(2) INFORMATION FOR SEQ ID NO: 110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 110:

ACGGGGACCC CTGCATTGAG                                          20

(2) INFORMATION FOR SEQ ID NO: 111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 111:

TATTCTAGAC CATTCGCTAC                                          20

(2) INFORMATION FOR SEQ ID NO: 112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 112:

ACATAACCAC TTTAGCGTTC                                          20

(2) INFORMATION FOR SEQ ID NO: 113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 113:

CGGGTGATGC CTCCTCAGGC                                          20

(2) INFORMATION FOR SEQ ID NO: 114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 114:

AGCATGTTGA GCCCAGACAC                                    20

(2) INFORMATION FOR SEQ ID NO: 115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 115:

GACACCTTGT CCAGCATCTG                                    20

(2) INFORMATION FOR SEQ ID NO: 116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 116:

TACGCTGCAA CACTGTGGAG                                    20

(2) INFORMATION FOR SEQ ID NO: 117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 117:

CGTTAGGGTC TCTATCCACT                                    20

(2) INFORMATION FOR SEQ ID NO: 118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 118:

AGACTGACTC ATGTCCCCTA                                    20

(2) INFORMATION FOR SEQ ID NO: 119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 119:

TCATCGCTCG GTGACTCAAG                                    20

(2) INFORMATION FOR SEQ ID NO: 120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 120:

CAAGATTCCA TAGGCTGACC                                                    20

(2) INFORMATION FOR SEQ ID NO: 121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 121:

ACGTACTGGT CTTGAAGGTC                                                    20

(2) INFORMATION FOR SEQ ID NO: 122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 122:

GACGCTTGGC CACTTGACAC                                                    20

(2) INFORMATION FOR SEQ ID NO: 123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 123:

GTATCGACGT AGTGGTCTCC                                                    20

(2) INFORMATION FOR SEQ ID NO: 124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 124:

TAGTGACATT ACGACGCTGG                                                    20

(2) INFORMATION FOR SEQ ID NO: 125:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 125:

CGGGTGATGC CTCCTCAGGC                                                    20

(2) INFORMATION FOR SEQ ID NO: 126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 126:

ATGGCTATTT TCGGGGGCTG ACA        23

(2) INFORMATION FOR SEQ ID NO: 127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 127:

CCGGTATCTC CTCGTGGGTA TT        22

(2) INFORMATION FOR SEQ ID NO: 128:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 128:

CTGCCTGAGC CACAAATG        18

(2) INFORMATION FOR SEQ ID NO: 129:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 129:

CCGGAGGAGG AAGCTAGAGG AATA        24

(2) INFORMATION FOR SEQ ID NO: 130:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 130:

TTTTTTTTTT TTAG        14

(2) INFORMATION FOR SEQ ID NO: 131:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 131:

Ser Ser Gly Gly Arg Thr Phe Asp Asp Phe His Arg Tyr Leu Leu Val
1               5                   10                15

Gly Ile (2) INFORMATION FOR SEQ ID NO: 132:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 132:

Gln Gly Ala Ala Gln Lys Pro Ile Asn Leu Ser Lys Xaa Ile Glu Val
1             5                  10               15

Val Gln Gly His Asp Glu
          20

(2) INFORMATION FOR SEQ ID NO: 133:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 133:

Ser Pro Gly Val Phe Leu Glu His Leu Gln Glu Ala Tyr Arg Ile Tyr
1             5                  10               15

Thr Pro Phe Asp Leu Ser Ala
          20

(2) INFORMATION FOR SEQ ID NO: 134:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 134:

Tyr Leu Leu Val Gly Ile Gln Gly Ala
1             5

(2) INFORMATION FOR SEQ ID NO: 135:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 135:

Gly Ala Ala Gln Lys Pro Ile Asn Leu
1             5

(2) INFORMATION FOR SEQ ID NO: 136:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 136:

Asn Leu Ser Lys Xaa Ile Glu Val Val
1             5

(2) INFORMATION FOR SEQ ID NO: 137:

(i) SEQUENCE CHARACTERISTICS:
    (A) LENGTH: 9 amino acids
    (B) TYPE: amino acid
    (C) STRANDEDNESS: single
    (D) TOPOLOGY: linear (xi) SEQUENCE DESCRIPTION: SEQ ID NO: 137:

Glu Val Val Gln Gly His Asp Glu Ser
1               5

(2) INFORMATION FOR SEQ ID NO: 138:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 138:

His Leu Gln Glu Ala Tyr Arg Ile Tyr
1               5

(2) INFORMATION FOR SEQ ID NO: 139:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 139:

Asn Leu Ala Phe Val Ala Gln Ala Ala
1               5

(2) INFORMATION FOR SEQ ID NO: 140:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 140:

Phe Val Ala Gln Ala Ala Pro Asp Ser
1               5

(2) INFORMATION FOR SEQ ID NO: 141:

(i) SEQUENCE CHARACTERISTICS:
        (A) LENGTH: 9388 base pairs
        (B) TYPE: nucleic acid
        (C) STRANDEDNESS: single
        (D) TOPOLOGY: linear (xi) SEQUENCE DESCRIPTION: SEQ ID NO: 141:

```
GCTCGCGGCC GCGAGCTCAA TTAACCCTCA CTAAAGGGAG TCGACTCGAT CAGACTGTTA     60

CTGTGTCTAT GTAGAAAGAA GTAGACATAA GAGATTCCAT TTTGTTCTGT ACTAAGAAAA    120

ATTCTTCTGC CTTGAGATGC TGTTAATCTG TAACCCTAGC CCCAACCCTG TGCTCACAGA    180

GACATGTGCT GTGTTGACTC AAGGTTCAAT GGATTTAGGG CTATGCTTTG TTAAAAAAGT    240

GCTTGAAGAT AATATGCTTG TTAAAAGTCA TCACCATTCT CTAATCTCAA GTACCCAGGG    300

ACACAATACA CTGCGGAAGG CCGCAGGGAC CTCTGTCTAG GAAAGCCAGG TATTGTCCAA    360

GATTTCTCCC CATGTGATAG CCTGAGATAT GGCCTCATGG GAAGGGTAAG ACCTGACTGT    420
```

```
CCCCCAGCCC GACATCCCCC AGCCCGACAT CCCCCAGCCC GACACCCGAA AAGGGTCTGT    480

GCTGAGGAGG ATTAGTAAAA GAGGAAGGCC TCTTTGCAGT TGAGGTAAGA GGAAGGCATC    540

TGTCTCCTGC TCGTCCCTGG GCAATAGAAT GTCTTGGTGT AAAACCCGAT TGTATGTTCT    600

ACTTACTGAG ATAGGAGAAA ACATCCTTAG GGCTGGAGGT GAGACACGCT GGCGGCAATA    660

CTGCTCTTTA ATGCACCGAG ATGTTTGTAT AAGTGCACAT CAAGGCACAG CACCTTTCCT    720

TAAACTTATT TATGACACAG AGACCTTTGT TCACGTTTTC CTGCTGACCC TCTCCCCACT    780

ATTACCCTAT TGGCCTGCCA CATCCCCCTC TCCGAGATGG TAGAGATAAT GATCAATAAA    840

TACTGAGGGA ACTCAGAGAC CAGTGTCCCT GTAGGTCCTC CGTGTGCTGA GCGCCGGTCC    900

CTTGGGCTCA CTTTTCTTTC TCTATACTTT GTCTCTGTGT CTCTTTCTTT TCTCAGTCTC    960

TCGTTCCACC TGACGAGAAA TACCCACAGG TGTGGAGGGG CAGGCCACCC CTTCAATAAT   1020

TTACTAGCCT GTTCGCTGAC AACAAGACTG GTGGTGCAGA AGGTTGGGTC TTGGTGTTCA   1080

CCGGGTGGCA GGCATGGGCC AGGTGGGAGG GTCTCCAGCG CCTGGTGCAA ATCTCCAAGA   1140

AAGTGCAGGA AACAGCACCA AGGGTGATTG TAAATTTTGA TTTGGCGCGG CAGGTAGCCA   1200

TTCCAGCGCA AAAATGCGCA GGAAAGCTTT TGCTGTGCTT GTAGGCAGGT AGGCCCCAAG   1260

CACTTCTTAT TGGCTAATGT GGAGGGAACC TGCACATCCA TTGGCTGAAA TCTCCGTCTA   1320

TTTGAGGCTG ACTGAGCGCG TTCCTTTCTT CTGTGTTGCC TGGAAACGGA CTGTCTGCCT   1380

AGTAACATCT GATCACGTTT CCCATTGGCC GCCGTTTCCG GAAGCCCGCC CTCCCATTTC   1440

CGGAAGCCTG GCGCAAGGTT GGTCTGCAGG TGGCCTCCAG GTGCAAAGTG GGAAGTGTGA   1500

GTCCTCAGTC TTGGGCTATT CGGCCACGTG CCTGCCGGAC ATGGGACGCT GGAGGGTCAG   1560

CAGCGTGGAG TCCTGGCCTT TTGCGTCCAC GGGTGGGAAA TTGGCCATTG CCACGGCGGG   1620

AACTGGGACT CAGGCTGCCC CCCGGCCGTT TCTCATCCGT CCACCGGACT CGTGGGCGCT   1680

CGCACTGGCG CTGATGTAGT TTCCTGACCT CTGACCCGTA TTGTCTCCAG ATTAAAGGTA   1740

AAAACGGGGC TTTTTCAGCC CACTCGGGTA AAACGCCTTT TGATTTCTAG GCAGGTGTTT   1800

TGTTGCACGC CTGGGAGGGA GTGACCCGCA GGTTGAGGTT TATTAAAATA CATTCCTGGT   1860

TTATGTTATG TTTATAATAA AGCACCCCAA CCTTTACAAA ATCTCACTTT TGCCAGTTG    1920

TATTATTTAG TGGACTGTCT CTGATAAGGA CAGCCAGTTA AAATGGAATT TTGTTGTTGC   1980

TAATTAAACC AATTTTTAGT TTTGGTGTTT GTCCTAATAG CAACAACTTC TCAGGCTTTA   2040

TAAAACCATA TTTCTTGGGG GAAATTTCTG TGTAAGGCAC AGCAGTTAG TTTGGAATTG    2100

TTTTAAAGGA AGTAAGTTCC TGGTTTTGAT ATCTTAGTAG TGTAATGCCC AACCTGGTTT   2160

TTACTAACCC TGTTTTTAGA CTCTCCCTTT CCTTAAATCA CCTAGCCTTG TTTCCACCTG   2220

AATTGACTCT CCCTTAGCTA AGAGCGCCAG ATGGACTCCA TCTTGGCTCT TTCACTGGCA   2280

GCCCCTTCCT CAAGGACTTA ACTTGTGCAA GCTGACTCCC AGCACATCCA AGAATGCAAT   2340

TAACTGTTAA GATACTGTGG CAAGCTATAT CCGCAGTTCC GAGGAATTCA TCCGATTGAT   2400

TATGCCCAAA AGCCCCGCGT CTATCACCTT GTAATAATCT TAAAGCCCCT GCACCTGGAA   2460

CTATTAACTT TCCTGTAACC ATTTATCCTT TTAACTTTTT TGCTTACTTT ATTTCTGTAA   2520

AATTGTTTTA ACTAGACCTC CCCTCCCCTT TCTAAACCAA AGTATAAAAG AAGATCTAGC   2580

CCCTTCTTCA GAGCGGAGAG AATTTTGAGC ATTAGCCATC TCTTGGCGGC CAGCTAAATA   2640

AATGGACTTT TAATTTGTCT CAAAGTGTGG CGTTTTCTCT AACTCGCTCA GGTACGACAT   2700

TTGGAGGCCC CAGCGAGAAA CGTCACCGGG AGAAACGTCA CCGGGCGAGA GCCGGGCCCG   2760

CTGTGTGCTC CCCCGGAAGG ACAGCCAGCT TGTAGGGGGG AGTGCCACCT GAAAAAAAAA   2820
```

```
TTTCCAGGTC CCCAAAGGGT GACCGTCTTC CGGAGGACAG CGGATCGACT ACCATGCGGG    2880

TGCCCACCAA AATTCCACCT CTGAGTCCTC AACTGCTGAC CCCGGGGTCA GGTAGGTCAG    2940

ATTTGACTTT GGTTCTGGCA GAGGGAAGCG ACCCTGATGA GGGTGTCCCT CTTTTGACTC    3000

TGCCCATTTC TCTAGGATGC TAGAGGGTAG AGCCCTGGTT TTCTGTTAGA CGCCTCTGTG    3060

TCTCTGTCTG GGAGGGAAGT GGCCCTGACA GGGGCCATCC CTTGAGTCAG TCCACATCCC    3120

AGGATGCTGG GGGACTGAGT CCTGGTTTCT GGCAGACTGG TCTCTCTCTC TCTCTTTTTC    3180

TATCTCTAAT CTTTCCTTGT TCAGGTTTCT TGGAGAATCT CTGGGAAAGA AAAAAGAAAA    3240

ACTGTTATAA ACTCTGTGTG AATGGTGAAT GAATGGGGGA GGACAAGGGC TTGCGCTTGT    3300

CCTCCAGTTT GTAGCTCCAC GGCGAAAGCT ACGGAGTTCA AGTGGGCCCT CACCTGCGGT    3360

TCCGTGGCGA CCTCATAAGG CTTAAGGCAG CATCCGGCAT AGCTCGATCC GAGCCGGGGG    3420

TTTATACCGG CCTGTCAATG CTAAGAGGAG CCCAAGTCCC CTAAGGGGGA GCGGCCAGGC    3480

GGGCATCTGA CTGATCCCAT CACGGGACCC CCTCCCCTTG TTTGTCTAAA AAAAAAAAA    3540

GAAGAAACTG TCATAACTGT TTACATGCCC TAGGGTCAAC TGTTTGTTTT ATGTTTATTG    3600

TTCTGTTCGG TGTCTATTGT CTTGTTTAGT GGTTGTCAAG GTTTTGCATG TCAGGACGTC    3660

GATATTGCCC AAGACGTCTG GGTAAGAACT TCTGCAAGGT CCTTAGTGCT GATTTTTTGT    3720

CACAGGAGGT TAAATTTCTC ATCAATCATT TAGGCTGGCC ACCACAGTCC TGTCTTTTCT    3780

GCCAGAAGCA AGTCAGGTGT TGTTACGGGA ATGAGTGTAA AAAACATTC GCCTGATTGG     3840

GATTTCTGGC ACCATGATGG TTGTATTTAG ATTGTCATAC CCCACATCCA GGTTGATTGG    3900

ACCTCCTCTA AACTAAACTG GTGGTGGGTT CAAAACAGCC ACCCTGCAGA TTTCCTTGCT    3960

CACCTCTTTG GTCATTCTGT AACTTTTCCT GTGCCCTTAA ATAGCACACT GTGTAGGGAA    4020

ACCTACCCTC GTACTGCTTT ACTTCGTTTA GATTCTTACT CTGTTCCTCT GTGGCTACTC    4080

TCCCATCTTA AAAACGATCC AAGTGGTCCT TTTCCTCCTC CCTGCCCCCT ACCCCACACA    4140

TCTCGTTTTC CAGTGCGACA GCAAGTTCAG CGTCTCCAGG ACTTGGCTCT GCTCTCACTC    4200

CTTGAACCCT TAAAAGAAAA AGCTGGGTTT GAGCTATTTG CCTTTGAGTC ATGGAGACAC    4260

AAAAGGTATT TAGGGTACAG ATCTAGAAGA AGAGAGAGAA CACCTAGATC CAACTGACCC    4320

AGGAGATCTC GGGCTGGCCT CTAGTCCTCC TCCCTCAATC TTAAAGCTAC AGTGATGTGG    4380

CAAGTGGTAT TTAGCTGTTG TGGTTTTTCT GCTCTTTCTG GTCATGTTGA TTCTGTTCTT    4440

TCGATACTCC AGCCCCCCAG GGAGTGAGTT TCTCTGTCTG TGCTGGGTTT GATATCTATG    4500

TTCAAATCTT ATTAAATTGC CTTCAAAAAA AAAAAAAAA GGGAAACACT TCCTCCCAGC     4560

CTTGTAAGGG TTGGAGCCCT CTCCAGTATA TGCTGCAGAA TTTTTCTCTC GGTTTCTCAG    4620

AGGATTATGG AGTCCGCCTT AAAAAAGGCA AGCTCTGGAC ACTCTGCAAA GTAGAATGGC    4680

CAAAGTTTGG AGTTGAGTGG CCCCTTGAAG GGTCACTGAA CCTCACAATT GTTCAAGCTG    4740

TGTGGCGGGT TGTTACTGAA ACTCCCGGCC TCCCTGATCA GTTTCCCTAC ATTGATCAAT    4800

GGCTGAGTTT GGTCAGGAGC ACCCCTTCCA TGGCTCCACT CATGCACCAT TCATAATTTT    4860

ACCTCCAAGG TCCTCCTGAG CCAGACCGTG TTTTCGCCTC GACCCTCAGC CGGTTCAGCT    4920

CGCCCTGTAC TGCCTCTCTC TGAAGAAGAG GAGAGTCTCC CTCACCCAGT CCCACCGCCT    4980

TAAAACCAGC CTACTCCCTT AGGGTCATCC CATGTCTCCT CGGCTATGTC CCTGTAGGC    5040

TCATCACCCA TTGCCTCTTG GTTGCAACCG TGGTGGGAGG AAGTAGCCCC TCTACTACCA    5100

CTGAGAGAGG CACAAGTCCC TCTGGGTGAT GAGTGCTCCA CCCCCTTCCT GGTTTATGTC    5160
```

```
CCTTCTTTCT ACTTCTGACT TGTATAATTG GAAAACCCAT AATCCTCCCT TCTCTGAAAA    5220

GCCCCAGGCT TTGACCTCAC TGATGGAGTC TGTACTCTGG ACACATTGGC CCACCTGGGA    5280

TGACTGTCAA CAGCTCCTTT TGACCCTTTT CACCTCTGAA GAGAGGGAAA GTATCCAAAG    5340

AGAGGCCAAA AAGTACAACC TCACATCAAC CAATAGGCCG GAGGAGGAAG CTAGAGGAAT    5400

AGTGATTAGA GACCCAATTG GGACCTAATT GGGACCCAAA TTTCTCAAGT GGAGGGAGAA    5460

CTTTTGACGA TTTCCACCGG TATCTCCTCG TGGGTATTCA GGGAGCTGCT CAGAAACCTA    5520

TAAACTTGTC TAAGGCGACT GAAGTCGTCC AGGGGCATGA TGAGTCACCA GGAGTGTTTT    5580

TAGAGCACCT CCAGGAGGCT TATCGGATTT ACACCCCTTT TGACCTGGCA GCCCCCGAAA    5640

ATAGCCATGC TCTTAATTTG GCATTTGTGG CTCAGGCAGC CCCAGATAGT AAAAGGAAAC    5700

TCCAAAAACT AGAGGGATTT TGCTGGAATG AATACCAGTC AGCTTTTAGA GATAGCCTAA    5760

AAGGTTTTTG ACAGTCAAGA GGTTGAAAAA CAAAAACAAG CAGCTCAGGC AGCTGAAAAA    5820

AGCCACTGAT AAAGCATCCT GGAGTATCAG AGTTTACTGT TAGATCAGCC TCATTTGACT    5880

TCCCCTCCCA CATGGTGTTT AAATCCAGCT ACACTACTTC CTGACTCAAA CTCCACTATT    5940

CCTGTTCATG ACTGTCAGGA ACTGTTGGAA ACTACTGAAA CTGGCCGACC TGATCTTCAA    6000

AATGTGCCCC TAGGAAAGGT GGATGCCACC GTGTTCACAG ACAGTAGCAG CTTCCTCGAG    6060

AAGGGACTAC GAAAGGCCGG TGCAGCTGTT ACCATGGAGA CAGATGTGTT GTGGGCTCAG    6120

GCTTTACCAG CAAACACCTC AGCACAAAAG GCTGAATTGA TCGCCCTCAC TCAGGCTCTC    6180

CGATGGGGTA AGGATATTAA CGTTAACACT GACAGCAGGT ACGCCTTTGC TACTGTGCAT    6240

GTACGTGGAG CCATCTACCA GGAGCGTGGG CTACTCACCT CAGCAGGTGG CTGTAATCCA    6300

CTGTAAAGGA CATCAAAAGG AAAACACGGC TGTTGCCCGT GGTAACCAGA AAGCTGATTC    6360

AGCAGCTCAA GATGCAGTGT GACTTTCAGT CACGCCTCTA AACTTGCTGC CCACAGTCTC    6420

CTTTCCACAG CCAGATCTGC CTGACAATCC CGCATACTCA ACAGAAGAAG AAAACTGGCC    6480

TCAGAACTCA GAGCCAATAA AAATCAGGAA GGTTGGTGGA TTCTTCCTGA CTCTAGAATC    6540

TTCATACCCC GAACTCTTGG GAAAACTTTA ATCAGTCACC TACAGTCTAC CACCCATTTA    6600

GGAGGAGCAA AGCTACCTCA GCTCCTCCGG AGCCGTTTTA AGATCCCCCA TCTTCAAAGC    6660

CTAACAGATC AAGCAGCTCT CCGGTGCACA ACCTGCGCCC AGGTAAATGC CAAAAAAGGT    6720

CCTAAACCCA GCCCAGGCCA CCGTCTCCAA GAAAACTCAC CAGGAGAAAA GTGGGAAATT    6780

GACTTTACAG AAGTAAAACC ACACCGGGCT GGGTACAAAT ACCTTCTAGT ACTGGTAGAC    6840

ACCTTCTCTG GATGGACTGA AGCATTTGCT ACCAAAAACG AAACTGTCAA TATGGTAGTT    6900

AAGTTTTTAC TCAATGAAAT CATCCCTCGA CGTGGGCTGC CTGTTGCCAT AGGGTCTGAT    6960

AATGGACCGG CCTTCGCCTT GTCTATAGTT TAGTCAGTCA GTAAGGCGTT AAACATTCAA    7020

TGGAAGCTCC ATTGTGCCTA TCGACCCCAG AGCTCTGGGC AAGTAGAACG CATGAACTGC    7080

ACCCTAAAAA ACACTCTTAC AAAATTAATC TTAGAAACCG GTGTAAATTG TGTAAGTCTC    7140

CTTCCTTTAG CCCTACTTAG AGTAAGGTGC ACCCCTTACT GGGCTGGGTT CTTACCTTTT    7200

GAAATCATGT ATGGGAGGGC GCTGCCTATC TTGCCTAAGC TAAGAGATGC CCAATTGGCA    7260

AAAATATCAC AAACTAATTT ATTACAGTAC CTACAGTCTC CCCAACAGGT ACAAGATATC    7320

ATCCTGCCAC TTGTTCGAGG AACCCATCCC AATCCAATTC CTGAACAGAC AGGGCCCTGC    7380

CATTCATTCC CGCCAGGTGA CCTGTTGTTT GTTAAAAAGT TCCAGAGAGA AGGACTCCCT    7440

CCTGCTTGGA AGAGACCTCA CACCGTCATC ACGATGCCAA CGGCTCTGAA GGTGGATGGC    7500

ATTCCTGCGT GGATTCATCA CTCCCGCATC AAAAAGGCCA ACGGAGCCCA ACTAGAAACA    7560
```

```
TGGGTCCCCA GGGCTGGGTC AGGCCCCTTA AAACTGCACC TAAGTTGGGT GAAGCCATTA        7620

GATTAATTCT TTTTCTTAAT TTTGTAAAAC AATGCATAGC TTCTGTCAAA CTTATGTATC        7680

TTAAGACTCA ATATAACCCC CTTGTTATAA CTGAGGAATC AATGATTTGA TTCCCCAAAA        7740

ACACAAGTGG GGAATGTAGT GTCCAACCTG GTTTTTACTA ACCCTGTTTT TAGACTCTCC        7800

CTTTCCTTTA ATCACTCAGC CTTGTTTCCA CCTGAATTGA CTCTCCCTTA GCTAAGAGCG        7860

CCAGATGGAC TCCATCTTGG CTCTTTCACT GGCAGCCGCT TCCTCAAGGA CTTAACTTGT        7920

GCAAGCTGAC TCCCAGCACA TCCAAGAATG CAATTAACTG ATAAGATACT GTGGCAAGCT        7980

ATATCCGCAG TTCCCAGGAA TTCGTCCAAT TGATTACACC CAAAAGCCCC GCGTCTATCA        8040

CCTTGTAATA ATCTTAAAGC CCCTGCACCT GGAACTATTA CGTTCCTGT AACCATTTAT         8100

CCTTTTAACT TTTTTGCCTA CTTTATTTCT GTAAAATTGT TTTAACTAGA CCCCCCCTCT        8160

CCTTTCTAAA CCAAAGTATA AAAGCAAATC TAGCCCCTTC TTCAGGCCGA GAGAATTTCG        8220

AGCGTTAGCC GTCTCTTGGC CACCAGCTAA ATAAACGGAT TCTTCATGTG TCTCAAAGTG        8280

TGGCGTTTTC TCTAACTCGC TCAGGTACGA CCGTGGTAGT ATTTTCCCCA ACGTCTTATT        8340

TTTAGGGCAC GTATGTAGAG TAACTTTTAT GAAAGAAACC AGTTAAGGAG GTTTTGGGAT        8400

TTCCTTTATC AACTGTAATA CTGGTTTTGA TTATTTATTT ATTTATTTAT TTTTTTTGAG        8460

AAGGAGTTTC ACTCTTGTTG CCCAGGCTGG AGTGCAATGG TGCGATCTTG GCTCACTGCA        8520

ACTTCCGCCT CCCAGGTTCA AGCGATTCTC CTGCCTCAGC CTCGAGAGTA GCTGGGATTA        8580

TAGGCATGCG CCACCACACC CAGCTAATTT TGTATTTTTA GTAAAGATGG GGTTTCTTCA        8640

TGTTGGTCAA GCTGGTCTGG AACTCCCCGC CTCGGGTGAT CTGCCCGCCT CGGCCTCCGA        8700

AAGTGCTGGG ATTACAGGTG TGATCCACCA CACCCAGCCG ATTTATATGT ATATAAATCA        8760

CATTCCTCTA ACCAAAATGT AGTGTTTCCT TCCATCTTGA ATATAGGCTG TAGACCCCGT        8820

GGGTATGGGA CATTGTTAAC AGTGAGACCA CAGCAGTTTT TATGTCATCT GACAGCATCT        8880

CCAAATAGCC TTCATGGTTG TCACTGCTTC CCAAGACAAT TCCAAATAAC ACTTCCCAGT        8940

GATGACTTGC TACTTGCTAT TGTTACTTAA TGTGTTAAGG TGGCTGTTAC AGACACTATT        9000

AGTATGTCAG GAATTACACC AAAATTTAGT GGCTCAAACA ATCATTTTAT TATGTATGTG        9060

GATTCTCATG GTCAGGTCAG GATTTCAGAC AGGGCACAAG GGTAGCCCAC TTGTCTCTGT        9120

CTATGATGTC TGGCCTCAGC ACAGGAGACT CAACAGCTGG GGTCTGGGAC CATTTGGAGG        9180

CTTGTTCCCT CACATCTGAT ACCTGGCTTG GGATGTTGGA AGAGGGGGTG AGCTGAGACT        9240

GAGTGCCTAT ATGTAGTGTT TCCATATGGC CTTGACTTCC TTACAGCCTG GCAGCCTCAG        9300

GGTAGTCAGA ATTCTTAGGA GGCACAGGGC TCCAGGGCAG ATGCTGAGGG GTCTTTTATG        9360

AGGTAGCACA GCAAATCCAC CCAGGATC                                          9388
```

(2) INFORMATION FOR SEQ ID NO: 142:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (xi) SEQUENCE DESCRIPTION: SEQ ID NO: 142:

```
TGTAAGTCGA GCAGTGTGAT GGAAGGAATG GTCTTTGGAG AGAGCATATC CATCTCCTCC          60

TCACTGCCTC CTAATGTCAT GAGGTACACT GAGCAGAATT AAACAGGGTA GTCTTAACCA         120

CACTATTTTT AGCTACCTTG TCAAGCTAAT GGTTAAAGAA CACTTTTGGT TTACACTTGT         180
```

```
TGGGTCATAG AAGTTGCTTT CCGCCATCAC GCAATAAGTT TGTGTGTAAT CAGAAGGAGT      240

TACCTTATGG TTTCAGTGTC ATTCTTTAGT TAACTTGGGA GCTGTGTAAT TTAGGCTTTG      300

CGTATTATTT CACTTCTGTT CTCCACTTAT GAAGTGATTG TGTGTTCGCG TGTGTGTGCG      360

TGCGCATGTG CTTCCGGCAG TTAACATAAG CAAATACCCA ACATCACACT GCTCGACTT       419

(2) INFORMATION FOR SEQ ID NO: 143:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 143:

TGTAAGTCGA GCAGTGTGAT GTCCACTGCA GTGTGTTGCT GGGAACAGTT AATGAGCAAA       60

TTGTATACAA TGGCTAGTAC ATTGACCGGG ATTTGTTGAA GCTGGTGAGT GTTATGACTT      120

AGCCTGTTAG ACTAGTCTAT GCACATGGCT CTGGTCAACT ACCGCTCTCT CATTTCTCCA      180

GATAAATCCC CCATGCTTTA TATTCTCTTC CAAACATACT ATCCTCATCA CCACATAGTT      240

CCTTTGTTAA TGCTTTGTTC TAGACTTTCC CTTTTCTGTT TTCTTATTCA AACCTATATC      300

TCTTTGCATA GATTGTAAAT TCAAATGCCC TCAGGGTGCA GGCAGTTCAT GTAAGGGAGG      360

GAGGCTAGCC AGTGAGATCT GCATCACACT GCTCGACTTA CA                        402

(2) INFORMATION FOR SEQ ID NO: 144:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (xi) SEQUENCE DESCRIPTION: SEQ ID NO: 144:

TCGGGTGATG CCTCCTCAGG CCAAGAAGAT AAAGCTTCAG ACCCCTAACA CATTTCCAAA       60

AAGGAAGAAA GGAGAAAAAA GGGCATCATC CCCGTTCCGA AGGGTCAGGG AGGAGGAAAT      120

TGAGGTGGAT TCACGAGTTG CGGACAACTC CTTTGATGCC AAGCGAGGTG CAGCCGGAGA      180

CTGGGGAGAG CGAGCCAATC AGGTTTTGAA GTTCCTCTCA GTGC                      224

(2) INFORMATION FOR SEQ ID NO: 145:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (xi) SEQUENCE DESCRIPTION: SEQ ID NO: 145:

AGCCATTTAC CACCCATCCA CAAAAAAAAA AAAAAAAAG AAAAATATCA AGGAATAAAA        60

ATAGACTTTG AACAAAAAGG AACATTTGCT GGCCTGAGGA GGCATCACCC G              111

(2) INFORMATION FOR SEQ ID NO: 146:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (xi) SEQUENCE DESCRIPTION: SEQ ID NO: 146:
```

-continued

| | |
|---|---|
| TAGCATGTTG AGCCCAGACA CTTGTAGAGA GAGGAGGACA GTTAGAAGAA GAAGAAAAGT | 60 |
| TTTTAAATGC TGAAAGTTAC TATAAGAAAG CTTTGGCTTT GGATGAGACT TTTAAAGATG | 120 |
| CAGAGGATGC TTTGCAGAAA CTTCATAAAT ATATGCAGGT GATTCCTTAT TTCCTCCTAG | 180 |
| AAATTTAGTG ATATTTGAAA TAATGCCCAA ACTTAATTTT CTCCTGAGGA AAACTATTCT | 240 |
| ACATTACTTA AGTAAGGCAT TATGAAAAGT TTCTTTTTAG GTATAGTTTT TCCTAATTGG | 300 |
| GTTTGACATT GCTTCATAGT GCCTCTGTTT TTGTCCATAA TCGAAAGTAA AGATAGCTGT | 360 |
| GAGAAAACTA TTACCTAAAT TTGGTATGTT GTTTTGAGAA ATGTCCTTAT AGGGAGCTCA | 420 |
| CCTGGTGGTT TTTAAATTAT TGTTGCTACT ATAATTGAGC TAATTATAAA AACCTTTTTG | 480 |
| AGACATATTT TAAATTGTCT TTTCCTGTAA TACTGATGAT GATGTTTTCT CATGCATTTT | 540 |
| CTTCTGAATT GGGACCATTG CTGCTGTGTC TGGGCTCACA TGCTA | 585 |

(2) INFORMATION FOR SEQ ID NO: 147:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (xi) SEQUENCE DESCRIPTION: SEQ ID NO: 147:

| | |
|---|---|
| TAGCATGTTG AGCCCAGACA CTGGGCAGCG GGGGTGGCCA CGGCAGCTCC TGCCGAGCCC | 60 |
| AAGCGTGTTT GTCTGTGAAG GACCCTGACG TCACCTGCCA GGCTAGGGAG GGGTCAATGT | 120 |
| GGAGTGAATG TTCACCGACT TTCGCAGGAG TGTGCAGAAG CCAGGTGCAA CTTGGTTTGC | 180 |
| TTGTGTTCAT CACCCCTCAA GATATGCACA CTGCTTTCCA AATAAAGCAT CAACTGTCAT | 240 |
| CTCCAGATGG GGAAGACTTT TTCTCCAACC AGCAGGCAGG TCCCCATCCA CTCAGACACC | 300 |
| AGCACGTCCA CCTTCTCGGG CAGCACCACG TCCTCCACCT TCTGCTGGTA CACGGTGATG | 360 |
| ATGTCAGCAA AGCCGTTCTG CANGACCAGC TGCCCCGTGT GCTGTGCCAT CTCACTGGCC | 420 |
| TCCACCGCGT ACACCGCTCT AGGCCGCGCA TANTGTGCAC AGAANAAATG ATGATCCAGT | 480 |
| CCCACAGCCC ACGTCCAAGA NGACTTTATC CGTCAGGGAT TCTTTATTCT GCAGGATGAC | 540 |
| CTGTGGTATT AATTGTTCGT GTCTGGGCTC AACATGCTA | 579 |

(2) INFORMATION FOR SEQ ID NO: 148:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (xi) SEQUENCE DESCRIPTION: SEQ ID NO: 148:

| | |
|---|---|
| TGACACCTTG TCCAGCATCT GCAAGCCAGG AAGAGAGTCC TCACCAAGAT CCCCACCCCG | 60 |
| TTGGCACCAG GATCTTGGAC TTCCAATCTC CAGAACTGTG AGAAATAAGT ATTTGTCGCT | 120 |
| AAATAAATCT TTGTGGTTTC AGATATTTAG CTATAGCAGA TCAGGCTGAC TAAGAGAAAC | 180 |
| CCCATAAGAG TTACATACTC ATTAATCTCC GTCTCTATCC CCAGGTCTCA GATGCTGGAC | 240 |
| AAGGTGTCA | 249 |

(2) INFORMATION FOR SEQ ID NO: 149:

(i) SEQUENCE CHARACTERISTICS:
        (A) LENGTH: 255 base pairs
        (B) TYPE: nucleic acid
        (C) STRANDEDNESS: single (D) TOPOLOGY: linear (xi) SEQUENCE DESCRIPTION: SEQ ID NO: 149:

TGACACCTTG TCCAGCATCT GCTATTTTGT GACTTTTTAA TAATAGCCAT TCTGACTGGT        60

GTGAGATGGT AACTCATTGT GGGTTTGGTC TGCATTTCTC TAATGATCAG TGATATTAAG       120

CTTTTTTTAA ATATGCTTGT TGACCACATG TATATCATCT TTTGAGAAGT GTCTGTTCAT       180

ATCCTTTGCC CACTTTTTAA TTTTTTTATC TTGTAAATTT GTTTAATTTC CTTACAGATG       240

CTGGACAAGG TGTCA                                                       255

(2) INFORMATION FOR SEQ ID NO: 150:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO: 150:

TTACGCTGCA ACACTGTGGA GGCCAAGCTG GGATCACTTC TTCATTCTAA CTGGAGAGGA        60

GGGAAGTTCA AGTCCAGCAG AGGGTGGGTG GGTAGACAGT GGCACTCAGA AATGTCAGCT       120

GGACCCCTGT CCCCGCATAG GCAGGACAGC AAGGCTGTGG CTCTCCAGGG CCAGCTGAAG       180

AACAGGACAC TGTCTCCGCT GCCACAAAGC GTCAGAGACT CCCATCTTTG AAGCACGGCC       240

TTCTTGGTCT TCCTGCACTT CCCTGTTCTG TTAGAGACCT GGTTATAGAC AAGGCTTCTC       300

CACAGTGTTG CAGCGTAA                                                    318

(2) INFORMATION FOR SEQ ID NO: 151:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (xi) SEQUENCE DESCRIPTION: SEQ ID NO: 151:

TNACGCNGCN ACNNTGTAGA GANGGNAAGG CNTTCCCCAC ATTNCCCCTT CATNANAGAA        60

TTATTCNACC AAGNNTGACC NATGCCNTTT ATGACTTACA TGCNNACTNC NTAATCTGTN       120

TCNNGCCTTA AAAGCNNNTC CACTACATGC NTCANCACTG TNTGTGTNAC NTCATNAACG       180

GTCNGNAATA GGGGCNCATA ACTACAGAAA TGCANTTCAT ACTGCTTCCA NTGCCATCNT       240

CGTGTGGCCT TNCCTACTCT TCTTNTATTC CAAGTAGCAT CTCTGGANTG CTTCCCCACG       300

CTCCACATTG TTGCAGCNAT AAT                                              323

(2) INFORMATION FOR SEQ ID NO: 152:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (xi) SEQUENCE DESCRIPTION: SEQ ID NO: 152:

TCAAGATTCC ATAGGCTGAC CAGTCCAAGG AGAGTTGAAA TCATGAAGGA GAGTCTATCT        60

GGAGAGAGCT GTAGTTTTGA GGGTTGCAAA GACTTAGGAT GGAGTTGGTG GGTGTGGTTA       120

GTCTCTAAGG TTGATTTTGT TCATAAATTT CATGCCCTGA ATGCCTTGCT TGCCTCACCC       180

TGGTCCAAGC CTTAGTGAAC ACCTAAAAGT CTCTGTCTTC TTGCTCTCCA AACTTCTCCT       240

| GAGGATTTCC TCAGATTGTC TACATTCAGA TCGAAGCCAG TTGGCAAACA AGATGCAGTC | 300 |
| CAGAGGGTCA G | 311 |

(2) INFORMATION FOR SEQ ID NO: 153:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO: 153:

| CAAGATTCCA TAGGCTGACC AGGAGGCTAT TCAAGATCTC TGGCAGTTGA GGAAGTCTCT | 60 |
| TTAAGAAAAT AGTTTAAACA ATTTGTTAAA ATTTTTCTGT CTTACTTCAT TTCTGTAGCA | 120 |
| GTTGATATCT GGCTGTCCTT TTTATAATGC AGAGTGGGAA CTTTCCCTAC CATGTTTGAT | 180 |
| AAATGTTGTC CAGGCTCCAT TGCCAATAAT GTGTTGTCCA AAATGCCTGT TTAGTTTTTA | 240 |
| AAGACGGAAC TCCACCCTTT GCTTGGTCTT AAGTATGTAT GGAATGTTAT GATAGGACAT | 300 |
| AGTAGTAGCG GTGGTCAGCC TATGGAATCT TG | 332 |

(2) INFORMATION FOR SEQ ID NO: 154:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 154:

| TCAAGATTCC ATAGGCTGAC CTGGACAGAG ATCTCCTGGG TCTGGCCCAG GACAGCAGGC | 60 |
| TCAAGCTCAG TGGAGAAGGT TTCCATGACC CTCAGATTCC CCCAAACCTT GGATTGGGTG | 120 |
| ACATTGCATC TCCTCAGAGA GGGAGGAGAT GTANGTCTGG GCTTCCACAG GGACCTGGTA | 180 |
| TTTTAGGATC AGGGTACCGC TGGCCTGAGG CTTGGATCAT TCANAGCCTG GGGGTGGAAT | 240 |
| GGCTGGCAGC CTGTGGCCCC ATTGAAATAG GCTCTGGGGC ACTCCCTCTG TTCCTANTTG | 300 |
| AACTTGGGTA AGGAACAGGA ATGTGGTCAN CCTATGGAAT CTTGA | 345 |

(2) INFORMATION FOR SEQ ID NO: 155:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (xi) SEQUENCE DESCRIPTION: SEQ ID NO: 155:

| GACGCTTGGC CACTTGACAC ATTAAACAGT TTTGCATAAT CACTANCATG TATTTCTAGT | 60 |
| TTGCTGTCTG CTGTGATGCC CTGCCCTGAT TCTCTGGCGT TAATGATGGC AAGCATAATC | 120 |
| AAACGCTGTT CTGTTAATTC CAAGTTATAA CTGGCATTGA TTAAAGCATT ATCTTTCACA | 180 |
| ACTAAACTGT TCTTCATANA ACAGCCCATA TTATATCAA ATTAAGAGAC AATGTATTCC | 240 |
| AATATCCTTT ANGGCCAATA TATTTNATGT CCCTTAATTA AGAGCTACTG TCCGT | 295 |

(2) INFORMATION FOR SEQ ID NO: 156:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO: 156:

```
GACGCTTGGC CACTTGACAC TGCAGTGGGA AAACCAGCAT GAGCCGCTGC CCCCAAGGAA      60

CCTCGAAGCC CAGGCAGAGG ACCAGCCATC CCAGCCTGCA GGTAAAGTGT GTCACCTGTC     120

AGGTGGGCTT GGGGTGAGTG GGTGGGGGAA GTGTGTGTGC AAAGGGGGTG TNAATGTNTA     180

TGCGTGTGAG CATGAGTGAT GGCTAGTGTG ACTGCATGTC AGGGAGTGTG AACAAGCGTG     240

CGGGGGTGTG TGTGCAAGTG CGTATGCATA TGAGAATATG TGTCTGTGGA TGAGTGCATT     300

TGAAAGTCTG TGTGTGTGCG TGTGGTCATG ANGGTAANTT ANTGACTGCG CAGGATGTGT     360

GAGTGTGCAT GGAACACTCA NTGTGTGTGT CAAGTGGCCN ANCGTC                    406
```

(2) INFORMATION FOR SEQ ID NO: 157:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (xi) SEQUENCE DESCRIPTION: SEQ ID NO: 157:

```
TGACGCTTGG CCACTTGACA CACTAAAGGG TGTTACTCAT CACTTTCTTC TCTCCTCGGT      60

GGCATGTGAG TGCATCTATT CACTTGGCAC TCATTTGTTT GGCAGTGACT GTAANCCANT     120

TCTGATGCAT ACACCAGCTT GTAAATTGAA TAAATGTCTC TAATACTATG TGCTCACAAA     180

ANGGTANGGG TGAGGAGAAG GGGAGAGA                                        208
```

(2) INFORMATION FOR SEQ ID NO: 158:

(i) SEQUENCE CHARACTERISTICS:
        (A) LENGTH: 547 base pairs
        (B) TYPE: nucleic acid
        (C) STRANDEDNESS: single
        (D) TOPOLOGY: linear (xi) SEQUENCE DESCRIPTION: SEQ ID NO: 158:

```
CTTCAACCTC CTTCAACCTC CTTCAACCTC CTGGATTCAA ACAATCATCC CACCTCAGAC      60

TCCTTAGTAG CTGAGACTAC AGACTCACGC CACTACATCT GGCTAAATTT TTGTAGAGAT     120

AGGGTTTCAT CATGTTGCCC TGGCTGGTCT CAAACTCCTG ACCTCAAGCA ATGTGCCCAC     180

CTCAGCCTCC CAAAGTGCTG GGATTACAGG CATAAGCCAC CATGCCCAGT CCATNTTTAA     240

TCTTTCCTAC CACATTCTTA CCACACTTTC TTTTATGTTT AGATACATAA ATGCTTACCA     300

TTATGATACA ATTGCCCACA GTATTAAGAC AGTAACATGC TGCACAGGTT TGTAGCCTAG     360

GAACAGTAGG CAATACCACA TAGCTTAGGT GTGTGGTAGA CTATACCATC TAGGTTTGTG     420

TAAGTTACAC TTTATGCTGT TTACACAATG ACAAAACCAT CTAATGATGC ATTTCTCAGA     480

ATGTATCCTT GTCAGTAAGC TATGATGTAC AGGGAACACT GCCCAAGGAC ACAGATATTG     540

TACCTGT                                                              547
```

(2) INFORMATION FOR SEQ ID NO: 159:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (xi) SEQUENCE DESCRIPTION: SEQ ID NO: 159:

```
GCTCCTCTTG CCTTACCAAC TCACCCAGTA TGTCAGCAAT TTTATCRGCT TTACCTACGA      60
```

```
AACAGCCTGT ATCCAAACAC TTAACACACT CACCTGAAAA GTTCAGGCAA CAATCGCCTT        120

CTCATGGGTC TCTCTGCTCC AGTTCTGAAC CTTTCTCTTT TCCTAGAACA TGCATTTARG        180

TCGATAGAAG TTCCTCTCAG TGC                                                203
```

(2) INFORMATION FOR SEQ ID NO: 160:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 160:

```
TGTAAGTCGA GCAGTGTGAT GGGTGGAACA GGGTTGTAAG CAGTAATTGC AAACTGTATT         60

TAAACAATAA TAATAATATT TAGCATTTAT AGAGCACTTT ATATCTTCAA AGTACTTGCA        120

AACATTAYCT AATTAAATAC CCTCTCTGAT TATAATCTGG ATACAAATGC ACTTAAACTC        180

AGGACAGGGT CATGAGARAA GTATGCATTT GAAAGTTGGT GCTAGCTATG CTTTAAAAAC        240

CTATACAATG ATGGGRAAGT TAGAGTTCAG ATTCTGTTGG ACTGTTTTTG TGCATTTCAG        300

TTCAGCCTGA TGGCAGAATT AGATCATATC TGCACTCGAT GACTYTGCTT GATAACTTAT        360

CACTGAAATC TGAGTGTTGA TCATCACACT GCTCGACTTA CA                          402
```

(2) INFORMATION FOR SEQ ID NO: 161:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO: 161:

```
AGCATGTTGA GCCCAGACAC TGACCAGGAG AAAAACCAAC CAATAGAAAC ACGCCCAGAC         60

ACTGACCAGG AGAAAAACCA ACCAATAAAA ACAGGCCCGG ACATAAGACA ATAATAAAA         120

TTAGCGGACA AGGACATGAA ACAGCTATT GTAAGAGCGG ATATAGTGGT GTGTGTCTGG        180

GCTCAACATG CTA                                                           193
```

(2) INFORMATION FOR SEQ ID NO: 162:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (xi) SEQUENCE DESCRIPTION: SEQ ID NO: 162:

```
TGTTGAGCCC AGACACTGAC CAGGAGAAAA ACCAACCAAT AAAAACAGGC CCGGACATAA         60

GACAAATAAT AAAATTAGCG GACAAGGACA TGAAACAGC TATTGTAAGA GCGGATATAG        120

TGGTGTGTGT CTGGGCTCAA CATGCTA                                            147
```

(2) INFORMATION FOR SEQ ID NO: 163:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO: 163:

```
TAGCATGTTG AGCCCAGACA CAAATCTTTC CTTAAGCAAT AAATCATTTC TGCATATGTT      60

TTTAAAACCA CAGCTAAGCC ATGATTATTC AAAAGGACTA TTGTATTGGG TATTTTGATT     120

TGGGTTCTTA TCTCCCTCAC ATTATCTTCA TTTCTATCAT TGACCTCTTA TCCCAGAGAC     180

TCTCAAACTT TTATGTTATA CAAATCACAT TCTGTCTCAA AAAATATCTC ACCCACTTCT     240

CTTCTGTTTC TGCGTGTGTA TGTGTGTGTG TGTGTGTCTG GGCTCAACAT GCTA           294
```

(2) INFORMATION FOR SEQ ID NO: 164:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (xi) SEQUENCE DESCRIPTION: SEQ ID NO: 164:

```
CGGGATTGGC TTTGAGCTGC AGATGCTGCC TGTGACCGCA CCCGGCGTGG AACAGAAAGC      60

CACCTGGCTG CAAGTGCGCC AGAGCCGCCC TGACTACGTG CTGCTGTGGG GCTGGGGCGT     120

GATGAACTCC ACCGCCCTGA AGGAAGCCCA GGCCACCGGA TACCCCCGCG ACAAGATGTA     180

CGGCGTGTGG TGGGCCGGTG CGGAGCCCGA TGTGCGTGAC GTGGGCGAAG GCGCCAAGGG     240

CTACAACGCG CTGGCTCTGA ACGGCTACGG CACGCAGTCC AAGGTGATCC ANGACATCCT     300

GAAACACGTG CACGACAAGG GCCAGGGCAC GGGGCCCAAA GACGAAGTGG GCTCGGTGCT     360

GTACACCCGC GGCGTGATCA TCCAGATGCT GGACAAGGTG TCAATCACTA AT             412
```

(2) INFORMATION FOR SEQ ID NO: 165:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (xi) SEQUENCE DESCRIPTION: SEQ ID NO: 165:

```
TTGACACCTT GTCCAGCATC TGCATCTGAT GAGAGCCTCA GATGGCTACC ACTAATGGCA      60

GAAGGCAAAG GAGAACAGGC ATTGTATGGC AAGAAAGGAA GAAAGAGAGA GGGGAGAAAG     120

GTGCTAGGTT CTTTTCAACA ACCAGTTCTT GATGGAACTG AGAGTAAGAG CTCAAGGCCA     180

GGTGTGGTGA CTCCAACCAG TAATCCCAAC ATTTTAGGAG GCTGAGGCAG GCAGATGTCT     240

TGACCCCATG AGTTTGTGAC CAGCCTGAAC AACATCATGA GACTCCATCT CTACAATAAT     300

TACAAAAATT AATCAGGCAT TGTGGTATGC CCTGTAGTCC CAGATGCTGG ACAAGGTGTC     360

A                                                                   361
```

(2) INFORMATION FOR SEQ ID NO: 166:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (xi) SEQUENCE DESCRIPTION: SEQ ID NO: 166:

```
TWGACTGACT CATGTCCCCT ACACCCAACT ATCTTCTCCA GGTGGCCAGG CATGATAGAA      60

TCTGATCCTG ACTTAGGGGA ATATTTTCTT TTTACTTCCC ATCTTGATTC CCTGCCGGTG     120

AGTTTCCTGG TTCAGGGTAA GAAAGGAGCT CAGGCCAAAG TAATGAACAA ATCCATCCTC     180

ACAGACGTAC AGAATAAGAG AACWTGGACW TAGCCAGCAG AACMCAAKTG AAAMCAGAAC     240
```

| | | | |
|---|---|---|---|
| MCTTAMCTAG | GATRACAAMC | MCRRARATAR | KTGCYCMCMC WTATAATAGA AACCAAACTT | 300 |
| GTATCTAATT | AAATATTTAT | CCACYGTCAG | GGCATTAGTG GTTTTGATAA ATACGCTTTG | 360 |
| GCTAGGATTC | CTGAGGTTAG | AATGGAARAA | CAATTGCAMC GAGGGTAGGG GACATGAGTC | 420 |
| AKTCTAA | | | 427 |

(2) INFORMATION FOR SEQ ID NO: 167:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO: 167:

| | | | | |
|---|---|---|---|---|
| AACGTCGCAT | GCTCCCGGCC | GCCATGGCCG | CGGGATAGAC TGACTCATGT CCCCTAAGAT | 60 |
| AGAGGAGACA | CCTGCTAGGT | GTAAGGAGAA | GATGGTTAGG TCTACGGAGG CTCCAGGGTG | 120 |
| GGAGTAGTTC | CCTGCTAAGG | GAGGGTAGAC | TGTTCAACCT GTTCCTGCTC CGGCCTCCAC | 180 |
| TATAGCAGAT | GCGAGCAGGA | GTAGGAGAGA | GGGAGGTAAG AGTCAGAAGC TTATGTTGTT | 240 |
| TATGCGGGGA | AACGCCRTAT | CGGGGGCAGC | CRAGTTATTA GGGGACANTR TAGWYARTCW | 300 |
| AGNTAGCATC | CAAAGCGNGG | GAGTTNTCCC | ATATGGTTGG ACCTGCAGGC GGCCGCATTA | 360 |
| GTGATTAGCA | TGTGAGCCCC | AGACACGCAT | AGCAACAAGG ACCTAAACTC AGATCCTGTG | 420 |
| CTGATTACTT | AACATGAATT | ATTGTATTTA | TTTAACAACT TTGAGTTATG AGGCATATTA | 480 |
| TTAGGTCCAT | ATTACCTGGA | | | 500 |

(2) INFORMATION FOR SEQ ID NO: 168:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (xi) SEQUENCE DESCRIPTION: SEQ ID NO: 168:

| | | | |
|---|---|---|---|
| TTCATCGCTC | GGTGACTCAA | GCCTGTAATC | CCAGAACTTT GGGAGGCCGA GGGGAGCAGA | 60 |
| TCACCTGAGG | TTGGGAGTTT | GAGACCAGCC | TGGCCAACAT GGTGACAACC CGTCTCTGCT | 120 |
| AAAAATACAA | AAATTAGCCA | AGCATGGTGG | CATGCACTTG TAATCCCAGC TACTCGGGAG | 180 |
| GCTGAGGCAG | GAGAATCACT | TGAGGCCAGG | AGGCAGAGGT TGCAGTGAGG CAGAGGTTGA | 240 |
| GATCATGCCA | CTGCACTCCA | GCCTGGGCAA | CAGAGTAAGA CTCCATCTCA AAAAAAAAAA | 300 |
| AAAAAAGAA | TGATCAGAGC | CACAAATACA | GAAAACCTTG AGTCACCGAG CGATGAAA | 358 |

(2) INFORMATION FOR SEQ ID NO: 169:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (xi) SEQUENCE DESCRIPTION: SEQ ID NO: 169:

| | | | |
|---|---|---|---|
| TTCTGTCCAC | ACCAATCTTA | GAGCTCTGAA | AGAATTTGTC TTTAAATATC TTTTAATAGT | 60 |
| AACATGTATT | TTATGGACCA | AATTGACATT | TTCGACTATT TTTTCCCAAA AAAAGTCAGG | 120 |
| TGAATTTCAG | CACACTGAGT | TGGGAATTTC | TTATCCCAGA AGWCGGCACG AGCAATTTCA | 180 |
| TATTTATTTA | AGATTGATTC | CATACTCCGT | TTTCAAGGAG AATCCCTGCA GTCTCCTTAA | 240 |

-continued

```
AGGTAGAACA AATACTTTCT ATTTTTTTTT CACCATTGTG GGATTGGACT TTAAGAGGTG        300

ACTCTAAAAA AACAGAGAAC AAATATGTCT CAGTTGTATT AAGCACGGAC CCATATTATC        360

ATATTCACTT AAAAAAATGA TTTCCTGTGC ACCTTTTGGC AACTTCTCTT TTCAATGTAG        420

GGAAAAACTT AGTCACCCTG AAAACCCACA AAATAAATAA AACTTGTAGA TGTGGGCAGA        480

ARGTTTGGGG GTGGACATTG TATGTGTTTA AATTAAACCC TGTATCACTG AGAAGCTGTT        540

GTATGGGTCA GAGAAAATGA ATGCTTAGAA GCTGTTCACA TCTTCAAGAG CAGAAGCAAA        600

CCACATGTCT CAGCTATATT ATTATTTATT TTTTATGCAT AAAGTGAATC ATTTCTTCTG        660

TATTAATTTC CAAAGGGTTT TACCCTCTAT TTAAATGCTT TGAAAAACAG TGCATTGACA        720

ATGGGTTGAT ATTTTTCTTT AAAAGAAAAA TATAATTATG AAAGCCAAGA TAATCTGAAG        780

CCTGTTTTAT TTTAAAACTT TTTATGTTCT GTGGTTGATG TTGTTTGTTT GTTTGTTTCT        840

ATTTTGTTGG TTTTTTACTT TGTTTTTTGT TTTGTTTTGT TTTGGTTTDG CATACTACAT        900

GCAGTTTCTT TAACCAATGT CTGTTTGGCT AATGTAATTA AAGTTGTTAA TTTATATGAG        960

TGCATTTCAA CTATGTCAAT GGTTTCTTAA TATTTATTGT GTAGAAGTAC TGGTAATTTT       1020

TTTATTTACA ATATGTTTAA AGAGATAACA GTTTGATATG TTTTCATGTG TTTATAGCAG       1080

AAGTTATTTA TTTCTATGGC ATTCCAGCGG ATATTTTGGT GTTTGCGAGG CATGCAGTCA       1140

ATATTTTGTA CAGTTAGTGG ACAGTATTCA GCAACGCCTG ATAGCTTCTT TGGCCTTATG       1200

TTAAATAAAA AGACCTGTTT GGGATGTAAA AAAAAAAAAA AAAAAAAAAA AAAAAAAAAA       1260

AAAAA                                                                  1265

(2) INFORMATION FOR SEQ ID NO: 170:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO: 170:

TGTAAGTCGA GCAGTGTGAT GACGATATTC TTCTTATTAA TGTGGTAATT GAACAAATGA         60

TCTGTGATAC TGATCCTGAG CTAGGAGGCG CTGTTCAGTT AATGGGACTT CTTCGTACTC        120

TAATTGATCC AGAGAACATG CTGGCTACAA CTAATAAAAC CGAAAAAGT GAATTTCTAA         180

ATTTTTTCTA CAACCATTGT ATGCATGTTC TCACAGCACC ACTTTTGACC AATACTTCAG        240

AAGACAAATG TGAAAAGGAT AATATAGTTG GATCAAACAA AAACAACACA ATTTGTCCCG        300

ATAATTATCA AACAGCACAG CTACTTGCCT TAATTTTAGA GTTACTCACA TTTTGTGTGG        360

AACATCACAC TGCTCGACTT ACA                                               383

(2) INFORMATION FOR SEQ ID NO: 171:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO: 171:

TGGGCACCTT CAATATCGCA AGTTAAAAAT AATGTTGAGT TTATTATACT TTTGACCTGT         60

TTAGCTCAAC AGGGTGAAGG CATGTAAAGA ATGTGGACTT CTGAGGAATT TTCTTTTAAA       120

AAGAACATAA TGAAGTAACA TTTTAATTAC TCAAGGACTA CTTTTGGTTG AAGTTTATAA        180

TCTAGATACC TCTACTTTTT GTTTTGCTG TTCGACAGTT CACAAAGACC TTCAGCAATT        240
```

```
TACAGGGTAA AATCGTTGAA GTAGTGGAGG TGAAACTGAA ATTTAAAATT ATTCTGTAAA      300

TACTATAGGG AAAGAGGCTG AGCTTAGAAT CTTTTGGTTG TTCATGTGTT CTGTGCTCTT      360

ATCATCACAC TGCTCGACTT ACA                                             383
```

(2) INFORMATION FOR SEQ ID NO: 172:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (xi) SEQUENCE DESCRIPTION: SEQ ID NO: 172:

```
TCGGGTGATG CCTCCTCAGG CTTGTCGTTA GTGTACACAG AGCTGCTCAT GAAGCGACAG       60

CGGCTGCCCC TGGCACTTCA GAACCTCTTC CTCTACACTT TTGGTGCGCT TCTGAATCTA      120

GGTCTGCATG CTGGCGGCGG CTCTGGCCCA GGCCTCCTGG AAAGTTTCTC AGGATGGGCA      180

GCACTCGTGG TGCTGAGCCA GGCACTAAAT GGACTGCTCA TGTCTGCTGT CATGGAGCAT      240

GGCAGCAGCA TCACACGCCT CTTTGTGGTG TCCTGCTCGC TGGTGGTCAA CGCCGTGCTC      300

TCAGCAGTCC TGCTACGGCT GCAGCTCACA GCCGCCTTCT TCCTGGCCAC ATTGCTCATT      360

GGCCTGGCCA TGCGCCTGTA CTATGGCAGC CGCTAGTCCC TGACAACTTC CACCCTGATT      420

CCGGACCCTG TAGATTGGGC GCCACCACCA GATCCCCCTC CCAGGCCTTC CTCCCTCTCC      480

CATCAGCGGC CCTGTAACAA GTGCCTTGTG AGAAAAGCTG GAGAAGTGAG GGCAGCCAGG      540

TTATTCTCTG GAGGTTGGTG GATGAAGGGG TACCCCTAGG AGATGTGAAG TGTGGGTTTG      600

GTTAAGGAAA TGCTTACCAT CCCCCACCCC CAACCAAGTT NTTCCAGACT AAAGAATTAA      660

GGTAACATCA ATACCTAGGC CTGAGGAGGC ATCACCCGA                             699
```

(2) INFORMATION FOR SEQ ID NO: 173:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (xi) SEQUENCE DESCRIPTION: SEQ ID NO: 173:

```
TCGGGTGATG CCTCCTCAGG CCAGATCAAA CTTGGGGTTG AAAACTGTGC AAAGAAATCA       60

ATGTCGGAGA AAGAATTTTG CAAAAGAAAA ATGCCTAATC AGTACTAATT TAATAGGTCA      120

CATTAGCAGT GGAAGAAGAA ATGTTGATAT TTTATGTCAG CTATTTTATA ATCACCAGAG      180

TGCTTAGCTT CATGTAAGCC ATCTCGTATT CATTAGAAAT AAGAACAATT TTATTCGTCG      240

GAAAGAACTT TTCAATTTAT AGCATCTTAA TTGCTCAGGA TTTTAAATTT TGATAAAGAA      300

AGCTCCACTT TTGGCAGGAG TAGGGGGCAG GGAGAGAGGA GGCTCCATCC ACAAGGACAG      360

AGACACCAGG GCCAGTAGGG TAGCTGGTGG CTGGATCAGT CACAACGGAC TGACTTATGC      420

CATGAGAAGA AACAACCTCC AAATCTCAGT TGCTTAATAC AACACAAGCT CATTTCTTGC      480

TCACGTTACA TGTCCTATGT AGATCAACAG CAGGTGACTC AGGGACCCAG GCTCCATCTC      540

CATATGAGCT TCCATAGTCA CCAGGACACG GGCTCTGAAA GTGTCCTCCA TGCAGGGACA      600

CATGCCTCTT CCTTTCATTG GGCAGAGCAA GTCACTTATG GCCAGAAGTC ACACTGCAGG      660

GCAGTGCCAT CCTGCTGTAT GCCTGAGGAG GCATCACCCG A                         701
```

(2) INFORMATION FOR SEQ ID NO: 174:

(i) SEQUENCE CHARACTERISTICS:
    (A) LENGTH: 700 base pairs
    (B) TYPE: nucleic acid
    (C) STRANDEDNESS: single
    (D) TOPOLOGY: linear (xi) SEQUENCE DESCRIPTION: SEQ ID NO: 174:

```
TCGGGTGATG CCTCCTCANG CCCCTAAATC AGAGTCCAGG GTCAGAGCCA CAGGAGACAG     60
GGAAAGACAT AGATTTTAAC CGGCCCCCTT CAGGAGATTC TGAGGCTCAG TTCACTTTGT    120
TGCAGTTTGA ACAGAGGCAG CAAGGCTAGT GGTTAGGGGC ACGGTCTCTA AAGCTGCACT    180
GCCTGGATCT GCCTCCCAGC TCTGCCAGGA ACCAGCTGCG TGGCCTTGAG CTGCTGACAC    240
GCAGAAAGCC CCCTGTGGAC CCAGTCTCCT CGTCTGTAAG ATGAGGACAG GACTCTAGGA    300
ACCCTTTCCC TTGGTTTGGC CTCACTTTCA CAGGCTCCCA TCTTGAACTC TATCTACTCT    360
TTTCCTGAAA CCTTGTAAAA GAAAAAAGTG CTAGCCTGGG CAACATGGCA AAACCCTGTC    420
TCTACAAAAA ATACAAAAAT TAGTTGGGTG TGGTGGCATG TGCCTGTAGT CCCAGCCACT    480
TGGGAGGTGC TGAGGTGGGA GGATCACTTG AGCCCGGGAG GTGGAGGTTG CAGTGAGCCA    540
AGATCATGCC ACTGCACTCC AGCCTGAGTA ATAGAGTAAG ACTCTGTCTC AAAAACAACA    600
ACAACAACAG TGAGTGTGCC TCTGTTTCCG GGTTGGATGG GGCACCACAT TTATGCATCT    660
CTCAGATTTG GACGCTGCAG CCTGAGGAGG CATCACCCGA                          700
```

(2) INFORMATION FOR SEQ ID NO: 175:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (xi) SEQUENCE DESCRIPTION: SEQ ID NO: 175:

```
TATAGGGCGA ATTGGGCCCG AGTTGCATGN TCCCGGCCGC CATGGCCGCG GGATTCGGGT     60
GATGCCTCCT CAGGCTTGTC TGCCACAAGC TACTTCTCTG AGCTCAGAAA GTGCCCCTTG    120
ATGAGGGAAA ATGTCCTACT GCACTGCGAA TTTCTCAGTT CCATTTTACC TCCCAGTCCT    180
CCTTCTAAAC CAGTTAATAA ATTCATTCCA CAAGTATTTA CTGATTACCT GCTTGTGCCA    240
GGGACTATTC TCAGGCTGAA GAAGGTGGGA GGGGAGGGCG GAACCTGAGG AGCCACCTGA    300
GCCAGCTTTA TATTTCAACC ATGGCTGGCC CATCTGAGAG CATCTCCCCA CTCTCGCCAA    360
CCTATCGGGG CATAGCCCAG GGATGCCCCC AGGCGGCCCA GGTTAGATGC GTCCCTTTGG    420
CTTGTCAGTG ATGACATACA CCTTAGCTGC TTAGCTGGTG CTGGCCTGAG GAGGCATCAC    480
CCGA                                                                 484
```

(2) INFORMATION FOR SEQ ID NO: 176:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO: 176:

```
TCGGGTGATG CCTCCTCAGG GCTCAAGGGA TGAGAAGTGA CTTCTTTCTG GAGGGACCGT     60
TCATGCCACC CAGGATGAAA ATGGATAGGG ACCCACTTGG AGGACTTGCT GATATGTTTG    120
GACAAATGCC AGGTAGCGGA ATTGGTACTG GTCCAGGAGT TATCCAGGAT AGATTTTCAC    180
```

```
CCACCATGGG ACGTCATCGT TCAAATCAAC TCTTCAATGG CCATGGGGGA CACATCATGC    240

CTCCCACACA ATCGCAGTTT GGAGAGATGG GAGGCAAGTT TATGAAAAGC CAGGGGCTAA    300

GCCAGCTCTA CCATAACCAG AGTCAGGGAC TCTTATCCCA GCTGCAAGGA CAGTCGAAGG    360

ATATGCCACC TCGGTTTTCT AAGAAAGGAC AGCTTAATGC AGATGAGATT AGCCTGAGGA    420

GGCATCACCC GA                                                       432

(2) INFORMATION FOR SEQ ID NO: 177:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (xi) SEQUENCE DESCRIPTION: SEQ ID NO: 177:

TAGCATGTTG AGCCCAGACA CAGTAGCATT TGTGCCAATT TCTGGTTGGA ATGGTGACAA     60

CATGCTGGAG CCAAGTGCTA ACATGCCTTG GTTCAAGGGA TGGAAAGTCA CCCGTAAGGA    120

TGGCAATGCC AGTGGAACCA CGCTGCTTGA GGCTCTGGAC TGCATCCTAC CACCAACTCG    180

CCCAACTGAC AAGCCCTTGC GCCTGCCTCT CCAGGATGTC TACAAAATTG GTGGTATTGG    240

TACTGTTCCT GTTGGCCGAG TGGAGACTGG TGTTCTCAAA CCCGGTATGG TGGTCACCTT    300

TGCTCCAGTC AACGTTACAA CGGAAGTAAA ATCTGTCGAA ATGCACCATG AAGCTTTGAG    360

TGAAGCTCTT CCTGGGGACA ATGTGGGCTT CAATGTCAAG AATGTGTCTG TCAAGGATGT    420

TCGTCGTGGC AACGTTGCTG GTGACAGCAA AAATGACCCA CCAATGGAAG CAGCTGGCTT    480

CACTGCTCAG GTGATTATCC TGAACCATCC AGGCCAAATA AGTGCCGGCT ATGCCCCTGT    540

ATTGGATTGC CACACGGCTC ACATTGCATG CAAGTTTGCT GAGCTGAAGG AAAAGATTGA    600

TCGCCGTTCT GGTAAAAAGC TGGAAGATGG CCCTAAATTC TTGAAGTCTG GTGATGCTGC    660

CATTGTTGAT ATGGTTCCTG GCAAGCCCAT GTGTGTTGAG AGCTTCTCAG ACTATCCACC    720

TTTGGGTCGC TTTGCTGTTC GTGATATGAG ACAGACAGTT GCGGTGGGTG TCTGGGCTCA    780

ACATGCTA                                                            788

(2) INFORMATION FOR SEQ ID NO: 178:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO: 178:

TAGCATGTTG AGCCCAGACA CCTGTGTTTC TGGGAGCTCT GGCAGTGGCG GATTCATAGG     60

CACTTGGGCT GCACTTTGAA TGACACACTT GGCTTTATTA GATTCACTAG TTTTTAAAAA    120

ATTGTTGTTC GTTTCTTTTC ATTAAAGGTT TAATCAGACA GATCAGACAG CATAATTTTG    180

TATTTAATGA CAGAAACGTT GGTACATTTC TTCATGAATG AGCTTGCATT CTGAAGCAAG    240

AGCCTACAAA AGGCACTTGT TATAAATGAA AGTTCTGGCT CTAGAGGCCA GTACTCTGGA    300

GTTTCAGAGC AGCCAGTGAT TGTTCCAGTC AGTGATGCCT AGTTATATAG AGGAGGAGTA    360

CACTGTGCAC TCTTCTAGGT GTAAGGGTAT GCAACTTTGG ATCTTAAAAT TCTGTACACA    420

TACACACTTT ATATATATGT ATGTATGTAT GAAAACATGA AATTAGTTTG TCAAATATGT    480

GTGTGTTTAG TATTTTAGCT TAGTGCAACT ATTTCCACAT TATTTATTAA ATTGATCTAA    540

GACACTTTCT TGTTGACACC TTGAATATTA ATGTTCAAGG GTGCAATGTG TATTCCTTTA    600
```

```
GATTGTTAAA GCTTAATTAC TATGATTTGT AGTAAATTAA CTTTTAAAAT GTATTTGAGC        660

CCTTCTGTAG TGTCGTAGGG CTCTTACAGG GTGGGAAAGA TTTTAATTTT CCAGTTGCTA        720

ATTGAACAGT ATGGCCTCAT TATATATTTT GATTTATAGG AGTTTGTGTC TGGGCTCAAC        780

ATGCTA                                                                   786
```

(2) INFORMATION FOR SEQ ID NO: 179:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (xi) SEQUENCE DESCRIPTION: SEQ ID NO: 179:

```
TAGCATGTTG AGCCCAGACA CTGGTTACAA GACCAGACCT GCTTCCTCCA TATGTAAACA         60

GCTTTTAAAA AGCCAGTGAA CCTTTTTAAT ACTTTGGCAA CCTTCTTTCA CAGGCAAAGA        120

ACACCCCCAT CCGCCCCTTG TTTGGAGTGC AGAGTTTGGC TTTGGTTCTT TGCCTTGCCT        180

GGAGTATACT TCTAATTCCT GTTGTCCTGC ACAAGCTGAA TACCGAGCTA CCCACCGCCA        240

CCCAGGCCAG GTTTCCACTC ATTTATTACT TTATGTTTCT GTTCCATTGC TGGTCCACAG        300

AAATAAGTTT TCCTTTGGAG GAATGTGATT ATACCCCTTT AATTTCCTCC TTTTGCTTTT        360

TTTTAATATC ATTGGTATGT GTTTGGCCCA GAGGAAACTG AAATTCACCA TCATCTTGAC        420

TGGCAATCCC ATTACCATGC TTTTTTTAAA AAACGTAATT TTTCTTGCCT TACATTGGCA        480

GAGTAGCCCT TCCTGGCTAC TGGCTTAATG TAGTCACTCA GTTTCTAGGT GGCATTAGGC        540

ATGAGACCTG AAGCACAGAC TGTCTTACCA CAAAAGGTGA CAAGATCTCA AACCTTAGCC        600

AAAGGGCTAT GTCAGGTTTC AATGCTATCT GCTTCTGTTC CTGCTCACTG TTCTGGATTT        660

TGTCCTTCTT CATCCCTAGC ACCAGAATTT CCCAGTCTCC CTCCCTACCT TCCCTTGTTT        720

TAATTCTAAT CTATCAGCAA AATAACTTTT CAAATGTTTT AACCGGTATC TCCATGTGTC        780

TGGGCTCAAC ATGCTA                                                        796
```

(2) INFORMATION FOR SEQ ID NO: 180:

(i) SEQUENCE CHARACTERISTICS:
        (A) LENGTH: 488 base pairs
        (B) TYPE: nucleic acid
        (C) STRANDEDNESS: single
        (D) TOPOLOGY: linear (xi) SEQUENCE DESCRIPTION: SEQ ID NO: 180:

```
GGATGTGCTG CAAGGCGATT AAGTTGGGTA ACGCCAGGGT TTTCCCAGTC ACGACGTTGT         60

AAAACGACGG CCAGTGAATT GTAATACGAC TCACTATAGG GCGAATTGGG CCCGACGTCG        120

CATGCTCCCG GCCGCCATGG CCGCGGGATA GCATGTTGAG CCCAGACACC TGCAGGTCAT        180

TTGGAGAGAT TTTTCACGTT ACCAGCTTGA TGGTCTTTTT CAGGAGGAGA GACACTGAGC        240

ACTCCCAAGG TGAGGTTGAA GATTTCCTCT AGATAGCCGG ATAAGAAGAC TAGGAGGGAT        300

GCCTAGAAAA TGATTAGCAT GCAAATTTCT ACCTGCCATT TCAGAACTGT GTGTCAGCCC        360

ACATTCAGCT GCTTCTTGTG AACTGAAAAG AGAGAGGTAT TGAGACTTTT CTGATGGCCG        420

CTCTAACATT GTAACACAGT AATCTGTGTG TGTGTGGGTG TGTGTGTGTG TCTGGGCTCA        480

ACATGCTA                                                                 488
```

(2) INFORMATION FOR SEQ ID NO: 181:

(i) SEQUENCE CHARACTERISTICS:
    (A) LENGTH: 317 base pairs
    (B) TYPE: nucleic acid
    (C) STRANDEDNESS: single
    (D) TOPOLOGY: linear (xi) SEQUENCE DESCRIPTION: SEQ ID NO: 181:

```
TAGCATGTTG AGCCCAGACA CGGCGACGGT ACCTGATGAG TGGGGTGATG GCACCTGTGA      60
AAAGGAGGAA CGTCATCCCC CATGATATTG GGGACCCAGA TGATGAACCA TGGCTCCGCG     120
TCAATGCATA TTTAATCCAT GATACTGCTG ATTGGAAGGA CCTGAACCTG AAGTTTGTGC     180
TGCAGGTTTA TCGGGACTAT TACCTCACGG GTGATCAAAA CTTCCTGAAG GACATGTGGC     240
CTGTGTGTCT AGTAAGGGAT GCACATGCAG TGGCCAGTGT GCCAGGGGTA TGGTTGGTGT     300
CTGGGCTCAA CATGCTA                                                    317
```

(2) INFORMATION FOR SEQ ID NO: 182:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO: 182:

```
TAGCATGTTG AGCCCAGACA CTGGCTGTTA GCCAAATCCT CTCTCAGCTG CTCCCTGTGG      60
TTTGGTGACT CAGGATTACA GAGGCATCCT GTTTCAGGGA ACAAAAAGAT TTTAGCTGCC     120
AGCAGAGAGC ACCACATACA TTAGAATGGT AAGGACTGCC ACCTCCTTCA AGAACAGGAG     180
TGAGGGTGGT GGTGAATGGG AATGGAAGCC TGCATTCCCT GATGCATTTG TGCTCTCTCA     240
AATCCTGTCT TAGTCTTAGG AAAGGAAGTA AAGTTTCAAG GACGGTTCCG AACTGCTTTT     300
TGTGTCTGGG CTCAACATGC TATCCCGCGG CCATGGCGGC CGGAGCATG CGACGTCGGG      360
CCCAATTCGC CCTATAGTGA GTCGTATTAC AATTCACTGG CCGTCGTTTT ACAACGTCGT     420
GACTGGGAAA ACCCTGGCGT TACCCAACTT AATCGCCTTG CAGCACATCC CCCTTTCCCA     480
GCTGGCGTAA TANCGAAAAG GCCCGCA                                         507
```

(2) INFORMATION FOR SEQ ID NO: 183:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (xi) SEQUENCE DESCRIPTION: SEQ ID NO: 183:

```
GATTTACGCT GCAACACTGT GGAGGTAGCC CTGGAGCAAG GCAGGCATGG ATGCTTCTGC      60
AATCCCCAAA TGGAGCCTGG TATTTCAGCC AGGAATCTGA GCAGAGCCCC CTCTAATTGT     120
AGCAATGATA AGTTATTCTC TTTGTTCTTC AACCTTCCAA TAGCCTTGAG CTTCCAGGGG     180
AGTGTCGTTA ATCATTACAG CCTGGTCTCC ACAGTGTTGC AGCGTAA                   227
```

(2) INFORMATION FOR SEQ ID NO: 184:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO: 184:

```
TTACGCTGCA ACACTGTGGA GCAGATTAAC ATCAGACTTT TCTATCAACA TGACTGGGGT      60

TACTAAAAAG ACAACAAATC AATGGCTTCA AAAGTCTAAG GAATAATTTC GATACTTCAA     120

CTTTATAAAA CCTGACAAAA CTATCAATCA AGCATAAAGA CAGATGAAGA ACATTTCCAG     180

ATTTTGGCCA ATCAGATATT TTACCTCCAC AGTGTTGCAG CGTAA                    225

(2) INFORMATION FOR SEQ ID NO: 185:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO: 185:

GGCCCGACGT CGCATGCTCC CGGCCGCCAT GGCCGCGGGA TTCGTTAGGG TCTCTATCCA      60

CTGGGACCCA TAGGCTAGTC AGAGTATTTA GAGTTGAGTT CCTTTCTGCT TCCCAGAATT     120

TGAAAGAAAA GGAGTGAGGT GATAGAGCTG AGAGATCAGA TTTGCCTCTG AAGCCTGTTC     180

AAGATGTATG TGCTCAGACC CCACCACTGG GGCCTGTGGG TGAGGTCCTG GCATCTATT     240

TGAATGAATT GCTGAAGGGG AGCACTATGC CAAGGAAGGG GAACCCATCC TGGCACTGGC     300

ACAGGGGTCA CCTTATCCAG TGCTCAGTGC TTCTTTGCTG CTACCTGGTT TTCTCTCATA     360

TGTGAGGGGC AGGTAAGAAG AAGTGCCCRG TGTTGTGCGA GTTTTAGAAC ATCTACCAGT     420

AAGTGGGGAA GTTTCACAAA GCAGCAGCTT TGTTTTGTGT ATTTTCACCT TCAGTTAGAA     480

GAGGAAGGCT GTGAGATGAA TGTTAGTTGA GTGGAAAAGA CGGGTAAGCT TAGTGGATAG     540

AGACCCTAAC GAATCACTAG TGCGGCCGCC TTGCAGGTCG ACCATATGGG AGAGCTC       597

(2) INFORMATION FOR SEQ ID NO: 186:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (xi) SEQUENCE DESCRIPTION: SEQ ID NO: 186:

GGCCCGAAGT TGCATGTTCC CGGCCGCCAT GGCCGCGGGA TTCGTTAGGG TCTCTATCCA      60

CTACCTAAAA AATCCCAAAC ATATAACTGA ACTCCTCACA CCCAATTGGA CCAATCCATC     120

ACCCCAGAGG CCTACAGATC CTCCTTTGAT ACATAAGAAA ATTTCCCCAA ACTACCTAAC     180

TATATCATTT TGCAAGATTT GTTTTACCAA ATTTTGATGG CCTTTCTGAG CTTGTCAGTG     240

TGAACCACTA TTACGAACGA TCGGATATTA ACTGCCCCTC ACCGTCCAGG TGTAGCTGGC     300

AACATCAAGT GCAGTAAATA TTCATTAAGT TTTCACCTAC TAAGGTGCTT AAACACCCTA     360

GGGTGCCATG TCGGTAGCAG ATCTTTTGAT TTGTTTTTAT TTCCCATAAG GGTCCTGTTC     420

AAGGTCAATC ATACATGTAG TGTGAGCAGC TAGTCACTAT CGCATGACTT GGAGGGTGAT     480

AATAGAGGCC TCCTTTGCTG TTAAAGAACT CTTGTCCCAG CCTGTCAAAG TGGATAGAGA     540

CCCTAACGAA TCACTAGTGC GGCCGCCTGC AGGTCGACCA TATGGGAGAG CTCCCAA       597

(2) INFORMATION FOR SEQ ID NO: 187:

(i) SEQUENCE CHARACTERISTICS:
        (A) LENGTH: 324 base pairs
        (B) TYPE: nucleic acid
        (C) STRANDEDNESS: single
        (D) TOPOLOGY: linear
```

(xi) SEQUENCE DESCRIPTION: SEQ ID NO: 187:

TCGTTAGGGT CTCTATCCAC TTGCAGGTAA AATCCAATCC TGTGTATATC TTATAGTCTT    60

CCATATGTAG TGGTTCAAGA GACTGCAGTT CCAGAAAGAC TAGCCGAGCC CATCCATGTC   120

TTCCACTTAA CCCTGCTTTG GGTTACACAT CTTAACTTTT CTGTTCAAGT TTCTCTGTGT   180

AGTTTATAGC ATGAGTATTG GGAWAATGCC CTGAAACCTG ACATGAGATC TGGGAAACAC   240

AAACTTACTC AATAAGAATT TCTCCCATAT TTTTATGATG GAAAAATTTC ACATGCACAG   300

AGGAGTGGAT AGAGACCCTA ACGA                                         324

(2) INFORMATION FOR SEQ ID NO: 188:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO: 188:

GCGCGGGGAT TCGGGGTGAT ACCTCCTCAT GCCAAAATAC AACGTNTAAT TTCACAACTT    60

GCCTTCCAAT TTACGCATTT TCAATTTGCT CTCCCCATTT GTTGAGTCAC AACAAACACC   120

ATTGCCCAGA AACATGTATT ACCTAACATG CACATACTCT TAAAACTACT CATCCCTT    178

(2) INFORMATION FOR SEQ ID NO: 189:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (xi) SEQUENCE DESCRIPTION: SEQ ID NO: 189:

TGACACCTTG TCCAGCATCT GACACAGTCT TGGCTCTTGG AAAATATTGG ATAAATGAAA    60

ATGAATTTCT TTAGCAAGTG GTATAAGCTG AGAATATACG TATCACATAT CCTCATTCTA   120

AGACACATTC AGTGTCCCTG AAATTAGAAT AGGACTTACA ATAAGTGTGT TCACTTTCTC   180

AATAGCTGTT ATTCAATTGA TGGTAGGCCT TAAAAGTCAA AGAAATGAGA GGGCATGTGA   240

AAAAAAGCTC AACATCACTG ATCATTAGAA AACTTCCATT CAAACCCCCA ATGAGATACC   300

ATCTCATACC AGTCAGAATG CTATTATTA AAAAGTCAAA AATAACAGA TGCTGGACAA    360

GGTGTCA                                                            367

(2) INFORMATION FOR SEQ ID NO: 190:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO: 190:

GACACCTTGT CCAGCATCTG ACAACGCTAA CAGCCTGAGG AGATCTTTAT TTATTTATTT    60

AGTTTTTACT CTGGCTAGGC AGATGGTGGC TAAAACATTC ATTTACCCAT TTATTCATTT   120

AATTGTTCCT GCAAGGCCTA TGGATAGAGT ATTGTCCAGC ACTGCTCTGG AAGCTAGGAG   180

CATGGGGATG AACAAGATAG GCTACATCCT GTTCCCACAG AACTTCCACT TTAGTCTGGG   240

AAACAGATGA TATATACAAA TATATAAATG AATTCAGGTA GTTTTAAGTA CGAAAAGAAT   300

AAGAAAGCAG AGTCATGATT TANAATGCTG GAAACAGGGG CTATTGCTTG AGATATTGAA   360

```
GGTGCCCAA                                                            369

(2) INFORMATION FOR SEQ ID NO: 191:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (xi) SEQUENCE DESCRIPTION: SEQ ID NO: 191:

TGACACCTTG TCCAGCATCT GCACAGGGAA AAGAAACTAT TATCAGAGTG AACAGGCAAC     60

CTACAGAATG GGAGAAAATT TTTGCAATCT ATCCATCTGA CAAAGGGCTA ATATCCAGAA    120

TCTACAAAGA ACTTATACAA ATTTACAAGA AACAAACAAA CAAACAACTC CTCAAAAAGT    180

GGGTGAAGGA TGTGAACAGA CACTTCTCAA AAGAAGACAT TTATGGGCC AACAAACATA     240

TGAAAAAAAG CTCATCATCA CTGGTCACTA GATAAATGCA AATCAAAACC ACAATGAGAT    300

ACCATCTCAT TCCAGTTAGA ATGGCAATCA TTAAAAAGTC AGGAAACAAC AGATGCTGGA    360

CAAGGTGTC                                                            369

(2) INFORMATION FOR SEQ ID NO: 192:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO: 192:

TGACGCTTGG CCACTTGACA CTTCATCTTT GCACAGAAAA ACTTCTTTAC AGATTTAATT     60

CAAGACTGGT CTAGTGACAG TCCTCCAGAC ATTTTTTCAT TTGTTCCATA TACGTGGAAT    120

TTTAAAATCA TGTTTCATCA GTTTGAAATG ATTTGGGCTG CTAATCAACA CAATTGGATC    180

GACTGTTCTA CTAAACAACA GGAAAATGTG TATCTGGCAG CCTGTGGAGA ACACTAAAC    240

ATTGATTTTT CTTTGCCTTT TACGGACTTT GTTCCAGCTA CATGTAATAC CAAGTTCTCT    300

TTAAGAGGAG AAGATGTTGA TCTTCATTTG TTTCTACCAG ACTGCCACCC TAGTAAATAT    360

TCTTTATTTA TGCTGGTAAA AAATTGCCAT CCAAATAAGA TGATTCATGA TACTGGTATT    420

CCTGCTGAGT GTCAAGTGGC CAAGCGTCA                                      449

(2) INFORMATION FOR SEQ ID NO: 193:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO: 193:

TGACGCTTGG CCACTTGACA CCAGGGATGT AKCAGTTGAA TATAATCCTG CAATTGTACA     60

TATTGGCAAT TTCCCATCAA ACATTCTAGA AAGAGACAAC CAGGATTGCT AGGCCATAAA    120

AGCTGCAATA AATAACTGGT AATTGCAGTA ATCATTTCAG GCCAATTCAA TCCAGTTTGG    180

CTCAGAGGTG CCTTTGGCTG AGAGAAGAGG TGAGATATAA TGTGTTTTCT TGCAACTTCT    240

TGGAAGAATA ACTCCACAAT AGTCTGAGGA CTAGATACAA ACCTATTTGC CATTAAAGCA    300

CCAGAGTCTG TTAATTCCAG TACTGATAAG TGTTGGAGAT TAGACTCCAG TGTGTCAAGT    360

GGCCAAGCGT CA                                                        372
```

(2) INFORMATION FOR SEQ ID NO: 194:

(i) SEQUENCE CHARACTERISTICS:
       (A) LENGTH: 309 base pairs
       (B) TYPE: nucleic acid
       (C) STRANDEDNESS: single
       (D) TOPOLOGY: linear (xi) SEQUENCE DESCRIPTION: SEQ ID NO: 194:

| | | | | | |
|---|---|---|---|---|---|
| TGACGCTTGG | CCACTTGACA | CTTATGTAGA | ATCCATCGTG | GGCTGATGCA | AGCCCTTTAT | 60 |
| TTAGGCTTAG | TGTTGTGGGC | ACCTTCAATA | TCACACTAGA | GACAAACGCC | ACAAGATCTG | 120 |
| CAGAAACATT | CAGTTCTGAN | CACTCGAATG | GCAGGATAAC | TTTTTGTGTT | GTAATCCTTC | 180 |
| ACATATACAA | AAACAAACTC | TGCANTCTCA | CGTTACAAAA | AAACGTACTG | CTGTAAAATA | 240 |
| TTAAGAAGGG | GTAAAGGATA | CCATCTATAA | CAAAGTAACT | TACAACTAGT | GTCAAGTGGC | 300 |
| CAAGCGTCA | | | | | | 309 |

(2) INFORMATION FOR SEQ ID NO: 195:

(i) SEQUENCE CHARACTERISTICS:
       (A) LENGTH: 312 base pairs
       (B) TYPE: nucleic acid
       (C) STRANDEDNESS: single
       (D) TOPOLOGY: linear (xi) SEQUENCE DESCRIPTION: SEQ ID NO: 195:

| | | | | | |
|---|---|---|---|---|---|
| TGACGCTTGG | CCACTTGACA | CCCAATCTCG | CACTTCATCC | TCCCAGCACC | TGATGAAGTA | 60 |
| GGACTGCAAC | TATCCCCACT | TCCCAGATGA | GGGGACCAAN | GTACACATTA | GGACCCGGAT | 120 |
| GGGAGCACAG | ATTTGTCCGA | TCCCAGACTC | CAAGCACTCA | GCGTCACTCC | AGGACAGCGG | 180 |
| CTTTCAGATA | AGGTCACAAA | CATGAATGGC | TCCGACAACC | GGAGTCAGTC | CGTGCTGAGT | 240 |
| TAAGGCAATG | GTGACACGGA | TGCACGTGTN | ACCTGTAATG | GTTCATCGTA | AGTGTCAAGT | 300 |
| GGCCAAGCGT | CA | | | | | 312 |

(2) INFORMATION FOR SEQ ID NO: 196:

(i) SEQUENCE CHARACTERISTICS:
       (A) LENGTH: 288 base pairs
       (B) TYPE: nucleic acid
       (C) STRANDEDNESS: single
       (D) TOPOLOGY: linear (xi) SEQUENCE DESCRIPTION: SEQ ID NO: 196:

| | | | | | |
|---|---|---|---|---|---|
| TGTATCGACG | TAGTGGTCTC | CTCAGCCATG | CAGAACTGTG | ACTCAATTAA | ACCTCTTTCC | 60 |
| TTTATGAATT | ACCCAATCTC | GGGTAGTGTC | TTTATAGTAG | TGTGAGAATG | GACTAATACA | 120 |
| AGTACATTTT | ACTTAGTAAT | AATAATAAAC | AAATATATTA | CATTTTTGTG | TATTTACTAC | 180 |
| ACCATATTTT | TTATTGTTAT | TGTAGTGTAC | ACCTTCTACT | TATTAAAAGA | AATAGGCCCG | 240 |
| AGGCGGGCAG | ATCACGAGGT | CAGGAGATGG | AGACCACTAC | GTCGATAC | | 288 |

(2) INFORMATION FOR SEQ ID NO: 197:

(i) SEQUENCE CHARACTERISTICS:
       (A) LENGTH: 289 base pairs
       (B) TYPE: nucleic acid
       (C) STRANDEDNESS: single
       (D) TOPOLOGY: linear (xi) SEQUENCE DESCRIPTION: SEQ ID NO: 197:

```
TTGGGCACCT TCAATATCAT GACAGGTGAT GTGATAACCA AGAAGGCTAC TAAGTGATTA      60

ATGGGTGGGT AATGTATACA GAGTAGGTAC ACTGGACAGA GGGGTAATTC ATAGCCAAGG     120

CAGGAGAAGC AGAATGGCAA AACATTTCAT CACACTACTC AGGATAGCAT GCAGTTTAAA     180

ACCTATAAGT AGTTTATTTT TGGAATTTTC CACTTAATAT TTTCAGACTG CAGGTAACTA     240

AACTGTGGAA CACAAGAACA TAGATAAGGG GAGACCACTA CGTCGATAC                 289

(2) INFORMATION FOR SEQ ID NO: 198:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (xi) SEQUENCE DESCRIPTION: SEQ ID NO: 198:

GTATCGACGT AGTGGTCTCC CAAGCAGTGG GAAGAAAACG TGAACCAATT AAAATGTATC      60

AGATACCCCA AGAAAGGCG CTTGAGTAAA GATTCCAAGT GGGTCACAAT CTCAGATCTT     120

AAAATTCAGG CTGTCAAAGA GATTTGCTAT GAGGTTGCTC TCAATGACTT CAGGCACAGT    180

CGGCAGGAGA TTGAAGCCCT GGCCATTGTC AAGATGAAGG AGCTTTGTGC CATGTATGGC    240

AAGAAAGACC CCAATGAGCG GGACTCCTGG AGACCACTAC GTCGATAC                 288

(2) INFORMATION FOR SEQ ID NO: 199:

(i) SEQUENCE CHARACTERISTICS:
        (A) LENGTH: 1027 base pairs
        (B) TYPE: nucleic acid
        (C) STRANDEDNESS: single
        (D) TOPOLOGY: linear (xi) SEQUENCE DESCRIPTION: SEQ ID NO: 199:

GCTTTTTGGG AAAAACNCAA NTGGGGGAAA GGGGGNTTNN TNGCAAGGGG ATAAAGGGGG      60

AANCCCAGGG TTTCCCCATT CAGGGAGGTG TAAAAAGNCG GCCAGGGGAT TGTAANAGGA    120

TTCAATAATA GGGGGAATGG GCCCNGAAGT TGCAAGGTTC CNGCCCGCCA TGNCCGCGGG    180

ATTTAGTGAC ATTACGACGS TGGTAATAAA GTGGGSCCAA WAAATATTTG TGATGTGATT    240

TTTSGACCAG TGAACCCATT GWACAGGACC TCATTTCCTY TGAGATGRTA GCCATAATCA    300

GATAAAAGRT TAGAAGTYTT TCTGCACGTT AACAGCATCA TTAAATGGAG TGGCATCACC    360

AATTTCACCC TTTGTTAGCC GATACCTTCC CCTTGAAGGC ATTCAATTAA GTGACCAATC    420

GTCATACGAG AGGGGATGGC ATGGGGATTG ATGATGATAT CAGGGGTGAT ACCTTCACAG    480

GTGAAAGGCA TATCCTCTTG TCTATACTGA ATACCACAAG TACCCTTTTG ACCATGTCGA    540

CTAGCAAATT TGTCTCCAAT CTGTGTWATC CCTAACAGAG CGTACCCTTA TTTTACAAAA    600

TTTATATCCT TCCTGATTGA GAGTTACCAT AACCTGATCC ACAATGCCCG TCTCGCTWGT    660

TCTGAGAAAA GTGCTACAGT CTCTCTTGGT ATAGCGTCTA TTGGTGCTCT CCAATTCATC    720

TTCATTTTTC AGGCAAGGTG AACTGTTTTG CCTATAATAA CMTCATCTCC TGATACMCGA    780

AACCCCKGGA RCTATCAAAC CATCATCATC CAGCGTTCKT WATGTYMCTA AATCCCTATT    840

GCGGCCGCCT GCAGGTCAAC ATATNGGAAA ACCCCCCACC CCTTNGGAGC NTACCTTGAA    900

TTTTCCATAT GTCCCNTAAA TTANCTNGNC TTANCCTGGC CNTAACCTNT TCCGGTTTAA    960

ATTGTTTCCG CCCCCNTTCC CCNCCTTNNA ACCGGAAACC TTAATTTTNA ACCNGGGGTT   1020

CCTATCC                                                             1027
```

(2) INFORMATION FOR SEQ ID NO: 200:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (xi) SEQUENCE DESCRIPTION: SEQ ID NO: 200:

```
AGTGACATTA CGACGCTGGC CATCTTGAAT CCTAGGGCAT GAAGTTGCCC CAAAGTTCAG      60

CACTTGGTTA AGCCTGATCC CTCTGGTTTA TCACAAAGAA TAGGATGGGA TAAAGAAAGT     120

GGACACTTAA ATAAGCTATA AATTATATGG TCCTTGTCTA GCAGGAGACA ACTGCACAGG     180

TATACTACCA GCGTCGTAAT GTCACTA                                        207
```

(2) INFORMATION FOR SEQ ID NO: 201:

(i) SEQUENCE CHARACTERISTICS:
        (A) LENGTH: 209 base pairs
        (B) TYPE: nucleic acid
        (C) STRANDEDNESS: single
        (D) TOPOLOGY: linear (xi) SEQUENCE DESCRIPTION: SEQ ID NO: 201:

```
TGGGCACCTT CAATATCTAT TAAAAGCACA AATACTGAAG AACACACCAA GACTATCAAT      60

GAGGTTACAT CTGGAGTCCT CGATATATCA GGAAAAAATG AAGTGAACAT TCACAGAGTT     120

TTACTTCTTT GGGAACTCAA ATGCTAGAAA AGAAAAGGGT GCCCTCTTTC TCTGGCTTCC     180

TGGTCCTATC CAGCGTCGTA ATGTCACTA                                      209
```

(2) INFORMATION FOR SEQ ID NO: 202:

(i) SEQUENCE CHARACTERISTICS:
        (A) LENGTH: 349 base pairs
        (B) TYPE: nucleic acid
        (C) STRANDEDNESS: single
        (D) TOPOLOGY: linear (xi) SEQUENCE DESCRIPTION: SEQ ID NO: 202:

```
NTACGCTGCA ACACTGTGGA GCCACTGGTT TTTATTCCCG GCAGGTTATC CAGCAAACAG      60

TCACTGAACA CACCGAAGAC CGTGGTATGG TAACCGTTCA CAGTAATCGT TCCAGTCGTC     120

TGCGGGACCC CGACGAGCGT CACTGGGTAC AGACCAGATT CAGCCGGAAG AGAAAGCGCC     180

GCAGGGAGAG ACTCGAACTC CACTCCGCTG GTGAGCAGCC CCATGTTTTC AACTCGAAGT     240

TCAAACGGCA TTGGGTTATA TACCATCAGC TGAACTTCAC ACACATCTCC TTGAACCCAC     300

TGGAAATCTA TTTTCTTGTT CCGCTCTTCT CCACAGTGTT GCAGCGTAA                349
```

(2) INFORMATION FOR SEQ ID NO: 203:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (xi) SEQUENCE DESCRIPTION: SEQ ID NO: 203:

```
TGCTCCTCTT GCCTTACCAA CCCAAAGCCC ACTGTGAAAT ATGAAGTGAA TGACAAAATT      60

CAGTTTTCAA CGCAATATAG TATAGTTTAT CTGATTCTTT TGATCTCCAG GACACTTTAA     120

ACAACTGCTA CCACCACCAC CAACCTAGGG ATTTAGGATT CTCCACAGAC CAGAAATTAT     180

TTCTCCTTTG AGTTTCAGGC TCCTCTGGGA CTCCTGTTCA TCAATGGGTG GTAAATGGCT     240
```

A                                                                          241

(2) INFORMATION FOR SEQ ID NO: 204:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (xi) SEQUENCE DESCRIPTION: SEQ ID NO: 204:

TAGCCATTTA CCACCCATCT GCAAACCSWG ACMWWCARGR CYWGWACKYA GGCGATTTGA      60

AGTACTGGTA ATGCTCTGAT CATGTTAGTT ACATAAGTGT GGTCAGTTTA CAAAAATTCA     120

CAGAACTAAA TACTCAATGC TATGTGTTCA TGTCTGTGTT TATGTGTGTG TAATGTTTCA     180

ATTAAGTTTT TTTAAAAAAA AGAGATGATT TCCAAATAAG AAAGCCGTGT TGGTAAGGCA     240

AGAGGAGC                                                              248

(2) INFORMATION FOR SEQ ID NO: 205:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (xi) SEQUENCE DESCRIPTION: SEQ ID NO: 205:

TACGCTGCAA CACTGTGGAG CCATTCATAC AGGTCCCTAA TTAAGGAACA AGTGATTATG      60

CTACCTTTGC ACGGTTAGGG TACCGCGGCC GTTAAACATG TGTCACTGGG CAGGCGGTGC     120

CTCTAATACT GGTGATGCTA GAGGTGATGT TTTTGGTAAA CAGGCGGGGT AAGATTTGCC     180

GAGTTCCTTT TACTTTTTTT AACCTTTCCT TATGAGCATG CCTGTGTTGG GTTGACAGTG     240

GGGGTAATAA TGACTTGTTG GTTGATTGTA GATATTGGGC TGTTAATTGT CAGTTCAGTG     300

TTTTAATCTG ACGCAGGCTT ATGCGGAGGA GAATGTTTTC ATGTTACTTA TACTAACATT     360

AGTTCTTCTA TAGGGTGATA GATTGGTCCA ATTGGGTGTG AGGAGTTCAG TTATATGTTT     420

GGGATTTTTT AGGTAGTGGG TGTTGANCTT GAACGCTTTC TTAATTGGTG GCTGCTTTTA     480

RGCCTACTAT GGGTGGTAAA TGGCT                                           505

(2) INFORMATION FOR SEQ ID NO: 206:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (xi) SEQUENCE DESCRIPTION: SEQ ID NO: 206:

TAGACTGACT CATGTCCCCT ACCAAAGCCC ATGTAAGGAG CTGAGTTCTT AAAGACTGAA      60

GACAGACTAT TCTCTGGAGA AAAATAAAAT GGAAATTGTA CTTTAAAAAA AAAAAAAATC     120

GGCCGGGCAT GGTAGCACAC ACCTGTAATC CCAGCTACTA GGGACATGA GTCAGTCTA      179

(2) INFORMATION FOR SEQ ID NO: 207:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (xi) SEQUENCE DESCRIPTION: SEQ ID NO: 207:

AGACTGACTC ATGTCCCCTA CCCCACCTTC TGCTGTGCTG CCGTGTTCCT AACAGGTCAC    60

AGACTGGTAC TGGTCAGTGG CCTGGGGGTT GGGGACCTCT ATTATATGGG ATACAAATTT   120

AGGAGTTGGA ATTGACACGA TTTAGTGACT GATGGGATAT GGGTGGTAAA TGGCTA       176

(2) INFORMATION FOR SEQ ID NO: 208:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (xi) SEQUENCE DESCRIPTION: SEQ ID NO: 208:

AGACTGACTC ATGTCCCCTA TTTAACAGGG TCTCTAGTGC TGTGAAAAAA AAAAATGCTG    60

AACATTGCAT ATAACTTATA TTGTAAGAAA TACTGTACAA TGACTTTATT GCATCTGGGT   120

AGCTGTAAGG CATGAAGGAT GCCAAGAAGT TTAAGGAATA TGGGTGGTAA ATGGCTAGGG   180

GACATGAGTC AGTCTA                                                   196

(2) INFORMATION FOR SEQ ID NO: 209:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 209:

GACGCTTGGC CACTTGACAC CTTTTATTTT TTAAGGATTC TTAAGTCATT TANGTNACTT    60

TGTAAGTTTT TCCTGTGCCC CCATAAGAAT GATAGCTTTA AAAATTATGC TGGGGTAGCA   120

AAGAAGATAC TTCTAGCTTT AGAATGTGTA GGTATAGCCA GGATTCTTGT GAGGAGGGGT   180

GATTTAGAGC AAATTTCTTA TTCTCCTTGC CTCATCTGTA ACATGGGGAT AATAATAGAA   240

CTGGCTTGAC AAGGTTGGAA TTAGTATTAC ATGGTAAATA CATGTAAAAT GTTTAGAATG   300

GTGCCAAGTA TCTAGGAAGT ACTTGGGCAT GGGTGGTAAA TGGCT                   345

(2) INFORMATION FOR SEQ ID NO: 210:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (xi) SEQUENCE DESCRIPTION: SEQ ID NO: 210:

GACGCTTGGC CACTTGACAC TAGAGTAGGG TTTGGCCAAC TTTTTCTATA AAGGACCAGA    60

GAGTAAATAT TTCAGGCTTT GTGGGTTGTG CAGTCTCTCT TGCAACTACT CAGCTCTGCC   120

ATTGTAGCAT AGAAATCAGC CATAGACAGG ACAGAAATGA ATGGGTGGTA AATGGCTA     178

(2) INFORMATION FOR SEQ ID NO: 211:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO: 211:

TGGGCACCTT CAATATCTAT CCAGCGCATC TAAATTCGCT TTTTTCTTGA TTAAAAATTT    60

-continued

| | | |
|---|---|---|
| CACCACTTGC TGTTTTTGCT CATGTATACC AAGTAGCAGT GGTGTGAGGC CATGCTTGTT | 120 |
| TTTTGATTCG ATATCAGCAC CGTATAAGAG CAGTGCTTTG GCCATTAATT TATCTTCATT | 180 |
| GTAGACAGCA TAGTGTAGAG TGGTATCTCC ATACTCATCT GGAATATTTG GATCAGTGCC | 240 |
| ATGTTCCAGC AACATTAACG CACATTCATC TTCCTGGCAT TGTACGGCCT TTGTCAGAGC | 300 |
| TGTCCTCTTT TTGTTGTCAA GGACATTAAG TTGACATCGT CTGTCCAGCA CGAGTTTTAC | 360 |
| TACTTCTGAA TTCCCATTGG CAGAGGCCAG ATGTAGAGCA GTCCTCTTTT GCTTGTCCCT | 420 |
| CTTGTTCACA TCAGTGTCCC TGAGCATAAC GGAA | 454 |

(2) INFORMATION FOR SEQ ID NO: 212:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO: 212:

| | |
|---|---|
| TCCGTTATGC CACCCAGAAA ACCTACTGGA GTTACTTATT AACATCAAGG CTGGAACCTA | 60 |
| TTTGCCTCAG TCCTATCTGA TTCATGAGCA CATGGTTATT ACTGATCGCA TTGAAAACAT | 120 |
| TGATCACCTG GGTTTCTTTA TTTATCGACT GTGTCATGAC AAGGAAACTT ACAAACTGCA | 180 |
| ACGCAGAGAA ACTATTAAAG GTATTCAGAA ACGTGAAGCC AGCAATTGTT TCGCAATTCG | 240 |
| GCATTTTGAA AACAAATTTG CCGTGGAAAC TTTAATTTGT TCTTGAACAG TCAAGAAAAA | 300 |
| CATTATTGAG GAAAATTAAT ATCACAGCAT AACGGAA | 337 |

(2) INFORMATION FOR SEQ ID NO: 213:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (xi) SEQUENCE DESCRIPTION: SEQ ID NO: 213:

| | |
|---|---|
| TCGGGTGATG CCTCCTCAGG CATCTTCCAT CCATCTCTTC AAGATTAGCT GTCCCAAATG | 60 |
| TTTTTCCTTC TCTTCTTTAC TGATAAATTT GGACTCCTTC TTGACACTGA TGACAGCTTT | 120 |
| AGTATCCTTC TTGTCACCTT GCAGACTTTA AACATAAAAA TACTCATTGG TTTTAAAAGG | 180 |
| AAAAAAGTAT ACATTAGCAC TATTAAGCTT GGCCTTGAAA CATTTCTAT CTTTTATTAA | 240 |
| ATGTCGGTTA GCTGAACAGA ATTCATTTTA CAATGCAGAG TGAGAAAAGA AGGGAGCTAT | 300 |
| ATGCATTTGA GAATGCAAGC ATTGTCAAAT AAACATTTTA AATGCTTTCT TAAAGTGAGC | 360 |
| ACATACAGAA ATACATTAAG ATATTAGAAA GTGTTTTTGC TTGTGTACTA CTAATTAGGG | 420 |
| AAGCACCTTG TATAGTTCCT CTTCTAAAAT TGAAGTAGAT TTTAAAAACC CATGTAATTT | 480 |
| AATTGAGCTC TCAGTTCAGA TTTTAGGAGA ATTTTAACAG GGATTTGGTT TTGTCTAAAT | 540 |
| TTTGTCAATT TNTTTAGTTA ATCTGTATAA TTTTATAAAT GTCAAACTGT ATTTAGTCCG | 600 |
| TTTTCATGCT GCTATGAAAG AAATACCCAN GACAGGGTTA TTTATAAANG GAAAGANGTT | 660 |
| AATTTGACTC CCAGTTCACA GGCCTGAGGA NGNATCNCCC GAAATCCTTA TTGCG | 715 |

(2) INFORMATION FOR SEQ ID NO: 214:

(i) SEQUENCE CHARACTERISTICS:
        (A) LENGTH: 345 base pairs
        (B) TYPE: nucleic acid
        (C) STRANDEDNESS: single (D) TOPOLOGY: linear (xi) SEQUENCE DESCRIPTION: SEQ ID NO: 214:

GGTAANGNGC ATACNTCGGT GCTCCGGCCG CCGGAGTCGG GGGATTCGGG TGATGCCTCC      60

TCAGGCCCAC TTGGGCCTGC TTTTCCCAAA TGGCAGCTCC TCTGGACATG CCATTCCTTC     120

TCCCACCTGC CTGATTCTTC ATATGTTGGG TGTCCCTGTT TTTCTGGTGC TATTTCCTGA     180

CTGCTGTTCA GCTGCCACTG TCCTGCAAAG CCTGCCTTTT TAAATGCCTC ACCATTCCTT     240

CATTTGTTTC TTAAATATGG GAAGTGAAAG TGCCACCTGA GGCCGGGCAC AGTGGCTCAC     300

GCCTGTAATC CCAGCACTTT GGGAGCCTGA GGAGGCATCA CCCGA                    345

(2) INFORMATION FOR SEQ ID NO: 215:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (xi) SEQUENCE DESCRIPTION: SEQ ID NO: 215:

GGTGATGCCT CCTCAGGCGA AGCTCAGGGA GGACAGAAAC CTCCCGTGGA GCAGAAGGGC      60

AAAAGCTCGC TTGATCTTGA TTTTCAGTAC GAATACAGAC CGTGAAAGCG GGGCCCTCACG    120

ATCCTTCTGA CCTTTTGGGT TTTAAGCAGG AGGTGTCAGA AAAGTTACCA CAGGGATAAC     180

TGGCTTGTGG CGGCCAAGCG TTCATAGCGA CGTCGCTTTT TGATCCTTCG ATGTCGGCTC     240

TTCCTATCAT TGTGAAGCAG AATTCACCAA GCGTTGGATT GTTCACCCAC TAATAGGGAA     300

CGTGAGCTGG GTTTAGACCG TCGTGAGACA GGTTAGTTTT ACCCTACTGA TGATGTGTKG     360

TTGCCATGGT AATCCTGCTC AGTACGAGAG GAACCGCAGG TTCASACATT TGGTGTATGT     420

GCTTGCCTT                                                            429

(2) INFORMATION FOR SEQ ID NO: 216:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (xi) SEQUENCE DESCRIPTION: SEQ ID NO: 216:

TGACACCTAT GTCCNGCATC TGTTCACAGT TTCCACAAAT AGCCAGCCTT TGGCCACCTC      60

TCTGTCCTGA GGTATACAAG TATATCAGGA GGTGTATACC TTCTCTTCTC TTCCCCACCA     120

AAGAGAACAT GCAGGCTCTG GAAGCTGTCT TAGGAGCCTT TGGGCTCAGA ATTTCAGAGT     180

CTTGGGTACC TTGGATGTGG TCTGGAAGGA GAAACATTGG CTCTGGATAA GGAGTACAGC     240

CGGAGGAGGG TCACAGAGCC CTCAGCTCAA GCCCCTGTGC CTTAGTCTAA AAGCAGCTTT     300

GGATGAGGAA GCAGGTTAAG TAACATACGT AAGCGTACAC AGGTAGAAAG TGCTGGGAGT     360

CAGAATTGCA CAGTGTGTAG GAGTAGTACC TCAATCAATG AGGGCAAATC AACTGAAAGA     420

AGAAGACCNA TTAATGAATT GCTTANGGGG AAGGATCAAG GCTATCATGG AGATCTTTCT     480

AGGAAGATTA TTGTTTANAA TTATGAAAGG ANTAGGGCAG GGACAGGGCC AGAAGTANAA     540

GANAACATTG CCTATANCCC TTGTCTTGCA CCCAGATGCT GGACAAGGTG TCA           593

(2) INFORMATION FOR SEQ ID NO: 217:

(i) SEQUENCE CHARACTERISTICS:
        (A) LENGTH: 335 base pairs (B) TYPE: nucleic acid
        (C) STRANDEDNESS: single
        (D) TOPOLOGY: linear (xi) SEQUENCE DESCRIPTION: SEQ ID NO: 217:

TGACACCTTG TCCAGCATCT GACGTGAAGA TGAGCAGCTC AGAGGAGGTG TCCTGGATTT        60

CCTGGTTCTG TGGGCTCCGT GGCAATGAAT TCTTCTGTGA AGTGGATGAA GACTACATCC       120

AGGACAAATT TAATCTTACT GGACTCAATG AGCAGGTCCC TCACTATCGA CAAGCTCTAG       180

ACATGATCTT GGACCTGGAG CCTGATGAAG AACTGGAAGA CAACCCCAAC CAGAGTGACC       240

TGATTGAGCA GGCAGCCGAG ATGCTTTATG GATTGATCCA CGCCCGCTAC ATCCTTACCA       300

ACCGTGGCAT CGCCCAGATG CTGGACAAGG TGTCA                                 335

(2) INFORMATION FOR SEQ ID NO: 218:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (xi) SEQUENCE DESCRIPTION: SEQ ID NO: 218:

TACGTACTGG TCTTGAAGGT CTTAGGTAGA GAAAAAATGT GAATATTTAA TCAAAGACTA        60

TGTATGAAAT GGGACTGTAA GTACAGAGGG AAGGGTGGCC CTTATCGCCA GAAGTTGGTA       120

GATGCGTCCC CGTCATGAAA TGTTGTGTCA CTGCCCGACA TTTGCCGAAT TACTGAAATT       180

CCGTAGAATT AGTGCAAATT CTAACGTTGT TCATCTAAGA TTATGGTTCC ATGTTTCTAG       240

TACTTTTA                                                               248

(2) INFORMATION FOR SEQ ID NO: 219:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (xi) SEQUENCE DESCRIPTION: SEQ ID NO: 219:

TGACGCTTGG CCACTTGACA CAAGTAGGGG ATAAGGACAA AGACCCATNA GGTGGCCTGT        60

CAGCCTTTTG TTACTGTTGC TTCCCTGTCA CCACGGCCCC CTCTGTAGGG GTGTGCTGTG       120

CTCTGTGGAC ATTGGTGCAT TTTCACACAT ACCATTCTCT TTCTGCTTCA CAGCAGTCCT       180

GAGGCGGGAG CACACAGGAC TACCTTGTCA GATGANGATA ATGATGTCTG GCCAACTCAC       240

CCCCCAACCT TCTCACTAGT TATANGAAGA GCCANGCCTA NAACCTTCTA TCCTGNCCCC       300

TTGCCCTATG ACCTCATCCC TGTTCCATGC CCTATTCTGA TTTCTGGTGA ACTTTGGAGC       360

AGCCTGGTTT NTCCTCCTCA CTCCAGCCTC TCTCCATACC ATGGTANGGG GGTGCTGTTC       420

CACNCAAANG GTCAGGTGTG TCTGGGGAAT CCTNANANCT GCCNGGAGTT TCCNANGCAT       480

TCTTAAAAAC CTTCTTGCCT AATCANATNG TGTCCAGTGG CCAACCNTCN                 530

(2) INFORMATION FOR SEQ ID NO: 220:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (xi) SEQUENCE DESCRIPTION: SEQ ID NO: 220:

```
TGACGCTTGG CCACTTGACA CTAAATAGCA TCTTCTAAAG GCCTGATTCA GAGTTGTGGA        60

AAATTCTCCC AGTGTCAGGG ATTGTCAGGA ACAGGGCTGC TCCTGTGCTC ACTTTACCTG       120

CTGTGTTTCT GCTGGAAAAG GAGGGAAGAG GAATGGCTGA TTTTTACCTA ATGTCTCCCA       180

GTTTTTCATA TTCTTCTTGG ATCCTCTTCT CTGACAACTG TTCCCTTTTG GTCTTCTTCT       240

TCTTGCTCAG AGAGCAGGTC TCTTTAAAAC TGAGAAGGGA GAATGAGCAA ATGATTAAAG       300

AAAACACACT TCTGAGGCCC AGAGATCAAA TATTAGGTAA ATACTAAACC GCTTGCCTGC       360

TGTGGTCACT TTTCTCCTCT TTCACATGCT CTATCCCTCT ATCCCCACC  TATTCATATG       420

GCTTTTATCT GCCAAGTTAT CCGGCCTCTC ATCAACCTTC TCCCCTAGCC TACTGGGGA        480

TATCCATCTG GGTCTGTCTC TGGTGTATTG GTGTCAAGTG GCCAAGCGTC A                531

(2) INFORMATION FOR SEQ ID NO: 221:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (xi) SEQUENCE DESCRIPTION: SEQ ID NO: 221:

ATTGACGCTT GGCCACTTGA CACCCGCCTG CCTGCAATAC TGGGGCAAGG GCCTTCACTG        60

CTTTCCTGCC ACCAGCTGCC ACTGCACACA GAGATCAGAA ATGCTACCAA CCAAGACTGT      120

TGGTCCTCAG CCTCTCTGAG GAGAAAGAGC AGAAGCCTGG AAGTCAGAAG AGAAGCTAGA      180

TCGGCTACGG CCTTGGCAGC CAGCTTCCCC ACCTGTGGCA ATAAAGTCGT GCATGGCTTA      240

ACAATGGGGG CACCTCCTGA GAAACACATT GTTAGGCAAT TCGGCGTGTG TTCATCAGAG      300

CATATTTACA CAAACCTCGA TAGTGCAGCC TACTATCCAC TATTGCTCCT ACGCTGCAAA      360

CCTGAACAGC ATGGGACTGT ACTGAATACT GGAAGCAGCT GGTGATGGTA CTTATTTGTG      420

TATCTAAACA CAGAGAAGGT ACAGTAAGAA TATGGTATCA TAAACTTACA GGGACCGCCA      480

TCCTATATGC AGTCTGTTGT GACCAAAATG TGTCAAGTGG CCAAGCGTCA                  530

(2) INFORMATION FOR SEQ ID NO: 222:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 222:

TGTATCGACG TAGTGGTCTC CGGGCTACTA GGCCGTTGTG TGCTGGTAGT ACCTGGTTCA        60

CTGAAAGGCG CATCTCCCTC CCCGCGTCGC CCTGAAGCAG GGGGAGGACT TCGCCCAGCC      120

AAGGCAGTTG TATGAGTTTT AGCTGCGGCA CTTCAGACC  TCTGAGCCCA CCTCCTTCAG      180

GAGCCTTCCC CGATTAAGGA AGCCAGGGTA AGGATTCCTT CCTCCCCCAG ACACCACGAA      240

CAAACCACCA CCCCCCCTAT TCTGGCAGCC CATATACATC AGAACGAAAC AAAAATAACA      300

AATAAACNAA AACCAAAAAA AAAAGAGAAG GGGAAATGTA TATGTCTGTC CATCCTGTTG      360

CTTTAGCCTG TCAGCTCCTA NAGGGCAGGG ACCGTGTCTT CCGAATGGTC TGTGCAGCGC      420

CGACTGCGGG AAGTATCGGA GGAGGAAGCA GAGTCAGCAG AAGTTGAACG GTGGGCCCGG      480

CGGCTCTTGG GGGCTGGTGT TGTACTTCGA GACCGCTTTC GCTTTTTGTC TTAGATTTAC      540

GTTTGCTCTT TGGAGTGGGA NACCACTACN TCNATACA                              578
```

(2) INFORMATION FOR SEQ ID NO: 223:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (xi) SEQUENCE DESCRIPTION: SEQ ID NO: 223:

```
TGTATCGACG TAGTGGTCTC CTCTTGCAAA GGACTGGCTG GTGAATGGTT TCCCTGAATT      60
ATGGACTTAC CCTAAACATA TCTTATCATC ATTACCAGTT GCAAAATATT AGAATGTGTT     120
GTCACTGTTT CATTTGATTC CTAGAAGGTT AGTCTTAGAT ATGTTACTTT AACCTGTATG     180
CTGTAGTGCT TTGAATGCAT TTTTTGTTTG CATTTTTGTT TGCCCAACCT GTCAATTATA     240
GCTGCTTAGG TCTGGACTGT CCTGGATAAA GCTGTTAAAA TATTCACCAG TCCAGCCATC     300
TTACAAGCTA ATTAAGTCAA CTAAATGCTT CCTTGTTTTG CCAGACTTGT TATGTCAATC     360
CTCAATTTCT GGGTTCATTT TGGGTGCCCT AAATCTTAGG GTGTGACTTT CTTAGCATCC     420
TGTAACATCC ATTCCCAAGC AAGCACAACT TCACATAATA CTTTCCAGAA GTTCATTGCT     480
GAAGCCTTTC CTTCACCCAG CGGAGCAACT TGATTTTCTA CAACTTCCCT CATCAGAGCC     540
ACAAGAGTAT GGGATATGGA GACCACTACG TCGATACA                             578
```

(2) INFORMATION FOR SEQ ID NO: 224:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO: 224:

```
TGTATCGACG TANTGGTCTC CCAAGGTGCT GGGATTGCAG GCATGAGCCA CCACTCCCAG      60
GTGGATCTTT TTCTTTATAC TTACTTCATT AGGTTTCTGT TATTCAAGAA GTGTAGTGGT     120
AAAAGTCTTT TCAATCTACA TGGTTAAATA ATGATAGCCT GGGAAATAAA TAGAAATTTT     180
TTCTTTCATC TTTAGGTTGA ATAAAGAAAC AGAAAAAATA GAACATACTG AAAATAATCT     240
AAGTTCCAAC CATAGAAGAA CTGCAGAAGA AATGAAGAAA GTGATGATGA TTTAGATTTT     300
GATATTGATT TAGAAGACAC AGGAGGAGAC CACTACGTCG ATACA                     345
```

(2) INFORMATION FOR SEQ ID NO: 225:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (xi) SEQUENCE DESCRIPTION: SEQ ID NO: 225:

```
TGTATCGACG TAGTGGTCTC CAAACTGAGG TATGTGTGCC ACTAGCACAC AAAGCCTTCC      60
AACAGGGACG CAGGCACAGG CAGTTTAAAG GGAATCTGTT TCTAAATTAA TTTCCACCTT     120
CTCTAAGTAT TCTTTCCTAA AACTGATCAA GGTGTGAAGC CTGTGCTCTT TCCCAACTCC     180
CCTTTGACAA CAGCCTTCAA CTAACACAAG AAAAGGCATG TCTGACACTC TTCCTGAGTC     240
TGACTCTGAT ACGTTGTTCT GATGTCTAAA GAGCTCCAGA ACACCAAAGG GACAATTCAG     300
AATGCTGGTG TATAACAGAC TCCAATGGAG ACCACTACGT CGATACA                   347
```

(2) INFORMATION FOR SEQ ID NO: 226:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (xi) SEQUENCE DESCRIPTION: SEQ ID NO: 226:

| | | | | | |
|---|---|---|---|---|---|
| AGGNGNGGGA | NTGTATCGAC | GTAGTGGTCT | CCCAACAGTC | TGTCATTCAG TCTGCAGGTG | 60 |
| TCAGTGTTTT | GGACAATGAG | GCACCATTGT | CACTTATTGA | CTCCTCAGCT CTAAATGCTG | 120 |
| AAATTAAATC | TTGTCATGAC | AAGTCTGGAA | TTCCTGATGA | GGTTTTACAA AGTATTTTGG | 180 |
| ATCAATACTC | CAACAAATCA | GAAAGCCAGA | AAGAGGATCC | TTTCAATATT GCAGAACCAC | 240 |
| GAGTGGATTT | ACACACCTCA | GGAGACCACT | ACGTCGATAC | A | 281 |

(2) INFORMATION FOR SEQ ID NO: 227:

(i) SEQUENCE CHARACTERISTICS:
        (A) LENGTH: 3646 base pairs
        (B) TYPE: nucleic acid
        (C) STRANDEDNESS: single
        (D) TOPOLOGY: linear (xi) SEQUENCE DESCRIPTION: SEQ ID NO: 227:

| | | | | | |
|---|---|---|---|---|---|
| GGGAAACACT | TCCTCCCAGC | CTTGTAAGGG | TTGGAGCCCT | CTCCAGTATA TGCTGCAGAA | 60 |
| TTTTTCTCTC | GGTTTCTCAG | AGGATTATGG | AGTCCGCCTT | AAAAAAGGCA AGCTCTGGAC | 120 |
| ACTCTGCAAA | GTAGAATGGC | CAAAGTTTGG | AGTTGAGTGG | CCCCTTGAAG GGTCACTGAA | 180 |
| CCTCACAATT | GTTCAAGCTG | TGTGGCGGGT | TGTTACTGAA | ACTCCCGGCC TCCCTGATCA | 240 |
| GTTTCCCTAC | ATTGATCAAT | GGCTGAGTTT | GGTCAGGAGC | ACCCCTTCCG TGGCTCCACT | 300 |
| CATGCACCAT | TCATAATTTT | ACCTCCAAGG | TCCTCCTGAG | CCAGACCGTG TTTTCGCCTC | 360 |
| GACCCTCAGC | CGGTTCGGCT | CGCCCTGTAC | TGCCTCTCTC | TGAAGAAGAG GAGAGTCTCC | 420 |
| CTCACCCAGT | CCCACCGCCT | TAAAACCAGC | CTACTCCCTT | AGGGTCATCC CATGTCTCCT | 480 |
| CGGCTATGTC | CCCTGTAGGC | TCATCACCCA | TTGCCTCTTG | GTTGCAACCG TGGTGGGAGG | 540 |
| AAGTAGCCCC | TCTACTACCA | CTGAGAGAGG | CACAAGTCCC | TCTGGGTGAT GAGTGCTCCA | 600 |
| CCCCCTTCCT | GGTTTATGTC | CCTTCTTTCT | ACTTCTGACT | TGTATAATTG GAAAACCCAT | 660 |
| AATCCTCCCT | TCTCTGAAAA | GCCCCAGGCT | TTGACCTCAC | TGATGGAGTC TGTACTCTGG | 720 |
| ACACATTGGC | CCACCTGGGA | TGACTGTCAA | CAGCTCCTTT | TGACCCTTTT CACCTCTGAA | 780 |
| GAGAGGGAAA | GTATCCAAAG | AGAGGCCAAA | AAGTACAACC | TCACATCAAC CAATAGGCCG | 840 |
| GAGGAGGAAG | CTAGAGGAAT | AGTGATTAGA | GACCCAATTG | GGACCTAATT GGGACCCAAA | 900 |
| TTTCTCAAGT | GGAGGGAGAA | CTTTTGACGA | TTTCCACCGG | TATCTCCTCG TGGGTATTCA | 960 |
| GGGAGCTGCT | CAGAAACCTA | TAAACTTGTC | TAAGGCGACT | GAAGTCGTCC AGGGGCATGA | 1020 |
| TGAGTCACCA | GGAGTGTTTT | TAGAGCACCT | CCAGGAGGCT | TATCAGATTT ACACCCCTTT | 1080 |
| TGACCTGGCA | GCCCCCGAAA | ATAGCCATGC | TCTTAATTTG | GCATTTGTGG CTCAGGCAGC | 1140 |
| CCAGATAGT | AAAAGGAAAC | TCCAAAAACT | AGAGGGATTT | TGCTGGAATG AATACCAGTC | 1200 |
| AGCTTTTAGA | GATAGCCTAA | AAGGTTTTTG | ACAGTCAAGA | GGTTGAAAAA CAAAACAAG | 1260 |
| CAGCTCAGGC | AGCTGAAAAA | AGCCACTGAT | AAAGCATCCT | GGAGTATCAG AGTTTACTGT | 1320 |
| TAGATCAGCC | TCATTTGACT | TCCCCTCCCA | CATGGTGTTT | AAATCCAGCT ACACTACTTC | 1380 |
| CTGACTCAAA | CTCCACTATT | CCTGTTCATG | ACTGTCAGGA | ACTGTTGGAA ACTACTGAAA | 1440 |
| CTGGCCGACC | TGATCTTCAA | AATGTGCCCC | TAGGAAAGGT | GGATGCCACC ATGTTCACAG | 1500 |

```
ACAGTAGCAG CTTCCTCGAG AAGGGACTAC GAAAGGCCGG TGCAGCTGTT ACCATGGAGA    1560

CAGATGTGTT GTGGGCTCAG GCTTTACCAG CAAACACCTC AGCACAAAAG GCTGAATTGA    1620

TCGCCCTCAC TCAGGCTCTC CGATGGGGTA AGGATATTAA CGTTAACACT GACAGCAGGT    1680

ACGCCTTTGC TACTGTGCAT GTACGTGGAG CCATCTACCA GGAGCGTGGG CTACTCACCT    1740

CAGCAGGTGG CTGTAATCCA CTGTAAAGGA CATCAAAAGG AAAACACGGC TGTTGCCCGT    1800

GGTAACCAGA AAGCTGATTC AGCAGCTCAA GATGCAGTGT GACTTTCAGT CACGCCTCTA    1860

AACTTGCTGC CCACAGTCTC CTTTCCACAG CCAGATCTGC CTGACAATCC CGCATACTCA    1920

ACAGAAGAAG AAAACTGGCC TCAGAACTCA GAGCCAATAA AAATCAGGAA GGTTGGTGGA    1980

TTCTTCCTGA CTCTAGAATC TTCATACCCC GAACTCTTGG GAAAACTTTA ATCAGTCACC    2040

TACAGTCTAC CACCCATTTA GGAGGAGCAA AGCTACCTCA GCTCCTCCGG AGCCGTTTTA    2100

AGATCCCCCA TCTTCAAAGC CTAACAGATC AAGCAGCTCT CCGGTGCACA ACCTGCGCCC    2160

AGGTAAATGC CAAAAAGGT CCTAAACCCA GCCCAGGCCA CCGTCTCCAA GAAAACTCAC    2220

CAGGAGAAAA GTGGGAAATT GACTTTACAG AAGTAAAACC ACACCGGGCT GGGTACAAAT    2280

ACCTTCTAGT ACTGGTAGAC ACCTTCTCTG GATGGACTGA AGCATTTGCT ACCAAAAACG    2340

AAACTGTCAA TATGGTAGTT AAGTTTTTAC TCAATGAAAT CATCCCTCGA CATGGGCTGC    2400

CTGTTTGCCA TAGGGTCTGA TAATGGACCG GCCTTCGCCT TGTCTATAGT TTAGTCAGTC    2460

AGTAAGGCGT TAAACATTCA ATGGAAGCTC CATTGTGCCT ATCGACCCCA GAGCTCTGGG    2520

CAAGTAGAAC GCATGAACTG CACCCTAAAA AACACTCTTA CAAAATTAAT CTTAGAAACC    2580

GGTGTAAATT GTGTAAGTCT CCTTCCTTTA GCCCTACTTA GAGTAAGGTG CACCCCTTAC    2640

TGGGCTGGGT TCTTACCTTT TGAAATCATG TATGGGAGGG TGCTGCCTAT CTTGCCTAAG    2700

CTAAGAGATG CCCAATTGGC AAAAATATCA CAAACTAATT TATTACAGTA CCTACAGTCT    2760

CCCCAACAGG TACAAGATAT CATCCTGCCA CTTGTTCGAG GAACCCATCC CAATCCAATT    2820

CCTGAACAGA CAGGGCCCTG CCATTCATTC CCGCCAGGTG ACCTGTTGTT TGTTAAAAAG    2880

TTCCAGAGAG AAGGACTCCC TCCTGCTTGG AAGAGACCTC ACACCGTCAT CACGATGCCA    2940

ACGGCTCTGA AGGTGGATGG CATTCCTGCG TGGATTCATC ACTCCCGCAT CAAAAAGGCC    3000

AACAGAGCCC AACTAGAAAC ATGGGTCCCC AGGGCTGGGT CAGGCCCCTT AAAACTGCAC    3060

CTAAGTTGGG TGAAGCCATT AGATTAATTC TTTTTCTTAA TTTTGTAAAA CAATGCATAG    3120

CTTCTGTCAA ACTTATGTAT CTTAAGACTC AATATAACCC CCTTGTTATA ACTGAGGAAT    3180

CAATGATTTG ATTCCCCCAA AAACACAAGT GGGGAATGTA GTGTCCAACC TGGTTTTTAC    3240

TAACCCTGTT TTTAGACTCT CCCTTTCCTT TAATCACTCA GCTTGTTTCC ACCTGAATTG    3300

ACTCTCCCTT AGCTAAGAGC GCCAGATGGA CTCCATCTTG GCTCTTTCAC TGGCAGCCGC    3360

TTCCTCAAGG ACTTAACTTG TGCAAGCTGA CTCCCAGCAC ATCCAAGAAT GCAATTAACT    3420

GATAAGATAC TGTGGCAAGC TATATCCGCA GTTCCCAGGA ATTCGTCCAA TTGATCACAG    3480

CCCCTCTACC CTTCAGCAAC CACCACCCTG ATCAGTCAGC AGCCATCAGC ACCGAGGCAA    3540

GGCCCTCCAC CAGCAAAAAG ATTCTGACTC ACTGAAGACT TGGATGATCA TTAGTATTTT    3600

TAGCAGTAAA GTTTTTTTTT CTTTTCTTT CTTTTTTTCT CGTGCC                   3646
```

(2) INFORMATION FOR SEQ ID NO: 228:

(i) SEQUENCE CHARACTERISTICS:
        (A) LENGTH: 419 base pairs
        (B) TYPE: nucleic acid
        (C) STRANDEDNESS: single (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 228:

```
TAAGAGGGTA CAAGATCTAA GCACAGCCGT CAATGCAGAA CACAGAACGT AGCCTGGTAA    60

GTGTGTTAAG AGTGGGAATT TTTGGAGTAC AGAGTAAGGC ACCTAACCCT AGCTGGGGTT   120

TGGTGACGGT CCCAGATGGC TTACAGAAGA AAGTGTCCTG AGATGAGTTT TTAAGAATGA   180

ATAAGGATAG ACACAAGTGA GGACTGACTT GGCAGTGGTG AATGGTGGGT GGCAAAAAAC   240

TTCGCATGTA TGGAAACTGC ACGTACAGGA ATGAAGAATG AGACTGTGTG GTGTTTAATG   300

AGCTGCAAAT ACTAATTTTA TCCTGAAAGT TTTGAAGAGT TAACTAAAAA GTATTTTTA   360

GTAAGGAAAT AACCCTACAT TTCAGGGTTA TTGTTTGTTT ANATATTGAA GGTGCCCAA    419
```

(2) INFORMATION FOR SEQ ID NO: 229:

(i) SEQUENCE CHARACTERISTICS:
        (A) LENGTH: 148 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 229:

```
AAGAGGGTAC CTGTATGTAG CCATGGTGGC AATGAGAGAC TGATTACTAC CTGCTGGAGA    60

TTGTTTAAGT GAGTTAATAT ATTAAGGATA AAGGGAGCCA GGTTTTTTGA CTGTTGGAGA   120

AGGAAATTAC AGATATTGAA GGTCCCAA                                     148
```

(2) INFORMATION FOR SEQ ID NO: 230:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO: 230:

```
TAAGAGGGTA CMAAAAAAA AAAATAGAAC GAATGAGTAA GACCTACTAT TTGATAGTAC    60

AACAGGGTGA CTATAGTCAA TGATAACTTA ATTATACATT TAACATAGAG TGTAATTGGA   120

TTGTTTGTAA CTCGAAGGAT AAATGCTTGA GAGGATGGAT ACCCCATTCT CCATGATGTA   180

CTTATTTCAC ATTACATGCC TGTATCAAAG CATCTCATAT ACCCTATAAA TATGTACACC   240

TACTATGTAC CCTCTTA                                                 257
```

(2) INFORMATION FOR SEQ ID NO: 231:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 231:

TAAGAGGGTA CGGGTATTTG CTGATGGGAT TTTTTTTTCT TTCTTTTTCT TTGGAAAACA    60

AAATGAAAGC CAGAACAAAA TTATTGAACA AAAGACAGGG ACTAAATCTG GAGAAATGAA   120

GTCCCCTCAC CTGACTGCCA TTTCATTCTA TCTGACCTTC CAGTCTAGGT TAGGAGAATA   180

GGGGGTGGAG GGGATTAATC TGATACAGGT ATATTTAAAG CAACTCTGCA TGTGTGCCAG   240

AAGTCCATGG TACCCTCTTA                                               260

(2) INFORMATION FOR SEQ ID NO: 232:

(i) SEQUENCE CHARACTERISTICS:
            (A) LENGTH: 596 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 232:

TGCTCCTCTT GCCTTACCAA CCACAAATTA GAACCATAAT GAGATGTCAC CTCATACCTG    60

GTGGGATTAA CATTATTTAA AAAATCAGAA GTATTGACAA GGATGTGAAG AAATTAGAAC   120

ATCTGTGCAC TGTTGGTGGG AATGTAAAAA AGGTGTGGCC ACTATGGGTA ACAGCATGAA   180

GGTTCCTCAA AAAAAATTTT TTTTAATCTA CTCTATGATC GATCTTGAGG TTGTTTATGC   240

AAAAGAACTG AAATCAGGAT TTTGAGGAAA TATTCACATT CCCACATCCA TTTCTGCTTT   300

ATTCATAATA CTCAAGAGAT GGAAACAACC TAAATGTCCA TCCCGGGATG AATGGATAAA   360

CACAGTGTGG TATATGCATA CAATGGAATA TTATTTAGTC TTTAAAAGA AAAATTCTAT    420

CATATACTAC AACTTANATN AACCTTGAGG ACACAATGCT NAGTGAAATA AGCCACGGAA   480

GGACGAATAC TGCATTATTC CCTTATATGA AGTATCTAAA GTGGTCAAAC TCTTANAGCA   540

NAAAGTAAAA ATGGGTGGTT GCCANACAGT TGGTTAGGCN AGAAGANAAN CCTANT       596

(2) INFORMATION FOR SEQ ID NO: 233:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 233:

TCTTCTGAAG ACCTTTCGCG ACTCTTAAGC TCGTGGTTGG TAAGGCAAGA GGAGCGTTGG    60

TAAGGCAAGA GGAGCGTTGG TAAGGCAAGA GGAGCA                             96

(2) INFORMATION FOR SEQ ID NO: 234:

(i) SEQUENCE CHARACTERISTICS:
            (A) LENGTH: 313 base pairs (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 234:

```
TGTAAGTCGA GCAGTGTGAT GATAAAACTT GAATGGATCA ATAGTTGCTT CTTATGGATG      60

AGCAAAGAAA GTAGTTTCTT GTGATGGAAT CTGCTCCTGG CAAAAATGCT GTGAACGTTG     120

TTGAAAAGAC AACAAAGAGT TTAGAGTAGT ACATAAATTT AGAATAGTAC ATAAACTTAG     180

AATAGTACAT AAACTTAGTA CATAAATAAT GCACGAAGCA GGGGCAGGGC TTAGAGAAT      240

TGACTTCAAT TTGGAAAGAG TATCTACTGT AGGTTAGATG CTCTCAAACA GCATCACACT     300

GCTCGACTTA CAA                                                       313
```

(2) INFORMATION FOR SEQ ID NO: 235:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 235:

```
AACGAGGACA GATCCTTAAA AAGAATGTTG AGTGAAAAAA GTAGAAAATA AGATAATCTC      60

CAAAGTCCAG TAGCATTATT TAAACATTTT TAAAAAATAC ACTGATAAAA ATTTTGTACA     120

TTTCCCAAAA ATACATATGG AAGCACAGCA GCATGAATGC CTATGGGRTT GAGGATAGGG     180

GTTGGGAGTA GGGATGGGGA TAAAGGGGGA AAATAAAACC AGAGAGGAGT CTTACACATT     240

TCATGAACCA AGGAGTATAA TTATTTCAAC TATTTGTACC WGAAGTCCAG AAAGAGTGGA     300

GGCAGAAGGG GGAGAAGAGG GCGAAGAAAC GTTTTTGGGA GAGGGGTCCC ASAAGAGAGA     360

TTTTCGCGAT GTGGCGCTAC ATACGTTTTT CCAGGATGCC TTAAGCTCTG CACCCTATTT     420

TTCTCATCAC TAATATTAGA TTAAACCCTT TGAAGACAGC GTCTGTGGTT TCTCTACTTC     480

AGCTTTCCCT CCGTGTCTTG CACACAGTAG CTGTTTTACA AGGGTTGAAC TGACTGAAGT     540

GAGATTATTC                                                           550
```

(2) INFORMATION FOR SEQ ID NO: 236:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 236:

```
TAGACTGACT CATGTCCCCT ACCAGAGTAG CTAGAATTAA TAGCACAAGC CTCTACACCC      60

AGGAACTCAC TATTGAATAC ATAAATGGAA TTTATTCAGC CTTAAAAAGT TTGGAAGGAA     120
```

| | |
|---|---|
| ATTCTGACAT ATGCTAAAAC ATGGATGAAC CTTGAAGACT TTATGATAAG TAAAAGAAGC | 180 |
| CAGTCATAAA AGGAAAAATA TTGCATGATT CCACTTATAT GAGGTACCTA GAGTAGTCAA | 240 |
| TTTCATAGAA ACACAAAATA GAATGGTGTT TGCCAGGGCT TTTGAGGAAA AGGGAATGAC | 300 |
| AAGTTAGGGG ACATGAGTCA GTCTA | 325 |

(2) INFORMATION FOR SEQ ID NO: 237:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 237:

| | |
|---|---|
| TAGACTGACT CATGTCCCCT ATCTACTCAA CATTTCCACT TGAAGTCTGA TAGGCATCTC | 60 |
| AGACTTATCT TGTCCCAAAG CAAACTCTTT ATTTCTTTTC ATCCTAGTCT TTATTTCTTG | 120 |
| TGCTGTCTTA CCCATCTCAA AAGAGTGCCA AAATCCACCA AGTTGCTGAA ACAGAAATCT | 180 |
| AAGAAATATC CTTGATTCTT CTTTTTCCCA TCTACTTCAC TTCTAATTCA TTAGTAAATA | 240 |
| ATCTGTTTCA GAAACCAAA CACCTCATGT TCTCACTCAT AAGGGGGAGT TGAACAATGA | 300 |
| GAACACACAG ACACAGGGAG GGGAACATCA CACACCACGG CCCGTCAGGG AGTANGGGAC | 360 |
| ATGAGTCAGT CTA | 373 |

(2) INFORMATION FOR SEQ ID NO: 238:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 238:

| | |
|---|---|
| TAGACTGACT CATGTCCCCT ATAATGCTCC CAGGCATCAG AAAGCATCTC AAACTGGAGC | 60 |
| TGACACCATG GCAGAGGTTT CAGGTAAGTC ACAAAAGGGG TCCTAAAGAA TTTGCCCTCA | 120 |
| ATATCAGAGT GATTAGAAGA AGTGGACAGA GCTACCCAAG TTAAACATAT GCGAGATAAA | 180 |
| AAAAATATGG CACTTGTGAA CACACACTAC AGGAGGAAAA TAAGGAACAT AATAGCATAT | 240 |
| TGTGCTATTA TGATGATGAA GAACCTCTCT ANAAGAAAAC ATAACCAAAG AAACAAAGAA | 300 |
| AATTCCTGCN AATGTTTAAT GCTATAGAAG AAATTAACAA AAACATATAT TCAATGAATT | 360 |
| CAGAAAAGTT AGCAGGTCAN AAGAAAACAA ATCAAAGACC AGAATAATCC CATTTTAGAT | 420 |
| TGTCGAGTAA ACTANAACAG AAAGAATACC ACTGGAAATT GAATTCCTAC GTANGGGACA | 480 |
| TGANTCANTC TA | 492 |

(2) INFORMATION FOR SEQ ID NO: 239:

(i) SEQUENCE CHARACTERISTICS:
        (A) LENGTH: 482 base pairs
        (B) TYPE: nucleic acid
        (C) STRANDEDNESS: single (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 239:

| | | | | | |
|---|---|---|---|---|---|
| TGGAAAGTAT | TTAATGATGG | GCAACTTGCT | GTTTACTTCC | TACATATCCC | ATCATCTTCT | 60 |
| GTATTTTTTT | AAATAACTTT | TTTTTGGATT | TTTAAAGTAA | CCTTATTCTG | AGAGGTAACA | 120 |
| TGGATTACAT | ACTTCTAAGC | CATTAGGAGA | CTCTATGTTA | AACCAAAAGG | AAATGTTACT | 180 |
| AGATCTTCAT | TTGATCAATA | GGATGTGATA | ATCATCATCT | TTCTGCTCTA | ATGGAAAAGT | 240 |
| ACTANAAACA | TGGAACCATA | ATCTTAGATG | AACAACGTTA | GAATTTGCAC | TAATTCTACG | 300 |
| GAATTTCAGT | AATTCGGCAA | ATGTCGGGCA | GTGACACAAC | ATTTCATGAC | GGGGACGCAT | 360 |
| CTACCAACTT | CTGGCGATAA | GGGCCACCCT | TCCCTCTGTA | CTTACAGTCC | CATTTCATAC | 420 |
| ACAGTCTTTG | ATTAAATATT | CACATTTTTT | CTCTACCTAA | AGACCTTCAA | GACCAGTACG | 480 |
| TA | | | | | | 482 |

(2) INFORMATION FOR SEQ ID NO: 240:

(i) SEQUENCE CHARACTERISTICS:
            (A) LENGTH: 519 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 240:

| | | | | | |
|---|---|---|---|---|---|
| TGTATCGACG | TAGTGGTCTC | CCCATGTGAT | AGTCTGAAAT | ATAGCCTCAT | GGGATGAGAG | 60 |
| GCTGTGCCCC | AGCCCGACAC | CCGTAAAGGG | TCTGTGCTGA | GGTGGATTAG | TAAAAGAGGA | 120 |
| AAGCCTTGCA | GTTGAGATAG | AGGAAGGGCA | CTGTCTCCTG | CCTGCCCCTG | GGAACTGAAT | 180 |
| GTCTCGGTAT | AAAACCCGAT | TGTACATTTG | TTCAATTCTG | AGATAGGAGA | AAAACCACCC | 240 |
| TATGGCGGGA | GGCGAGACAT | GTTGGCAGCA | ATGCTGCCTT | GTTATGCTTT | ACTCCACAGA | 300 |
| TGTTTGGGCG | GAGGGAAACA | TAAATCTGGC | CTACGTGCAC | ATCCAGGCAT | AGTACCTCCC | 360 |
| TTTGAACTTA | ATTATGACAC | AGATTCCTTT | GCTCACATGT | TTTTTTGCTG | ACCTTCTCCT | 420 |
| TATTATCACC | CTGCTCTCCT | ACCGCATTCC | TTGTGCTGAG | ATAATGAAAA | TAATATCAAT | 480 |
| AAAAACTTGA | NGGAACTCGG | AGACCACTAC | GTCGATACA | | | 519 |

(2) INFORMATION FOR SEQ ID NO: 241:

(i) SEQUENCE CHARACTERISTICS:
            (A) LENGTH: 771 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 241:

| | | | | | |
|---|---|---|---|---|---|
| TGTATCGACG | TAGTGGTCTC | CACTCCCGCC | TTGACGGGGC | TGCTATCTGC | CTTCCAGGCC | 60 |

```
ACTGTCACGG CTCCCGGGTA GAAGTCACTT ATGAGACACA CCAGTGTGGC CTTGTTGGCT      120

TGAAGCTCCT CAGAGGAGGG TGGGAACAGA GTGACCGAGG GGGCAGCCTT GGGCTGACCT      180

AGGACGGTCA GCTTGGTCCC TCCGCCAAAC ACGAGAGTGC TGCTGCTTGT ATATGAGCTG      240

CAGTAATAAT CAGCCTCGTC CTCAGCCTGG AGCCCAGAGA TGGTCAGGGA GGCCGTGTTG      300

CCANACTTGG AGCCAGAGAA GCGATTAGAA ACCCCTGAGG GCCGATTACC GACCTCATAA      360

ATCATGAATT TGGGGGCTTT GCCTGGGTGC TGTTGGTACC ANGAGACATT ATTATAACCA      420

CCAACGTCAC TGCTGGTTCC ANTGCAGGGA AAATGGTTGA TCNAACTGTC CAAGAAAACC      480

ACTACGTCCA TACCAATCCA CTAATTGCCN GCCGCCTGCA GGTTCAACCA TATTGGGGAA      540

NAACTCCCCN CCGCCGTTTG GGATTGNCAT NAACCTTTGA AATTTTTTCC TATTANTTGT      600

CCCCCTAAAA TAAACCNTTG GGCNTTAATC CATTGGGTCC ATANCTTNTT TNCCCGGTTT      660

TTAAAANTTG TTTATCCCGC CNCCCNATTT CCCCCCCAAC TTTCCAAAAC CCGAAACCNT      720

TNAAATTTNT TNAAACCCTG GGGGGTTCCC NNAATTNNAN TTNAANCTNC C               771
```

(2) INFORMATION FOR SEQ ID NO: 242:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 242:

```
TGGGCACCTT CAATATCGGG CTCATCGATA ACATCACGCT GCTGATGCTG CTGTTGCTGG       60

TCCTCTCTAG GAACCTCTGG ATTTTCAAAT TCTTTGAGGA ATTCATCCAA ATTATCTGCC      120

TCTCCTCCTT TCCTCCTTTT TCTAAGGTCT TCTGGTACAA GCGGTCA                   167
```

(2) INFORMATION FOR SEQ ID NO: 243:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 243:

```
TTGGGCACCT TCAATATCTA CTGATCTAAA TAGTGTGGTT TGAGGCCTCT TGTTCCTGGC       60

TAAAAATCCT TGGCAAGAGT CAATCTCCAC TTTACAATAG AGGTAAAAAT CTTACAATGG      120

ATATTCTTGA CAAAGCTAGC ATAGAGACAG CAATTTTACA CAAGGTATTT TTCACCTGTT      180

TAATAACAGT GGTTTTCCTA CACCCATAGG GTGCCACCAA GGGAGGAGTG CACAGTTGCA      240

GAAACAAATT AAGATACTGA AGACAACACT ACTTACCATT TCCCGTATAG CTAACCACCA      300

GTTCAACTGT ACATGTATGT TCTTATGGGC AATCAAGA                             338
```

(2) INFORMATION FOR SEQ ID NO: 244:

(i) SEQUENCE CHARACTERISTICS:
        (A) LENGTH: 346 base pairs (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 244:

| | | | | | |
|---|---|---|---|---|---|
| TTTTTGGCTC | CCATACAGCA | CACTCTCATG | GGAAATGTCT | GTTCTAAGGT | CAACCCATAA | 60 |
| TGCAAAAATC | ATCAATATAC | TTGAAGATCC | CCGTGTAAGG | TACAATGTAT | TTAATATTAT | 120 |
| CACTGATACA | ATTGATCCAA | TACCAGTTTT | AGTCTGGCAT | TGAATCAAAT | CACTGTTTTT | 180 |
| GTTGTATAAA | AAGAGAAATA | TTTAGCTTAT | ATTTAAGTAC | CATATTGTAA | GAAAAAAGAT | 240 |
| GCTTATCTTT | ACATGCTAAA | ATCATGATCT | GTACATTGGT | GCAGTGAATA | TTACTGTAAA | 300 |
| AGGGAAGAAG | GAATGAAGAC | GAGCTAAGGA | TATTGAAGGT | GCCCAA | | 346 |

(2) INFORMATION FOR SEQ ID NO: 245:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 245:

| | | | | | |
|---|---|---|---|---|---|
| ACCAATCCCA | CACGGATACT | GAGGGACAAG | TATATCATCC | CATTTCATCC | CTACAGCAGC | 60 |
| AACTTCATGA | GGCAGGAGTT | ATTAGTCCCA | TTTTACAGAA | GAGGAAACTG | AGACTTAGGG | 120 |
| AGATCAAGTA | ATTTGCCCAG | GTCGCACAAT | TAGTGATAGA | GCCAGGGCTT | GAAGCGACGT | 180 |
| CTGTCTTAAG | CCAATGACCC | CTGCAGATTA | TTAGAGCAAC | TGTTCTCCAC | AACAGTGTAA | 240 |
| GCCTCTTGCT | ANAAGCTCAG | GTCCACAAGG | GCAGAGATTT | TTGTCTGTTT | TGCTCATTGC | 300 |
| TCCTTCCCCA | TTGCTTAGAG | CAGGGTCTGC | CACGAANCAG | GTTCTCAATG | CATAGTTATT | 360 |
| AAATGTATAT | AAGAGCAAAC | ATATGTTACA | GAGAACTTTC | TGTATGCTTG | TCACTTACAT | 420 |
| GAATCACCTG | TGANATGGGT | ATGCTTGTTC | CCCANTGTTG | CAGATNAAGA | TATTGAANGT | 480 |
| GCCCAAATCA | CTANTTGCGG | GCGCCTGCAN | GTCCANCATA | T | | 521 |

(2) INFORMATION FOR SEQ ID NO: 246:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 246:

| | | | | | |
|---|---|---|---|---|---|
| TGGAACCAAT | CCAAATACCC | ATCAATGATA | GACTGGATAA | AGAAAATTTG | GCACATGTTC | 60 |
| ACCATGAAAT | ACTATGCAGC | CATAAAAAAG | GATGAGTTCA | TATCCTTTGC | AGGGACATGG | 120 |
| ATGAAGCTGG | AGACCATCAT | TCTCAGCAAA | CTAACAAGGG | AACAGAAAAC | CAAACACTGC | 180 |

-continued

| | | | | | |
|---|---|---|---|---|---|
| ATGTTCTCAC | TCTTAAGTGG | GAGCTGAACA | ATGAGAACAC | ATGGACACAG | GGAGGGGAAC | 240 |
| ATCACACAGT | GGGGCCTGCT | GGTGGGTAGG | GGTCTAGGGG | AGGGATAGCA | TTAGGAGAAA | 300 |
| TACCTAATGT | AGATGACGGG | TTGATGGGTG | CAGCAAACCA | CCATGACACG | TGTATACCTA | 360 |
| TGTAACAAAC | CTGCATGTTC | TGCACATGTA | CCCCAGAACT | TAAAGTGTTA | ATAAAAAAAT | 420 |
| TAAGAAAAAA | GTTAAGTATG | TCATAGATAC | ATAAAATATT | GTANATATTG | AAGGTGCCCA | 480 |
| AA | | | | | | 482 |

(2) INFORMATION FOR SEQ ID NO: 247:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 247:

| | | | | | |
|---|---|---|---|---|---|
| TTCGATACAG | GCACAGAGTA | AGCAGAAAAA | TGGCTGTGGT | TTAACCAAGT | GAGTACAGTT | 60 |
| AAGTGAGAGA | GGGGCAGAGA | AGACAAGGGC | ATATGCAGGG | GGTGATTATA | ACAGGTGGTT | 120 |
| GTGCTGGGAA | GTGAGGGTAC | TCGGGGATGA | GGAACAGTGA | AAAAGTGGCA | AAAAGTGGTA | 180 |
| AGATCAGTGA | ATTGTACTTC | TCCAGAATTT | GATTTCTGGN | GGAGTCAAAT | AACTATCCAG | 240 |
| TTTGGGGTAT | CATANGGCAA | CAGTTGAGGT | ATAGGAGGTA | GAAGTCNCAG | TGGGATAATT | 300 |
| GAGGTTATGA | ANGGTTTGGT | ACTGACTGGT | ACTGACAANG | TCTGGGTTAT | GACCATGGGA | 360 |
| ATGAATGACT | GTANAAGCGT | ANAGGATGAA | ACTATTCCAC | GANAAAGGGG | TCCNAAAACT | 420 |
| AAAAANNNAA | GNNNNNGGGG | AATATTATTT | ATGTGGATAT | TGAANGTGCC | CAAA | 474 |

What is claimed is:

1. An isolated DNA molecule comprising SEQ ID NO: 211.

2. An isolated DNA molecule comprising a sequence that hybridizes to SEQ ID NO: 211 under stringent conditions, wherein said DNA molecule is expressed at a greater level in human breast tumor tissue than in normal breast tissue.

3. An isolated DNA molecule comprising a sequence that is at least 80% identical to SEQ ID NO: 211, wherein said DNA molecule is expressed at a greater level in human breast tumor tissue than in normal breast tissue.

* * * * *